US011603390B2

(12) United States Patent
Langedijk et al.

(10) Patent No.: US 11,603,390 B2
(45) Date of Patent: Mar. 14, 2023

(54) STABILIZED FILOVIRUS GLYCOPROTEIN TRIMERS

(71) Applicant: JANSSEN VACCINES & PREVENTION B.V., Leiden (NL)

(72) Inventors: Johannes Langedijk, Leiden (NL); Lucy Rutten, Leiden (NL); Sven Blokland, Leiden (NL)

(73) Assignee: JANSSEN VACCINES & PREVENTION B.V., Leiden (NL)

( * ) Notice: Subject to any disclaimer, the term of this patent is extended or adjusted under 35 U.S.C. 154(b) by 7 days.

(21) Appl. No.: 17/266,404

(22) PCT Filed: Aug. 13, 2019

(86) PCT No.: PCT/EP2019/071732
§ 371 (c)(1),
(2) Date: Feb. 5, 2021

(87) PCT Pub. No.: WO2020/035497
PCT Pub. Date: Feb. 20, 2020

(65) Prior Publication Data
US 2021/0292371 A1  Sep. 23, 2021

(30) Foreign Application Priority Data

Aug. 13, 2018 (EP) ..................... 18188675

(51) Int. Cl.
*A61K 39/12* (2006.01)
*C07K 14/005* (2006.01)
(52) U.S. Cl.
CPC ............ *C07K 14/005* (2013.01); *A61K 39/12* (2013.01); *C12N 2760/14022* (2013.01); *C12N 2760/14034* (2013.01); *C12N 2760/14051* (2013.01); *C12N 2760/14122* (2013.01); *C12N 2760/14134* (2013.01); *C12N 2760/14151* (2013.01); *C12N 2760/14222* (2013.01); *C12N 2760/14234* (2013.01); *C12N 2760/14251* (2013.01)

(58) Field of Classification Search
CPC ....................... A61K 39/12; C12N 2760/14122
See application file for complete search history.

(56) References Cited

U.S. PATENT DOCUMENTS

| 11,135,280 B2 * | 10/2021 | Aman .................... C12N 15/86 |
| 2015/0291935 A1 | 10/2015 | BarOuch et al. |

FOREIGN PATENT DOCUMENTS

| WO | 2007/104792 A2 | 9/2007 | |
| WO | 2014/124301 A1 | 8/2014 | |
| WO | 2017/037196 A1 | 3/2017 | |
| WO | WO-2017172622 A1 * | 10/2017 | ............. A61K 39/12 |
| WO | 2020/035497 A1 | 2/2020 | |

OTHER PUBLICATIONS

Rutten, L, et al., Mar. 2020, Structure-based design of prefusion-stabilized filovirus glycoprotein trimers, Cell Reports 30:4540-4550.*
Comparative Seroprevalence and Immunogenicity of Six Rare Serotype Recombinant Adenovirus Vaccine Vectors from Subgroups B and D; Journal 01' Virology, May 2007, pp. 4654-4663. JVI Accepted Manuscript Posted Online Jun. 7, 2017; J. Virol. doi:10.1128/JVI.00443-17 Copyright © 2017 American Society for Microbiology. All Rights Reserved; 41 pgs.
A Bioengineering Approach for Rational Vaccine Design towards the Ebola Virus; Sophia Banton, et al.; From Sixth International Society for Computational Biology (ISCB) Student Council Symposium Boston, MA, USA. Jul. 9, 2010; 2 pgs.
Host-Primed Ebola Virus GP Exposes a Hydrophobic NPC1 Receptor-Binding Pocket, Revealing a Target for Broadly Neutralizing Antibodies; Zachary A. Bornholdt et al.; American Society for Microbiology; Jan./Feb. 2016 vol. 7 Issue 1; 11 pgs.
Database Accession No. BEJ1909 Ebola Virus Glycoproten Mutant K588A; Guedj J., et al.; 4 pgs.
The Use of AlphaScreen Technology in HTS: Current Status; Richard M. Eglen et al; Current Chemical Genomics, 2008, 1, pp. 2-10.
Potential Vaccines and Post-Exposure Treatments for Filovirus Infections; Brian M. Friedrich; ISSN 1999-4915 www.mdpi.com/journal/viruses; pp. 619-1650.
Plos Medicine Research Article—Antiviral Efficacy of Favipiravir Against Ebola Virus: A Translational Study in Cynomolgus Macaques; Jeremie Guedj et al.; 21 pgs.
Elsevier—Virus-like Particles as a Jighly Efficient Vaccine Platform: Diversity of Targets and Production Systems and Advances in Clinical Development; Natasha Kushnir, et al.; pp. 58-83; http://www.elsevier.com/locate/vaccine.
Nature—Structure of the Ebola Virus Glycoprotein Bound to an Antibody from a Human Survivor; Jeffrey E. Lee et al.; vol. 454, Jul. 10, 2008; 7 pgs.
National Institute of Health Public Access; Ebolavirus Glycoprotein Structure and Mechanism of Entry; Jeffrey E. Lee et al.; Future Viral. 2009 ; 4( 6): 621-635, 23 pgs.
Supplement Article: Characterization of Immune Responses Induced by Ebola Virus Glycoprotein (GP) and Truncated GP Isoform DNA Vaccines and Protection Against Lethal Ebola Virus Challenge in Mice; Wenfang Li,et al.; 6 pgs.

(Continued)

*Primary Examiner* — Jeffrey S Parkin
(74) *Attorney, Agent, or Firm* — Kramer & Amado, P.C.

(57) ABSTRACT

Filovirus glycoprotein mutations that stabilize the trimeric form of the glycoprotein are provided. The Filovirus glycoproteins have certain amino acid substitutions at specified positions in the glycoprotein sequence. The Filovirus glycoproteins described herein have an improved percentage of trimer formation and/or an improved trimer yield as compared to a Filovirus glycoprotein that does not have one or more of the indicated amino acid substitutions. Also provided are nucleic acid molecules and vectors encoding the Filovirus glycoproteins, as well as compositions containing the Filovirus glycoproteins, nucleic acid, and vectors.

21 Claims, 13 Drawing Sheets
Specification includes a Sequence Listing.

(56) References Cited

OTHER PUBLICATIONS

Elsevier—Self-assembling Protein Nanoparticles in the Design of Vaccines; Jacinto López-Sagaseta, et al.; Computational and Structural Biotechnology Journal 14 (2016); pp. 58-68.
Department of Health and Human Services; Structures of Ebola Virus GP and sGP in Complex with Therapeutic Antibodies; Jesper Pallesen, et al., Nat Microbiol. Author manuscript (2016); 23 pgs.
Novovax—7th International Symposium of Fioloviruses; Recombinant EB V/ akona lycoprotein ( P) Nanopa icle Vaccine Produced in Sf9 Insect Cells; Gail Smith, et al.; 29 pgs.
Spatial Localization of the Ebola Virus Glycoprotein Jv1udn-Like Domain Determined by Cryo-Electron Tomography Erin E. H. Tran, et al.; Journal of Virology; Sep. 2014 vol. 88 No. 18; p. 1095B-10962; 5 pgs.
Cell—Ebola Viral Glycoprotein Bound to Its Endosomal Receptor Niemann-Pick C1; Han Wang, et al.; 12 pgs.
Elsevier—Vaccine 32 (2014)—Nanoparticle Vaccines, Liang Zhao, et al., pp. 327-337.
Nature—Research Letter—Toremifene Interacts with and Destabilizes the Ebola Virus Glycoprotein, Yuguang Zhao, et al., Jul. 7, 2016—vol. 535.
Written Opinion of the International Searching Authority—Application No. PCT/EP2019/071732 dated Sep. 13, 2019; 7 pgs.
PCT International Search Report re Application No. PCT/EP2019/071732 dated Sep. 13, 2019; 7 pgs.

\* cited by examiner

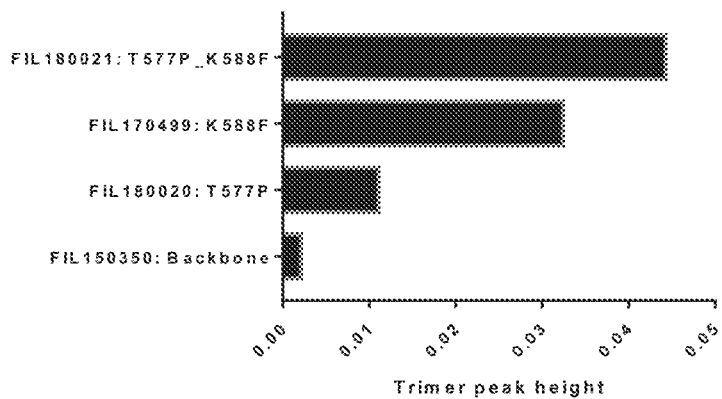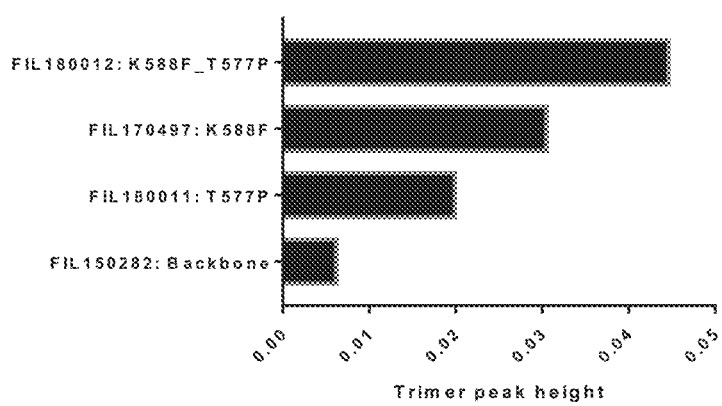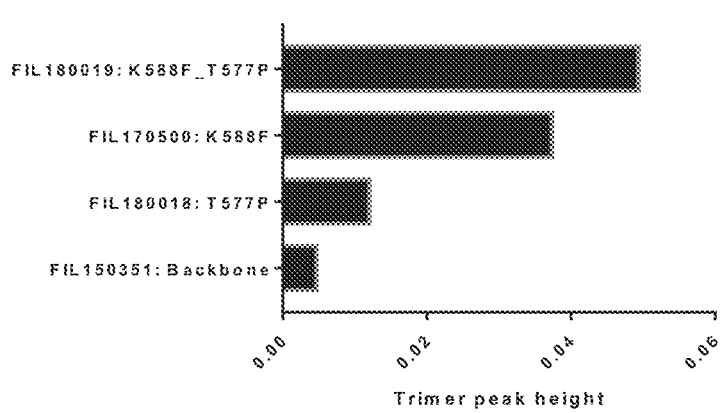
FIG. 4 - continued

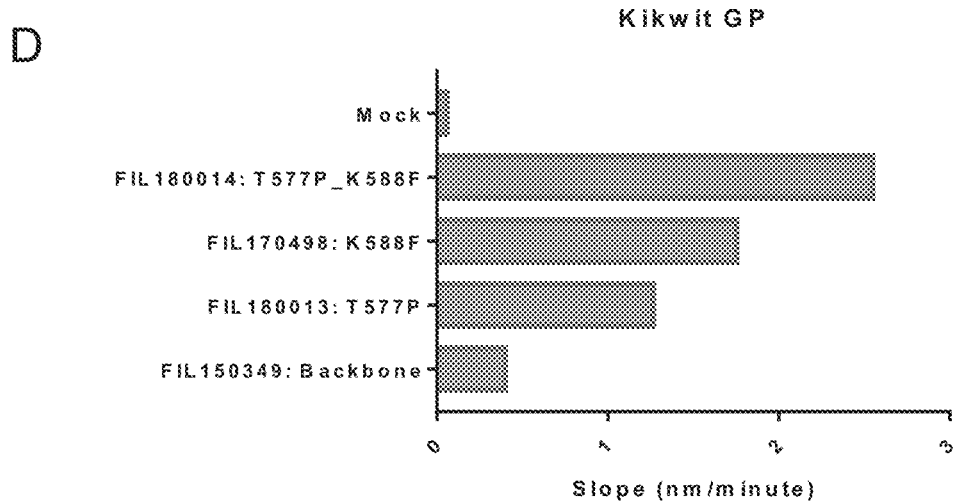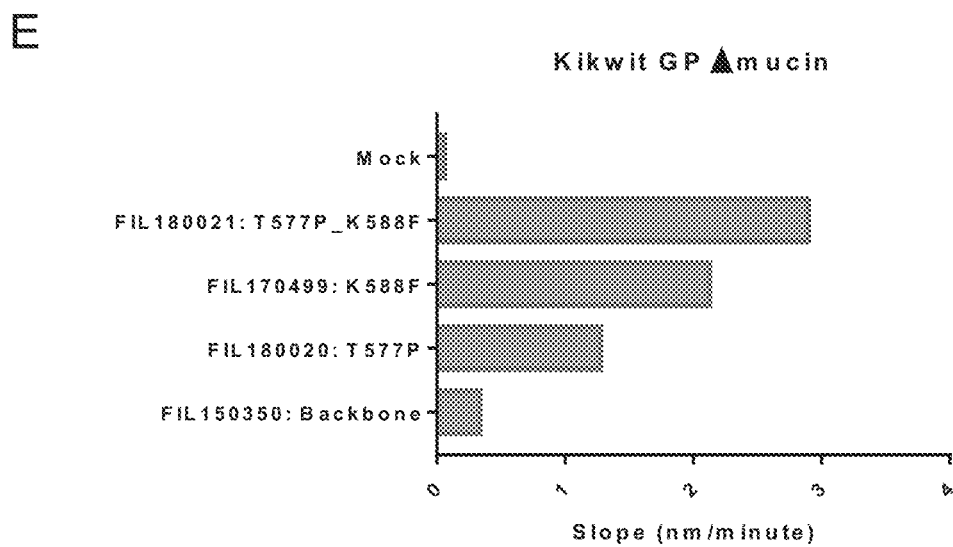
FIG. 5 - continued

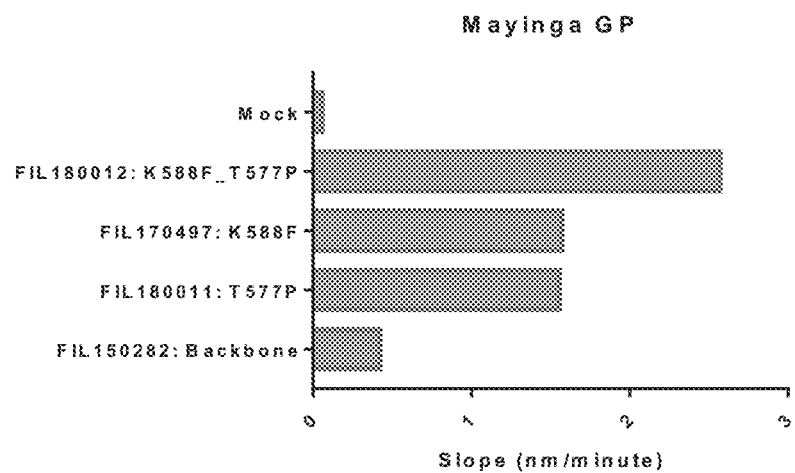
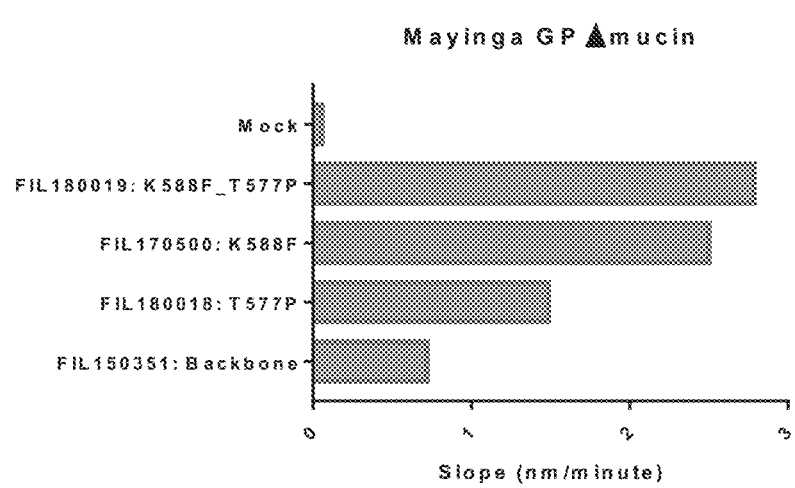
FIG. 5 - continued

A

Mayinga GP

- FIL172550: K588Y
- FIL172549: K588M
- FIL172548: K588L
- FIL172547: K588I
- FIL172546: K588V
- FIL172545: K588A
- FIL170497: K588F
- FIL150282: Backbone Trimer peak height

B

Mayinga GP

- Mock
- FIL172550: K588Y
- FIL172549: K588M
- FIL172548: K588L
- FIL172547: K588I
- FIL172546: K588V
- FIL172545: K588A
- FIL170497: K588F
- FIL150282: Backbone Slope (nm/minute)

Mayinga GP ▲mucin

| Variant | |
|---|---|
| FIL180338: K588E | |
| FIL180337: K588D | |
| FIL180336: K588H | |
| FIL180335: K588R | |
| FIL180331: K588Q | |
| FIL180330: K588N | |
| FIL180329: K588T | |
| FIL180328: K588S | |
| FIL172537: K588Y | |
| FIL180334: K588P | |
| FIL180333: K588G | |
| FIL180332: K588C | |
| FIL172536: K588M | |
| FIL180327: K588W | |
| FIL172535: K588L | |
| FIL172534: K588I | |
| FIL172533: K588V | |
| FIL172532: K588A | |
| FIL170500: K588F | |
| FIL170500: K588F | |
| FIL150351: Backbone | |
| FIL150351: Backbone | |

D

Trimer peak height

Mayinga GP Δmucin

| Label | |
|---|---|
| Mock | |
| FIL180338 K588E | |
| FIL180337 K588D | |
| FIL180336 K588H | |
| FIL180335 K588R | |
| FIL180331 K588Q | |
| FIL180330 K588N | |
| FIL180329 K588T | |
| FIL180328 K588S | |
| FIL172537 K588Y | |
| FIL180334 K588P | |
| FIL180333 K588G | |
| FIL180332 K588C | |
| FIL172536 K588M | |
| FIL180327 K588W | |
| FIL172535 K588L | |
| FIL172534 K588I | |
| FIL172533 K588V | |
| FIL172532 K588A | |
| FIL170500 K588F | |
| FIL170500 K588F | |
| FIL150351 Backbone | |
| FIL150351 Backbone | |

Slope (nm/minute)

FIG. 6 - continued

FIG. 7 ial reservoirs complicates efforts to design a vaccine that protects against all species of filoviruses.

STABILIZED FILOVIRUS GLYCOPROTEIN TRIMERS

INCORPORATION BY REFERENCE

The present application incorporates by reference a sequence listing, in electronic format, entitled 0315 EP P00 PRI_SQL.txt, created Jan. 7, 2021, which is 197 kb in size. The information in the electronic format of the sequence listing is incorporated herein by reference in its entirety.

FIELD OF THE INVENTION

The current disclosure is directed to stabilized Filovirus glycoprotein trimers

BACKGROUND OF THE INVENTION

Ebolaviruses, such as Zaire ebolavirus (EBOV) and Sudan ebolavirus (SUDV), and the closely related Marburg virus (MARV), are associated with outbreaks of highly lethal Ebola Hemorrhagic Fever (EHF) in humans and primates in North America, Europe, and Africa. These viruses are filoviruses that are known to infect humans and non-human primates with severe health consequences, including death. Filovirus infections have resulted in case fatality rates of up to 90% in humans. EBOV, SUDV, and MARV infections cause EHF with death often occurring within 7 to 10 days post-infection. EHF presents as an acute febrile syndrome manifested by an abrupt fever, nausea, vomiting, diarrhea, maculopapular rash, malaise, prostration, generalized signs of increased vascular permeability, coagulation abnormalities, and dysregulation of the innate immune response. Much of the disease appears to be caused by dysregulation of innate immune responses to the infection and by replication of virus in vascular endothelial cells, which induces death of host cells and destruction of the endothelial barrier. Filoviruses can be spread by small particle aerosol or by direct contact with infected blood, organs, and body fluids of human or NHP origin. Infection with a single virion is reported to be sufficient to cause Ebola hemorrhagic fever (EHF) in humans. Presently, there is no therapeutic or vaccine approved for treatment or prevention of EHF. Supportive care remains the only approved medical intervention for individuals who become infected with filoviruses.

As the cause of severe human disease, filoviruses continue to be of concern as both a source of natural infections, and also as possible agents of bioterrorism. The reservoir for filoviruses in the wild has not yet been definitively identified. Four subtypes of Ebolaviruses have been described to cause EHF, i.e., those in the Zaire, Sudan, Bundibugyo and Ivory Coast episodes (Sanchez, A. et al. 1996 PNAS USA 93:3602-3607). These subtypes of Ebolaviruses have similar genetic organizations, e.g., negative-stranded RNA viruses containing seven linearly arrayed genes. The structural gene products include, for example, the envelope glycoprotein that exists in two alternative forms, a secreted soluble glycoprotein (ssGP) and a transmembrane glycoprotein (GP) generated by RNA editing that mediates viral entry (Sanchez, et al. 1996 PNAS USA 93:3602-3607).

It has been suggested that immunization may be useful in protecting against Ebola infection because there appears to be less nucleotide polymorphism within Ebola subtypes than among other RNA viruses (Sanchez et al. 1996 PNAS USA 93:3602-3607). Until recently, developments of preventive vaccines against filoviruses have had variable results, partly because the requirements for protective immune responses against filovirus infections are poorly understood. Additionally, the large number of filoviruses circulating within natural reservoirs complicates efforts to design a vaccine that protects against all species of filoviruses.

Vaccine candidates are in development based on a variety of platform technologies including replication competent vectors (e.g. Vesicular Stomatitis Virus; Rabies virus; Parainfluenza Virus); replication incompetent vectors (Adenovirus, Modified Vaccinia Ankara Virus); protein subunits inclusive of Virus Like Particles expressed in bacterial cells, insect cells, mammalian cells, plant cells; DNA vaccines; and/or live and killed attenuated filovirus (Friedrich et al., Viruses. 2012 September; 4(9):1619-50). The EBOV glycoprotein GP is an essential component of a vaccine that protects against exposures with the same species of EBOV. Furthermore, inclusion of the GP from EBOV and SUDV, the two most virulent species of ebolaviruses, can protect monkeys against EBOV and SUDV intramuscular exposures, as well as exposures with the distantly related Bundibugyo (BDBV), Tai Forest ebolavirus (TAFV; formerly known as Ivory Coast or Cote d'Ivoire) species. Likewise, inclusion of the GP from MARV can protect monkeys against MARV intramuscular and aerosol exposures. The development of medical countermeasures for these viruses is a high priority, in particular the development of a PAN-filovirus vaccine—that is one vaccine that protects against all pathogenic filoviruses.

The Ebola glycoprotein (GP) gene encodes a pre-secreted glycoprotein (pre-sGP), a small nonstructural secreted glycoprotein ssGP and a surface expressed GP. The ssGP, which is the primary product of the GP gene, is secreted but it is not recognized by virus-neutralizing anti-GP mAbs as opposed to the surface expressed GP. The surface expressed GP consists of GP1 and GP2, which are linked together with a natural disulfide. GP1 consist of a core followed by a glycan cap and a mucin-like domain. GP2 contains the transmembrane region. FIG. 1 gives a schematic representation of the structure of a surface expressed Filovirus GP showing the GP1 head domain (black) that includes the mucin-like domain (grey), and the GP2 domain that includes the refolding region 1 (RR1), base helix (between RR1 and RR2), refolding region 2 (RR2) and the transmembrane domain (TM).

Like other viral fusion proteins, Ebola GP is a dynamic fusion machine that drives membrane fusion by irreversible protein refolding from a metastable pre-fusion conformation to a stable post-fusion conformation. The metastable pre-fusion conformation is a trimer consisting of three GP1s and three GP2s.

A number of crystal structures and EM structures have been determined for Ebola GP expressed in insect cells (Wang et al. Cell. 2016 Jan. 14; 164(1-2):258-268, Bornholdt et al. MBio. 2016 Feb. 23; 7(1):e02154-15, Pallesen et al. Nat Microbiol. 2016 Aug. 8; 1(9):16128) and HEK293 cells, but two of the ones produced in HEK293 cells either contain a fibritin or a GCN4 trimerization motif. Only one of the trimer structure was not fused to a heterologous trimerization domain (Lee et al. Nature. 2008 Jul. 10; 454(7201):177-82). The focus in this study was to obtain high quality soluble Ebola prefusion GP trimers expressed in mammalian cells without a heterologous trimerization domain. Soluble GP based on the ectodomain forms mostly dimers and monomers when expressed in HEK293T-cells (Lee et al. Nature. 2008 Jul. 10; 454(7201):177-82 suppl. FIG. 8).

For the purpose of vaccine development, it is preferred to use glycoproteins that can induce bNAbs. However, most bNAbs only recognize the native GP conformation before it undergoes any conformation changes. Developing a stable GP in its native-like compact and closed conformation, while minimizing the presentation of non-native and thus non-neutralizing epitopes, could therefore improve the efficiency of generating bNAbs. Previous efforts to produce a stable glycoprotein have been disclosed in for instance the international patent application PCT/EP2016/070654, wherein certain stabilizing mutations of Filovirus glycoprotein have been described.

However, there is still a need for Filovirus glycoprotein trimers with improved stability that have improved percentage of trimer formation and improved trimer yield. Preferably, such stabilized trimers of Filovirus glycoproteins would also display good binding with broadly neutralizing antibodies (bNAbs), and relatively limited binding to non-broadly neutralizing Abs (non-bNAbs). It is an object of the invention to provide Filovirus GPs that have improved trimer percentages, and preferably also improved trimer yields.

BRIEF SUMMARY OF THE INVENTION

The invention relates to recombinant Filovirus glycoproteins that have improved percentage of trimer formation and/or improved trimer yields as compared to previously described Filovirus GP trimers. Glycoprotein folding is optimized, such that the GP trimers resemble more the native protein configuration, and regions of the prefusion-closed conformation important for the fusion process are stabilized by mutations described herein. This provides a universal approach to optimize the folding and stability of Filovirus GP trimers. The resulting stable and well-folded Filovirus GP trimers which resemble more the native protein configuration are useful for immunization purposes, e.g. to improve chances of inducing broadly neutralizing antibodies and reducing induction of non-neutralizing and weakly neutralizing antibodies upon administration of the recombinant Filovirus GP trimers. The invention also relates to isolated nucleic acid molecules and vectors encoding the recombinant Filovirus glycoproteins, cells comprising the same, and compositions of the recombinant Filovirus glycoprotein, nucleic acid molecule, vector, and/or cells.

In one general aspect, the invention relates to recombinant Filovirus proteins having particular amino acid residues at identified positions in the GP sequence that stabilize the formation of trimers.

In certain embodiments, a recombinant Filovirus glycoprotein of the invention comprises a non-charged amino acid residue, at position 588, wherein the numbering of the positions is according to the numbering of the GP in Z/Zaire/Yambuku/1976/057935 and wherein the non-charged amino acid residue in not a cysteine.

In certain preferred embodiments, the indicated non-charged amino acid residue at position 588 is a hydrophobic amino acid residue selected from the group of F, I, A, L, M, V, W and Y.

In certain preferred embodiments, the indicated non-charged amino acid residue at position 588 is a hydrophobic amino acid residue selected from the group of F, I, L, M, V and Y.

In a more preferred embodiment, the indicated hydrophobic amino acid residue at position 588 is F.

In certain preferred embodiments, the recombinant Filovirus glycoprotein of the invention further comprises an amino acid residue P at position 577 and/or 579, wherein the numbering of the positions is according to the numbering of the GP in Z/Zaire/Yambuku/1976/057935.

In certain preferred embodiments, the recombinant Filovirus GP of the invention is from a strain selected from the group of Mayinga, Makona, kikwit, Sudan Gulu and Marburg.

In certain embodiments, the recombinant Filovirus GP of the invention is selected from the group consisting of:
1) a Zaire Ebolavirus Mayinga glycoprotein comprising the amino acid sequence of SEQ ID NO: 2 or a Zaire Ebolavirus Mayinga glycoprotein with a deletion between amino acid residues 320 until 476, comprising the amino acid sequence of SEQ ID NO: 6; and
2) a Zaire Ebolavirus Makona GP glycoprotein comprising the amino acid sequence of SEQ ID NO: 10 or a Zaire Ebolavirus Makona GP glycoprotein with a deletion between amino acid residues 314 until 472, comprising the amino acid sequence of SEQ ID NO: 14; and
3) a Zaire Ebolavirus Kikwit glycoprotein comprising the amino acid sequence of SEQ ID NO: 19 or a Zaire Ebolavirus Kikwit glycoprotein with a deletion between amino acid residues 314 until 472, comprising the amino acid sequence of SEQ ID NO: 23; and
4) a Marburg glycoprotein with a deletion between amino acid residues 255 until 423, comprising the amino acid sequence of SEQ ID NO: 27, wherein the numbering of the positions is according to the numbering of the GP in Z/Zaire/Yambuku/1976/057935.

In another general aspect, the invention relates to a trimeric complex comprising a noncovalent oligomer of three of the recombinant Filovirus glycoproteins of the present invention.

In another general aspect, the invention relates to a particle, preferably a nanoparticle, e.g. a self-assembling nanoparticle, displaying on its surface a recombinant Filovirus GP or a trimeric complex of the invention.

In another general aspect, the invention relates to an isolated nucleic acid molecule encoding a recombinant Filovirus GP of the invention and vectors comprising the isolated nucleic acid molecule operably linked to a promoter. In one embodiment, the vector is a viral vector. In another embodiment, the vector is an expression vector. In one preferred embodiment, the viral vector is an adenovirus vector.

Another general aspect relates to a host cell comprising the isolated nucleic acid molecule or vector encoding the recombinant Filovirus GP of the invention. Such host cells can be used for recombinant protein production, recombinant protein expression, or the production of viral particles.

Another general aspect relates to methods of producing a recombinant Filovirus GP, comprising growing a host cell comprising an isolated nucleic acid molecule or vector encoding the recombinant Filovirus GP of the invention under conditions suitable for production of the recombinant Filovirus GP.

Yet another general aspect relates to a composition comprising a recombinant Filovirus GP, trimeric complex, isolated nucleic acid molecule, vector, or host cell as described herein, and a pharmaceutically acceptable carrier.

Yet another general aspect of the invention relates to a method of improving the trimer formation of a Filovirus glycoprotein, the method comprising substituting the amino acid residue at position 588 of the glycoprotein for a non-charged amino acid residue, wherein the numbering of the positions is according to the numbering of the GP in Z/Zaire/Yambuku/1976/057935, and wherein the non-charged amino acid residue in not a cysteine.

In a preferred embodiment, the method of improving the trimer formation of a Filovirus glycoprotein, further comprises substituting the amino acid residue at position 577 and/or 579 of the glycoprotein for a P residue, wherein the numbering of the positions is according to the numbering of the GP in Z/Zaire/Yambuku/1976/057935.

BRIEF DESCRIPTION OF THE FIGURES

The foregoing summary, as well as the following detailed description of the invention, will be better understood when read in conjunction with the appended figures. It should be understood that the invention is not limited to the precise embodiments shown in the figures.

FIG. 4. Trimer content based on analytical SEC. Trimer content based on trimer peak heights measured in analytical SEC patterns in FIG. 3. The mutations tested are T577P, K588F and T577P-K588F. The mutations were tested in the following backbones: A) Makona GP, B) Makona Δmucin-like domain GP, C) Kikwit GP, D) KikwitΔmucin-like domain GP, E) Mayinga GP, F) Mayinga Δmucin-like domain GP.

FIG. 5A) One example (Kikwit GP) of the biolayer interferometry curves as measured in Octet with the asterisk indicating the dotted line at the time-point at which the slope of binding was determined. FIG. 5B-5D show the bar graphs of the slope of binding of antibody 100 in nm/minute. Wildtype GP and variants (T577P, K588F and T577P-K588F), were tested in cell culture supernatant for binding to Mab 100. The mutations were tested in the following backbones: B) Makona GP, C) Makona Δmucin-like domain GP, D) Kikwit GP, E) Kikwit Δmucin-like domain GP, F) Mayinga GP, G) Mayinga Δmucin-like domain GP.

FIG. 6. A, C) Trimer content based on analytical SEC and B, D) association slope measured using BioLayer Interferometry with Mab 100 for the K588 substituted with several hydrophobic residues was tested in Mayinga GP (A and B) and K588 substitution with all possible amino acids was tested in Mayinga Δmucin-like domain GP (C and D) backbone FIG. 7. Analytical SEC on cell culture supernatants containing Marburg Δmucin-like domain GPs. The trimer peak is indicated with a dashed line labeled with 'trimer'. Expression levels, measured using analytical SEC, of the Marburg Δmucin-like GP backbone (black broken line) and variants with H588F (light grey solid line) and H588I (dark grey solid line) substitutions are shown.

DETAILED DESCRIPTION OF THE INVENTION

Figure 1:
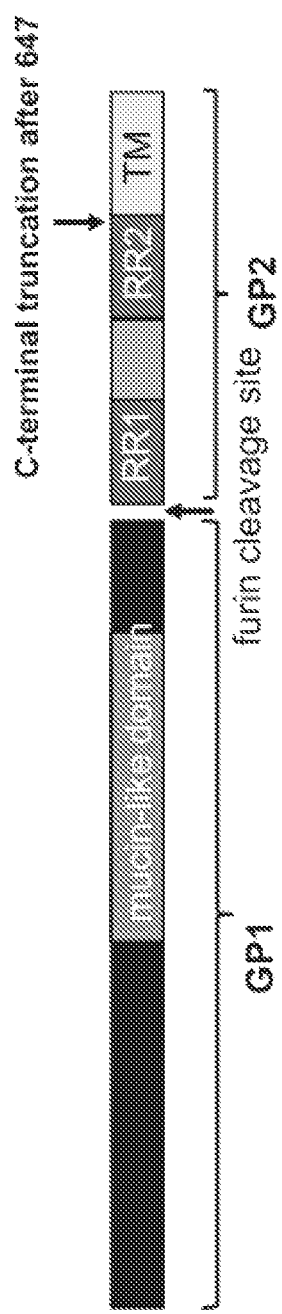
FIG. 1. Schematic representation of the structure of a full-length Filovirus GP.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about". Thus, a numerical value typically includes ±10% of the recited value. As used herein, the use of a numerical range expressly includes all possible subranges, all individual numerical values within that range, including integers within such ranges and fractions of the values unless the context clearly indicates otherwise.

Amino acids are referenced throughout the disclosure. There are twenty naturally occurring amino acids, as well as many non-naturally occurring amino acids. Each known amino acid, including both natural and non-natural amino acids, has a full name, an abbreviated one letter code, and an abbreviated three letter code, all of which are well known to those of ordinary skill in the art. For example, the three and one letter abbreviated codes used for the twenty naturally occurring amino acids are as follows: alanine (Ala; A), arginine (Arg; R), aspartic acid (Asp; D), asparagine (Asn; N), cysteine (Cys; C), glycine (Gly; G), glutamic acid (Glu; E), glutamine (Gln; Q), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y) and valine (Val; V). Amino acids can be referred to by their full name, one letter abbreviated code, or three letter abbreviated code.

Unless the context clearly dictates otherwise, the numbering of positions in the amino acid sequence of a Filovirus glycoprotein as used herein is according to the numbering in the glycoprotein in Z/Zaire/Yambuku/1976/057935, also referred to as the Mayinga isolate as for instance set forth in Sanchez et al. Proc Natl Acad Sci USA. 1996 Apr. 16; 93(8):3602-7, which is incorporated by reference herein in its entirety. Numbering according to Z/Zaire/Yambuku/1976/057935 is conventional in the field of Filovirus GPs. The GP of the Z/Zaire/Yambuku/1976/057935 strain has the amino acid sequence shown in SEQ ID NO: 1. Alignment of a Filovirus GP sequence of interest with this sequence can be used to find the corresponding amino acid numbering in the sequence of interest.

A 'corresponding position' in a Filovirus GP refers to position of the amino acid residue when at least two Filovirus GP sequences are aligned. Unless otherwise indicated, amino acid position numbering for these purposes is according to the numbering in the GP of the Z/Zaire/Yambuku/1976/057935 isolate (SEQ ID NO: 1), as customary in the field.

A 'stabilizing mutation' or 'stabilizing substitution' as used herein is a mutation as described herein, which increases the percentage of trimer and/or the trimer yield (which can for instance be measured using Native-PAGE, AlphaLISA or analytical SEC assays described herein) of a Filovirus GP as compared to a parent molecule when the mutation is introduced by substitution of the corresponding amino acid in said parent molecule. The amino acids resulting from such stabilizing mutations typically are rarely, if at all, found in glycoproteins of wild-type Filovirus isolates.

The terms 'natural' or 'wild-type' are used interchangeably herein when referring to Filovirus strains (or glycoproteins therefrom), and refer to Filovirus strains (or glycoproteins therefrom) as occurring in nature, e.g. such as in Filovirus-infected patients.

The invention generally relates to recombinant Filovirus GP comprising certain amino acid substitutions at indicated positions in the GP sequence that stabilize the trimer form of the glycoprotein. Introducing one or more of the identified amino acid substitutions of the invention into the sequence of a Filovirus glycoprotein can result in an increased percentage of trimer formation and/or an increased trimer yield. This can for instance be determined by using trimer-specific antibodies, size exclusion chromatography or measuring the melting temperature. Binding affinity to antibodies that bind to correctly folded (stable trimeric) or alternatively to incorrectly folded (non-stable or non-trimeric) Glycoprotein, increased trimer percentage and/or trimer yield are considered indicative of stable, native, correctly folded Glycoprotein.

The family Filoviridae is the taxonomic home of several related viruses (filoviruses or filovirids) that form filamentous infectious viral particles (virions), and encode their genome in the form of single-stranded negative-sense RNA. Two members of the family that are commonly known are Ebola virus and Marburg virus. The first strain of Marburgvirus was discovered in 1967, when it was transported with imported monkeys to Marburg, Germany, and caused a fatal outbreak. The first strain of Ebolavirus was discovered in 1976, taking its name from the Ebola River in the northern Congo basin of Central Africa, where it first appeared. Type species include the Marburg type Lake Victoria marburgvirus and the Ebola type Zaire ebolavirus. Four other Ebola species have been characterized: Reston ebolavirus, Sudan ebolavirus, Tal Forest ebolavirus, and Bundibugyo ebolavirus. The Zaire ebolavirus (ZEBOV) subtype has proved the most-deadly to the population of Central and West Africa with three major outbreak variants. The 1976 outbreak variant Mayinga was responsible for 380 cases with 218 fatalities (88% case-fatality rate (CFR)), and the 1995 Kikwit variant caused 315 cases with 250 mortalities (81% CFR). The 2013-2016 West African outbreak of the Ebola virus had 28, 616 confirmed cases and 11, 310 deaths.

In one general aspect, the invention relates to a recombinant Filovirus GP. The term "recombinant" when used with reference to a protein refers to a protein that is produced by a recombinant technique or by chemical synthesis in vitro. According to embodiments of the invention, a "recombinant" protein has an artificial amino acid sequence in that it contains at least one sequence element (e.g., amino acid substitution, deletion, addition, sequence replacement, etc.) that is not found in the corresponding naturally occurring sequence. Preferably, a "recombinant" protein is a non-naturally occurring Filovirus glycoprotein that is optimized to induce an immune response or produce an immunity against one or more naturally occurring Filovirus strains.

The terms "Filovirus glycoprotein," "Filovirus GP," and "GP" refer to a glycoprotein, or a fragment or derivative thereof, that is in nature expressed on the envelope of the Filovirus virion and enables a Filovirus to target and attach to the plasma membrane of Filovirus infected cells.

According to embodiments of the invention, a "Filovirus GP protein" can be an ectodomain (amino acids 1-647) of a wild-type Zaire ebolavirus glycoprotein, for e.g. from the Mayinga, Makona or Kikwit variant. An ectodomain of a wild-type Zaire ebolavirus glycoprotein is a glycoprotein that has been truncated in order to remove the transmembrane region of the GP. Ectodomains are soluble and therefore easier to manipulate and to test for stability.

According to embodiments of the invention, a "Filovirus GP protein" can also be an ectodomain (amino acid 1-647) of a wild-type Zaire ebolavirus glycoprotein having a deleted mucin-like domain. The mucin-like domain forms a separate domain that dangle at the sides of each protomer. This domain is heavily glycosylated and there are not a lot of neutralizing antibodies directed against it. Ebola GP lacking the mucin-like domain forms prefusion trimers, which are easier to analyze and characterize than GPs that contain the mucin-like domain. For the Mayinga Δmucin GP, amino acids 320 until 476 of the GP were deleted. For the Makona and Kikwit Δmucin GP, amino acids 314 until 472 were deleted.

According to embodiments of the invention, a "Filovirus GP protein" can be an ectodomain of the Filovirus GP protein having a C-terminal tag, such as a His6 tag.

According to embodiments of the invention, an "Filovirus glycoprotein" can be a trimer or a monomer, and is preferably a trimer. The trimer can be a homotrimer (e.g., trimers comprising three identical polypeptide units) or a heterotrimer (e.g., trimers comprising three polypeptide units that are not all identical). Preferably, the trimer is a homotrimer.

A "Filovirus glycoprotein" can be a soluble protein, or a membrane bound protein. Membrane bound envelope proteins typically comprise a transmembrane domain, such as in the full-length Filovirus glycoprotein comprising a transmembrane domain (TM) as shown in FIG. 1. Membrane bound proteins can have a cytoplasmic domain, but do not require a cytoplasmic domain to be membrane bound. Soluble envelope proteins comprise at least a partial or a complete deletion of the transmembrane domain. For instance, the C-terminal end of a full-length Filovirus glycoprotein can be truncated to delete the transmembrane domain, thereby producing a soluble protein, as shown in FIG. 1. However, the Filovirus glycoprotein can still be soluble with shorter truncations and alternative truncation positions. Membrane-bound glycoprotein according to the invention may comprise a complete or a partial C-terminal domain as compared to a native glycoprotein.

A signal peptide is typically present at the N-terminus of the Filovirus GP when expressed but is cleaved off by signal peptidase and thus is not present in the mature protein. The signal peptide can be interchanged with other signal sequences, and some non-limiting examples of signal peptides are provided herein as SEQ ID NOs: 44 (signal peptide of Ebola GP) and 45 (signal peptide of Marburg GP).

According to embodiments of the invention, the Filovirus glycoprotein can be derived from a Filovirus glycoprotein sequence from any Ebola or Marburg strain such as e.g. Mayinga, Makona, Kikwit, Sudan Gulu, Marburg, etc. or combinations thereof. The Filovirus glycoprotein sequence can be a naturally occurring sequence, a consensus sequence, a synthetic sequence, or any derivative or fragment thereof. As used herein "consensus sequence" means an artificial sequence of amino acids based on an alignment of amino acid sequences of homologous proteins, e.g. as determined by an alignment of amino acid sequences of homologous proteins. A "synthetic sequence" is a non-naturally occurring Filovirus glycoprotein that is optimized to induce an immune response or produce immunity against more than one naturally occurring Filovirus strain.

In preferred embodiments of the invention, the Filovirus GP is a naturally occurring glycoprotein, a consensus glycoprotein, or a synthetic glycoprotein, having a non-charged amino acid residue, at position 588, wherein the numbering of the positions is according to the numbering of the GP in Z/Zaire/Yambuku/1976/057935 (SEQ ID NO:1) and wherein the non-charged amino acid residue in not a cysteine. Particularly preferred are Glycoproteins wherein the non-charged amino acid residue is a hydrophobic amino acid residue selected from the group of F, I, A, L, M, V, W and Y. Even more preferred are glycoproteins wherein the hydrophobic amino acid residue is selected from the group of F, I, V and W. Most preferred are glycoproteins wherein the hydrophobic amino acid residue is F.

In certain embodiments of the invention, a Filovirus glycoprotein, whether a naturally occurring sequence, consensus sequence, synthetic sequence etc., further comprising an amino acid residue P at position 577 and/or 579, wherein the numbering of the positions is according to the numbering of the GP in Z/Zaire/Yambuku/1976/057935.

The amino acid sequence of the Filovirus glycoprotein into which one or more desirable amino acid (or indicated amino acid) substitutions at the one or more indicated positions are introduced is referred to as the "backbone Filovirus GP sequence" or "parent Filovirus GP sequence." For example, if position 588 in the "Mayinga GP-647, delta mucin-like domain" (i.e. the GP ectodomain having a 320-476 a.a. deletion) sequence of SEQ ID NO: 6 is mutated to F, then the "Mayinga GP-647, delta mucin-like domain" sequence is considered to be the "backbone" or "parent" sequence. Any Filovirus glycoprotein can be used as the "backbone" or "parent" sequence into which a novel stabilizing mutation according to an embodiment of the invention can be introduced, either alone or in combination with other mutations, such as the mutations at positions 577 or 579.

Non-limiting examples of Filovirus GP that could be used as backbone include Filovirus GP from a natural Filovirus isolate, a synthetic Filovirus GP, or a consensus Filovirus GP, and in certain non-limiting examples include those comprising SEQ ID NO: 2-42.

In preferred embodiments of the invention, the backbone Filovirus glycoprotein is selected from the group consisting of:

1) a Zaire Ebolavirus Mayinga glycoprotein comprising the amino acid sequence of SEQ ID NO: 2 or a Zaire Ebolavirus Mayinga glycoprotein with a deletion between amino acid residues 320 until 476, comprising the amino acid sequence of SEQ ID NO: 6; and
2) a Zaire Ebolavirus Makona GP glycoprotein comprising the amino acid sequence of SEQ ID NO: 10 or a Zaire Ebolavirus Makona GP glycoprotein with a deletion between amino acid residues 314 until 472, comprising the amino acid sequence of SEQ ID NO: 14; and
3) a Zaire Ebolavirus Kikwit glycoprotein comprising the amino acid sequence of SEQ ID NO: 19 or a Zaire Ebolavirus Kikwit glycoprotein with a deletion between amino acid residues 314 until 472, comprising the amino acid sequence of SEQ ID NO: 23; and
4) a Marburg glycoprotein with a deletion between amino acid residues 255 until 423, comprising the amino acid sequence of SEQ ID NO: 27,
   wherein the numbering of the positions is according to the numbering of the GP in Z/Zaire/Yambuku/1976/057935.

According to embodiments of the invention, a recombinant Filovirus GP has at least one of (a) an improved percentage of trimer formation and (b) an improved trimer yield compared to an Filovirus GP not having the indicated amino acid residues at position 588.

As used herein "improved percentage of trimer formation" means that a greater percentage of trimer is formed when the backbone sequence of the Filovirus glycoprotein contains one or more of the amino acid substitutions of the invention as compared to the percentage of trimer that is formed when the backbone sequence of the Filovirus GP sequence does not contain such amino acid substitutions. As used herein "improved trimer yield" means that a greater total amount of the trimer form of the envelope protein is obtained when the backbone sequence of the Filovirus glycoprotein contains one or more of the amino acid substitutions of the invention as compared to the total amount of trimer form of the envelope protein that is obtained when the backbone sequence of the Filovirus GP sequence does not contain such amino acid substitutions.

Trimer formation can be measured by an antibody binding assay using antibodies that bind specifically to the trimer form of the Filovirus GP. Examples of trimer specific antibodies that can be used to detect the trimer form include, but are not limited to, the monoclonal antibody (mAb): Mab 100. Any antibody binding assay known in the art in view of the present disclosure can be used to measure the percentage of trimer formation of a recombinant Filovirus GP of the invention, such as ELISA, Bio Layer Interferometry, etc.

In a particular embodiment, trimer formation is measured by BioLayer Interferometry (BLI) "Antibody 100 was immobilized on anti-hIgG (AHC) sensors (FortéBio cat #18-5060) at a concentration of 10 μg/ml in 1× kinetics buffer (FortéBio cat #18-1092) in 96-half well black flat bottom polypylene microplates (FortéBio cat #3694). The experiment was performed on an Octet HTX instrument (Pall-FortéBio) at 30° C. shaking speed 1,000 rpm. Activation was 60 seconds, immobilization of antibodies 600 seconds, then washing 150 seconds and then binding the Envs 600 seconds, followed by a dissociation of 60 seconds, all shaking at 1,000 rpm. The data analysis was performed using the FortéBio Data Analysis 8.1 software (FortéBio). The binding slope was determined at 10 seconds in nm/minute."

AlphaLISA is a bead-based proximity assay in which singlet oxygen molecules, generated by high energy irradiation of donor beads, are transferred to acceptor beads that are within a distance of approximately 200 nm with respect to the donor beads. The transfer of singlet oxygen molecules to the acceptor beads initiates a cascading series of chemical reactions resulting in a chemiluminescent signal that can then be detected (Eglen et al. *Curr. Chem. Genomics*, 2008, 25(1): 2-10). For example, recombinant Filovirus glycoproteins labeled with a Flag-His tag can be incubated with 2 different beads that are conjugated to Nickel or antibody that can bind GP simultaneously. For a trimer—specific assay, the donor bead is conjugated to a trimer-specific Mab 100 and the acceptor bead is conjugated to Nickel that binds the His6 tag or an anti-His antibody. For quantification of GP, the donor bead is conjugated to anti-Flag antibody and the acceptor bead to Nickel or the anti-His antibody. The amount of trimer formed can be determined by measuring the chemiluminescent signal generated from the pair of donor beads conjugated to the antibody that binds to the trimer specific mAb and the acceptor beads conjugated to the anti-His antibody. The total amount of Filovirus glycoprotein expressed can be determined by measuring the chemiluminescent signal generated from the pair of nickel-conjugated donor beads and anti-Flag-conjugated acceptor beads. For example, the amount of trimer and the total envelope protein expressed can be measured by an AlphaLISA assay as described in detail in Example 3. The percentage of trimer formation can be calculated by dividing the amount of trimer formed by the total amount of expressed envelope protein.

The amount of trimer formed and the total amount of envelope protein expressed can also be determined using chromatographic techniques that are capable of separating the trimer form from other forms of the Filovirus glycoprotein, e.g., the monomer form. Examples of such techniques that can be used include but are not limited to analytical size exclusion chromatography (SEC). According to certain embodiments, the percentage of trimer formation is determined using analytical SEC. According to certain embodiments, the trimer yield is determined using analytical SEC.

Nucleic Acid, Vectors, and Cells

In another general aspect, the invention provides a nucleic acid molecule encoding a recombinant Filovirus GP according to the invention, and a vector comprising the nucleic acid molecule. The nucleic acid molecules of the invention can be in the form of RNA or in the form of DNA obtained by cloning or produced synthetically. The DNA can be double-stranded or single-stranded. The DNA can for example comprise cDNA, genomic DNA, or combinations thereof. The nucleic acid molecules and vectors can be used for recombinant protein production, expression of the protein in a host cell, or the production of viral particles.

According to embodiments of the invention, the nucleic acid encoding the recombinant Filovirus glycoprotein is operably linked to a promoter, meaning that the nucleic acid is under the control of a promoter. The promoter can be a homologous promoter (i.e., derived from the same genetic source as the vector) or a heterologous promoter (i.e., derived from a different vector or genetic source). Examples of suitable promoters include the human cytomegalovirus immediate early (hCMV IE, or shortly "CMV") promoter and the Rous Sarcoma virus (RSV) promoter. Preferably, the promoter is located upstream of the nucleic acid within an expression cassette.

According to embodiments of the invention, a vector can be an expression vector. Expression vectors include, but are not limited to, vectors for recombinant protein expression and vectors for delivery of nucleic acid into a subject for expression in a tissue of the subject, such as a viral vector. Examples of viral vectors suitable for use with the invention include, but are not limited to adenoviral vectors, adeno-associated virus vectors, pox virus vectors, Modified Vaccinia Ankara (MVA) vectors, enteric virus vectors, Venezuelan Equine Encephalitis virus vectors, Semliki Forest Virus vectors, Tobacco Mosaic Virus vectors, lentiviral vectors, etc. The vector can also be a non-viral vector. Examples of non-viral vectors include, but are not limited to plasmids, bacterial artificial chromosomes, yeast artificial chromosomes, bacteriophages, etc.

In certain embodiments of the invention, the vector is an adenovirus vector, e.g., a recombinant adenovirus vector. A recombinant adenovirus vector may for instance be derived from a human adenovirus (HAdV, or AdHu), or a simian adenovirus such as chimpanzee or gorilla adenovirus (ChAd, AdCh, or SAdV) or rhesus adenovirus (rhAd). Preferably, an adenovirus vector is a recombinant human adenovirus vector, for instance a recombinant human adenovirus serotype 26, or any one of recombinant human adenovirus serotype 5, 4, 35, 7, 48, etc. In other embodiments, an adenovirus vector is a rhAd vector, e.g. rhAd51, rhAd52 or rhAd53.

The preparation of recombinant adenoviral vectors is well known in the art. For example, preparation of recombinant adenovirus 26 vectors is described, in, e.g., WO 2007/104792 and in Abbink et al., (2007) *Virol.* 81(9): 4654-63. Exemplary genome sequences of adenovirus 26 are found in GenBank Accession EF 153474 and in SEQ ID NO: 1 of WO 2007/104792. Exemplary genome sequences for rhAd51, rhAd52 and rhAd53 are provided in US 2015/0291935.

According to embodiments of the invention, any of the recombinant Filovirus GPs described herein can be expressed and/or encoded by any of the vectors described herein. In view of the degeneracy of the genetic code, the skilled person is well aware that several nucleic acid sequences can be designed that encode the same protein, according to methods entirely routine in the art. The nucleic acid encoding the recombinant Filovirus GP of the invention can optionally be codon-optimized to ensure proper expression in the host cell (e.g., bacterial or mammalian cells). Codon-optimization is a technology widely applied in the art.

The invention also provides cells, preferably isolated cells, comprising any of the nucleic acid molecules and vectors described herein. The cells can for instance be used for recombinant protein production, or for the production of viral particles.

Embodiments of the invention thus also relate to a method of making a recombinant Filovirus GP. The method comprises transfecting a host cell with an expression vector comprising nucleic acid encoding a recombinant Filovirus GP according to an embodiment of the invention operably linked to a promoter, growing the transfected cell under conditions suitable for expression of the recombinant Filovirus GP, and optionally purifying or isolating the recombinant Filovirus GP expressed in the cell. The recombinant Filovirus GP can be isolated or collected from the cell by any method known in the art including affinity chromatography, size exclusion chromatography, etc. Techniques used for recombinant protein expression will be well known to one of ordinary skill in the art in view of the present disclosure. The expressed recombinant Filovirus GP can also be studied without purifying or isolating the expressed protein, e.g., by analyzing the supernatant of cells transfected with an expression vector encoding the recombinant Filovirus GP and grown under conditions suitable for expression of the Filovirus GP.

In a preferred embodiment, the expressed recombinant Filovirus GP is purified under conditions that permit association of the protein so as to form the stabilized trimeric complex. For example, mammalian cells transfected with an expression vector encoding the recombinant Filovirus GP operably linked to a promoter (e.g. CMV promoter) can be cultured at 33-39° C., e.g. 37° C., and 2-12% $CO_2$, e.g. 8% $CO_2$. Expression can also be performed in alternative expression systems such as insect cells or yeast cells, all conventional in the art. The expressed Filovirus GP can then be isolated from the cell culture for instance by lectin affinity chromatography, which binds glycoproteins. The Filovirus GP bound to the column can be eluted with mannopyranoside. The Filovirus GP eluted from the column can be subjected to further purification steps, such as size exclusion chromatography, as needed, to remove any residual contaminants, e.g., cellular contaminants. Alternative purification methods, non-limiting examples including antibody affinity chromatography, negative selection with non-bNAbs, anti-tag purification, or other chromatography methods such as ion exchange chromatography etc, as well as other methods known in the art, could also be used to isolate the expressed Filovirus GP.

The nucleic acid molecules and expression vectors encoding the recombinant Filovirus GPs of the invention can be made by any method known in the art in view of the present disclosure. For example, nucleic acid encoding the recombinant Filovirus GP can be prepared by introducing at least one of the amino acid substitutions at the indicated positions into the backbone Filovirus GP sequence using genetic engineering technology and molecular biology techniques, e.g., site directed mutagenesis, polymerase chain reaction (PCR), etc., which are well known to those skilled in the art. The nucleic acid molecule can then be introduced or "cloned" into an expression vector also using standard molecular biology techniques. The recombinant Filovirus glycoprotein can then be expressed from the expression vector in a host cell, and the expressed protein purified from the cell culture by any method known in the art in view of the present disclosure.

Trimeric Complex

In another general aspect, the invention relates to a trimeric complex comprising a noncovalent oligomer of three of the recombinant Filovirus GPs according to the invention. The trimeric complex can comprise any of the recombinant Filovirus GPs described herein. Preferably the trimeric complex comprises three identical monomers of the recombinant Filovirus GPs according to the invention. The trimeric complex can be separated from other forms of the Filovirus glycoprotein, such as the monomer form, or the trimeric complex can be present together with other forms of the Filovirus glycoprotein, such as the monomer form.

Compositions and Methods

In another general aspect, the invention relates to a composition comprising a recombinant Filovirus GP, trimeric complex, isolated nucleic acid, vector, or host cell, and a pharmaceutically acceptable carrier. The composition can comprise any of the recombinant Filovirus GPs, trimeric complexes, isolated nucleic acid molecules, vectors, or host cells described herein.

A carrier can include one or more pharmaceutically acceptable excipients such as binders, disintegrants, swelling agents, suspending agents, emulsifying agents, wetting agents, lubricants, flavorants, sweeteners, preservatives, dyes, solubilizers and coatings. The precise nature of the carrier or other material can depend on the route of administration, e.g., intramuscular, intradermal, subcutaneous, oral, intravenous, cutaneous, intramucosal (e.g., gut), intranasal or intraperitoneal routes. For liquid injectable preparations, for example, suspensions and solutions, suitable carriers and additives include water, glycols, oils, alcohols, preservatives, coloring agents and the like. For solid oral preparations, for example, powders, capsules, caplets, gel caps and tablets, suitable carriers and additives include starches, sugars, diluents, granulating agents, lubricants, binders, disintegrating agents and the like. For nasal sprays/inhalant mixtures, the aqueous solution/suspension can comprise water, glycols, oils, emollients, stabilizers, wetting agents, preservatives, aromatics, flavors, and the like as suitable carriers and additives.

Compositions of the invention can be formulated in any matter suitable for administration to a subject to facilitate administration and improve efficacy, including, but not limited to, oral (enteral) administration and parenteral injections. The parenteral injections include intravenous injection or infusion, subcutaneous injection, intradermal injection, and intramuscular injection. Compositions of the invention can also be formulated for other routes of administration including transmucosal, ocular, rectal, long acting implantation, sublingual administration, under the tongue, from oral mucosa bypassing the portal circulation, inhalation, or intranasal.

Embodiments of the invention also relate to methods of making the composition. According to embodiments of the invention, a method of producing a composition comprises mixing a recombinant Filovirus GP, trimeric complex, isolated nucleic acid, vector, or host cell of the invention with one or more pharmaceutically acceptable carriers. One of ordinary skill in the art will be familiar with conventional techniques used to prepare such compositions.

Filovirus antigens (e.g., proteins or fragments thereof derived from Filovirus glycoprotein gene products) and vectors, such as viral vectors, expressing the Filovirus antigens have previously been used in immunogenic compositions and vaccines for vaccinating a subject against a Filovirus infection, or for generating an immune response against a Filovirus infection in a subject. As used herein, "subject" means any animal, preferably a mammal, most preferably a human, to who will be or has been administered an immunogenic composition according to embodiments of the invention. The term "mammal" as used herein, encompasses any mammal. Examples of mammals include, but are not limited to, mice, rats, rabbits, guinea pigs, monkeys, humans, etc., preferably a human. The recombinant Filovirus GPs of the invention can also be used as antigens to induce an immune response against a Filovirus in a subject in need thereof. The immune response can be against one or more Filovirus variants, such as Ebola Zaire Mayinga, Kikwit and Makona, or a Marburg virus. The compositions can comprise a vector from which the recombinant Filovirus GP is expressed, or the composition can comprise an isolated recombinant Filovirus GP according to an embodiment of the invention.

For example, compositions comprising a recombinant Filovirus protein or a trimeric complex thereof can be administered to a subject in need thereof to induce an immune response against a Filovirus infection in the subject. A composition comprising a vector, such as an adenovirus vector, encoding a recombinant Filovirus GP of the invention, wherein the recombinant Filovirus GP is expressed by the vector, can also be administered to a subject in need thereof to induce an immune response against a Filovirus infection in the subject. The methods described herein also include administering a composition of the invention in combination with one or more additional Filovirus GPs that are preferably expressed from one or more vectors, such as adenovirus vectors or MVA vectors, including methods of priming and boosting an immune response.

In certain embodiments, the Filovirus GP can be displayed on a particle, such as a liposome, virus-like particle (VLP), nanoparticle, virosome, or exosome, optionally in combination with endogenous and/or exogenous adjuvants. When compared to soluble or monomeric Glycoprotein on its own, such particles typically display enhanced efficacy of antigen presentation in vivo.

Examples of VLPs that display Filovirus GP can be prepared e.g. by co-expressing the Filovirus GP with self-assembling viral proteins. VLPs resemble viruses but are non-infectious because they contain no viral genetic material. The expression of viral structural proteins, such as envelope or capsid, can result in self-assembly of VLPs. VLPs are well known to the skilled person, and their use in vaccines is for instance described in (Kushnir et al., Vaccine. 2012 Dec. 17; 31(1): 58-83).

In certain preferred embodiments, the particle is a liposome. A liposome is a spherical vesicle having at least one lipid bilayer. The Filovirus GP trimer proteins can for instance be non-covalently coupled to such liposomes by electrostatic interactions, e.g. by adding a His-tag to the C-terminus of the Filovirus GP trimer and a bivalent chelating atom such as $Ni^{2+}$ or $Co^{2+}$ incorporated into the head group of derivatized lipids in the liposome. In certain non-limiting and exemplary embodiments, the liposome comprises 1,2-distearoyl-sn-glycero-3-phosphocholine (DSPC), cholesterol, and the Nickel or Cobalt salt of 1,2-dioleoyl-sn-glycero-3-[N-(5-amino-1-carboxypentyl)iminodiacetic acid)succinyl] (DGS-NTA($Ni^{2+}$) or DGS-NTA ($Co^{2+}$)) at 60:36:4 molar ratio. In preferred embodiments, the Filovirus GP trimer proteins are covalently coupled to the liposomal surface, e.g. via a maleimide functional group integrated in the liposome surface. In certain non-limiting exemplary embodiments thereof, the liposome comprises DSPC, cholesterol, and 1,2-dipalmitoyl-sn-glycero-3-phosphoethanolamine-N-[4-(p-maleimidomethyl)cyclohexane-carboxamide] lipid in a molar ratio of 54:30:16. The Filovirus GP can be coupled thereto e.g. via an added C-terminal cysteine in the Filovirus GP. The covalently coupled variants are more stable, elicit high antigen specific IgG titers and epitopes at the antigenically less relevant 'bottom' of the Env trimer are masked. Methods for preparing Filovirus GP trimers coupled to liposomes, as well as their characterization, are known and have for instance been described in (Bale et al, J Virol. 2017 Jul. 27; 91(16). pii: e00443-17), incorporated by reference herein. The invention also provides an Filovirus GP of the invention fused to and/or displayed on a liposome.

In certain embodiments, a Filovirus GP of the invention is fused to self-assembling particles, or displayed on nanoparticles. Antigen nanoparticles are assemblies of polypeptides that present multiple copies of antigens, e.g. the Filovirus GP of the instant invention, which result in multiple binding sites (avidity) and can provide improved antigen stability and immunogenicity. Preparation and use of self-assembling protein nanoparticles for use in vaccines is well-known to the skilled person, see e.g. (Zhao L, et al (2014) Vaccine 32: 327-337), (López-Sagaseta et al, Comput Struct Biotechnol J. 2015 Nov. 26; 14:58-68). As non-limiting examples, self-assembling nanoparticles can be based on ferritin, bacterioferritin, or DPS. DPS nanoparticles displaying proteins on their surface are for instance described in WO2011/082087. Other self-assembling protein nanoparticles as well as preparation thereof, are for instance disclosed in WO 2014/124301, and US 2016/0122392, incorporated by reference herein. The invention also provides a Filovirus GP of the invention fused to and/or displayed on a self-assembling nanoparticle. The invention also provides compositions comprising VLPs, liposomes, or self-assembling nanoparticles according to the invention.

In certain embodiments, an adjuvant is included in a composition of the invention or co-administered with a composition of the invention. Use of adjuvant is optional, and may further enhance immune responses when the composition is used for vaccination purposes. Adjuvants suitable for co-administration or inclusion in compositions in accordance with the invention should preferably be ones that are potentially safe, well tolerated and effective in people. Such adjuvants are well known to the skilled person, and non-limiting examples include QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Aluminium salts such as Aluminium Phosphate (e.g. AdjuPhos) or Aluminium Hydroxide, and MF59.

Other aspects of the invention relate to recombinant Filovirus glycoproteins comprising an amino acid sequence selected from the group of SEQ ID NO: 2, SEQ ID NO: 6, SEQ ID NO: 10, SEQ ID NO: 14, SEQ ID NO: 19, SEQ ID NO: 23 and SEQ ID NO: 27. These Filovirus GPs can in certain embodiments be used as backbone proteins, wherein the mutations described above can be made to obtain a molecule of the invention. Isolated nucleic acid molecules encoding these sequences, vectors comprising these sequences operably linked to a promoter, and compositions comprising the protein, isolated nucleic acid molecule, or vector are also contemplated by the invention.

EMBODIMENTS

Embodiment 1 is a recombinant Filovirus glycoprotein, comprising a non-charged amino acid residue, at position 588, wherein the numbering of the positions is according to the numbering of the GP in Z/Zaire/Yambuku/1976/057935 and wherein the non-charged amino acid residue in not a cysteine.

Embodiment 2 is a recombinant Filovirus glycoprotein according to embodiment 1, wherein the non-charged amino acid residue is a hydrophobic amino acid residue selected from the group of F, I, A, L, M, V, W and Y.

Embodiment 3 is a recombinant Filovirus glycoprotein according to embodiment 2, wherein the hydrophobic amino acid residue is selected from the group of F, I, L, M, V, and Y.

Embodiment 4 is a recombinant Filovirus glycoprotein according to claim 3, wherein the hydrophobic amino acid residue is F.

Embodiment 5 is a recombinant Filovirus glycoprotein according to any one of embodiments 1-4, further comprising an amino acid residue P at position 577 and/or 579, wherein the numbering of the positions is according to the numbering of the GP in Z/Zaire/Yambuku/1976/057935.

Embodiment 6 is a recombinant Filovirus glycoprotein according to any one of embodiments 1-5, wherein the Filovirus is from a strain selected from the group of Mayinga, Makona, kikwit, Sudan Gulu and Marburg.

Embodiment 7 is a recombinant Filovirus glycoprotein according to anyone of embodiments 1-6, wherein the Filovirus glycoprotein is selected from the group consisting of:

1) a Zaire Ebolavirus Mayinga glycoprotein comprising the amino acid sequence of SEQ ID NO: 2 or a Zaire Ebolavirus Mayinga glycoprotein with a deletion between amino acid residues 320 until 476, comprising the amino acid sequence of SEQ ID NO: 6; and 2) a Zaire Ebolavirus Makona GP glycoprotein comprising the amino acid sequence of SEQ ID NO: 10 or a Zaire Ebolavirus Makona GP glycoprotein with a deletion between amino acid residues 314 until 472, comprising the amino acid sequence of SEQ ID NO: 14; and 3) a Zaire Ebolavirus Kikwit glycoprotein comprising the amino acid sequence of SEQ ID NO: 19 or a Zaire Ebolavirus Kikwit glycoprotein with a deletion between amino acid residues 314 until 472, comprising the amino acid sequence of SEQ ID NO: 23; and 4) a Marburg glycoprotein with a deletion between amino acid residues 255 until 423, comprising the amino acid sequence of SEQ ID NO: 27 wherein the numbering of the positions is according to the numbering of the GP in Z/Zaire/Yambuku/1976/057935.

Embodiment 8 is a recombinant Filovirus glycoprotein of any of embodiments 1 to 7, comprising an amino acid sequence selected from the group of SEQ ID NO: 2-42.

Embodiment 9 is a trimeric complex comprising a non-covalent oligomer of three of the recombinant Filovirus glycoproteins of any of embodiments 1 to 7.

Embodiment 10 is a particle, preferably a nanoparticle, displaying on its surface the recombinant Filovirus glycoprotein of any of embodiments 1 to 7, or the trimeric complex of embodiment 8.

Embodiment 11 is an isolated nucleic acid molecule encoding the recombinant Filovirus glycoprotein of any of embodiments 1 to 7.

Embodiment 12 is a vector comprising the isolated nucleic acid molecule of embodiment 11 operably linked to a promoter.

Embodiment 13 is the vector of embodiment 12, wherein the vector is an adenovirus vector.

Embodiment 14 is a host cell comprising the isolated nucleic acid molecule of embodiment 11 or the vector of embodiment 12 or 13.

Embodiment 15 is a method of producing a recombinant Filovirus glycoprotein, comprising growing the host cell of embodiment 14 under conditions suitable for production of the recombinant Filovirus glycoprotein.

Embodiment 16 is a composition comprising the recombinant Filovirus glycoprotein of any of embodiments 1 to 8, the trimeric complex of claim 9, the particle of claim 10, the isolated nucleic acid molecule of claim 11, or the vector of claim 12 or 13, and a pharmaceutically acceptable carrier.

Embodiment 17 is a method of improving the trimer formation of a Filovirus glycoprotein, the method comprising substituting the amino acid residue at position 588 of the glycoprotein for a non-charged amino acid residue, wherein the numbering of the positions is according to the numbering of the GP in Z/Zaire/Yambuku/1976/057935, and wherein the non-charged amino acid residue in not a cysteine.

Embodiment 18 is a method according to embodiment 17, the method further comprising substituting the amino acid residue at position 577 and/or 579 of the glycoprotein for a P residue, wherein the numbering of the positions is according to the numbering of the GP in Z/Zaire/Yambuku/1976/057935.

EXAMPLES

Example 1: Expression and Purification of Recombinant Ebola and Marburg Glycoproteins (GP)

The ectodomains (i.e. amino acid residues 1-647) of recombinant Ebola and Marburg GPs were expressed and purified as soluble proteins, with or without the mucin-like domain. Subsequently, single mutations (amino acid substitutions) and combinations thereof (e.g. double and triple mutations) were introduced into the following different backbone sequences: Mayinga GP (SEQ ID NO: 2), Kikwit GP (SEQ ID NO: 19), EBOV14 GP a.k.a. Makona, which is identical to the consensus of the outbreak strains of 2014 (SEQ ID NO: 10), MARV GP (Marburg) (SEQ ID NO: 41), Mayinga Δmucin GP (SEQ ID NO: 6), Kikwit Δmucin GP (SEQ ID NO: 23), EBOV14 Δmucin GP (SEQ ID NO: 14), and MARV Δmucin GP (SEQ ID NO: 27).

Generation and Expression of Ebola and Marburg glycoprotein Constructs and Variants DNA encoding the glycoproteins (GPs) shown in SEQ ID NO: 2-42 were synthesized and codon-optimized for expression in human cells at GenScript (Piscataway, N.J. 08854). The codon-optimized sequences were then cloned into the vector pcDNA2004 to generate the GP constructs, which were used as the backbone sequences for introducing further mutations. The genes were expressed in Expi293F cells (Thermo Fischer) according to manufacturer's specification. Glucose levels were monitored using the ViCell MetaFlex (Beckmann). Glucose was depleted at day 4 post-transfection and therefore glucose was added at a 15 mM concentration. Transfections were harvested at day 6 post-transfection by centrifugation and sterile filtration.

Purification of Ebola or Marburg GP Protein

Interfering host-cell-proteins (HCP's) were scavenged by applying the supernatant on 13 mL CHT type 1 resin (Biorad) in an XK16/20 column (GEHC) using a flow speed of 300 cm/hr. and a running buffer of 5 mM NaPO4, pH 6.8. Bound proteins were eluted, by a step elution, using 500 mM NaPO4, pH 7.4. The, HCP depleted, flow through was subsequently applied on a HisTrap HP 5 mL, affinity chromatography column selective for His-tagged proteinsusing a flow speed of 300 cm/hr. and a running buffer of 20 mM Tris, 500 mM NaCl pH 7.4. Bound proteins were eluted using a step-gradient of 15, 30 and 100% elution buffer (20 mM Tris, 500 mM NaCl, 300 mM Imidazole pH7.4) whilst running the column in upflow and a flow of 600 cm/hr. The trimer fractions eluted when 100 mM Imidazole is applied along with aggregates. This fraction was concentrated, using 50K Amicon Ultra concentrators (Millipore), and applied to a Superdex 16/600 size exclusion column (GEHC) using a flow of 60 cm/hr. The trimer fraction was subsequently separated from aggregates and monomers. The fractions containing the trimer peak were pooled, and the identity of the peak confirmed as GP protein using Western blot and SDS-PAGE, and/or analytical SEC analysis. The concentration of the purified Ebola or Marburg GP was determined by measuring the optical density at 280 nm, and the purified protein was stored at 4° C. until further use.

Example 2: Improved Expression and Stability of Soluble Ebola GP Trimers

Several Ebola glycoprotein (GP) sequences were selected as the backbone sequence for studying the effects of various mutations on trimer formation of the Ebola GPs. The ectodomains (amino acids 1-647, extended with a His6 tag) of wild-type Zaire ebolavirus glycoproteins (Mayinga, Makona and Kikwit) were expressed in expi293F cells. For each of the three GPs, also variants were made that lacked the mucin-like domain. The mucin-like domain forms a separate peripheral domain on each protomer. This domain is more variable, heavily glycosylated and there are not a lot of neutralizing antibodies directed against it. Ebola GPs lacking the mucin-like domain form prefusion trimers that are easier to analyze and characterize than GPs that contain the heterogenous mucin-like domain. For the Mayinga protein: amino acids 320 until 476 have been deleted. For the Makona and Kikwit: amino acids 314 until 472 have been deleted. The delta mucin-like GPs have been crystallized and are considered to be potential vaccine candidates. NativePAGE and SEC-MALS on crude supernatants revealed that the major species that are produced are monomers, whereas only a minor fraction is trimeric. Soluble Ebola proteins having an increased percentage of trimer formation and absolute higher trimer yields are advantageous from a manufacturing perspective, because less purification and removal of the envelope protein present in the preparation in the undesired non-native conformations will be required. Moreover, they will be better vector inserts.

The recombinant GP protein variants were tested for trimer formation to identify those mutations that improved the percentage of trimer formation and/or improved trimer yields relative to the backbone sequences. Initially, semi-high throughput screening of trimer percentage and trimer yields was conducted using a NativePAGE analysis with cell supernatant loaded on gel. The results of the NativePAGE were confirmed by analytical size exclusion (SEC) using cell supernatants.

NativePAGE Analysis

Figure 2:
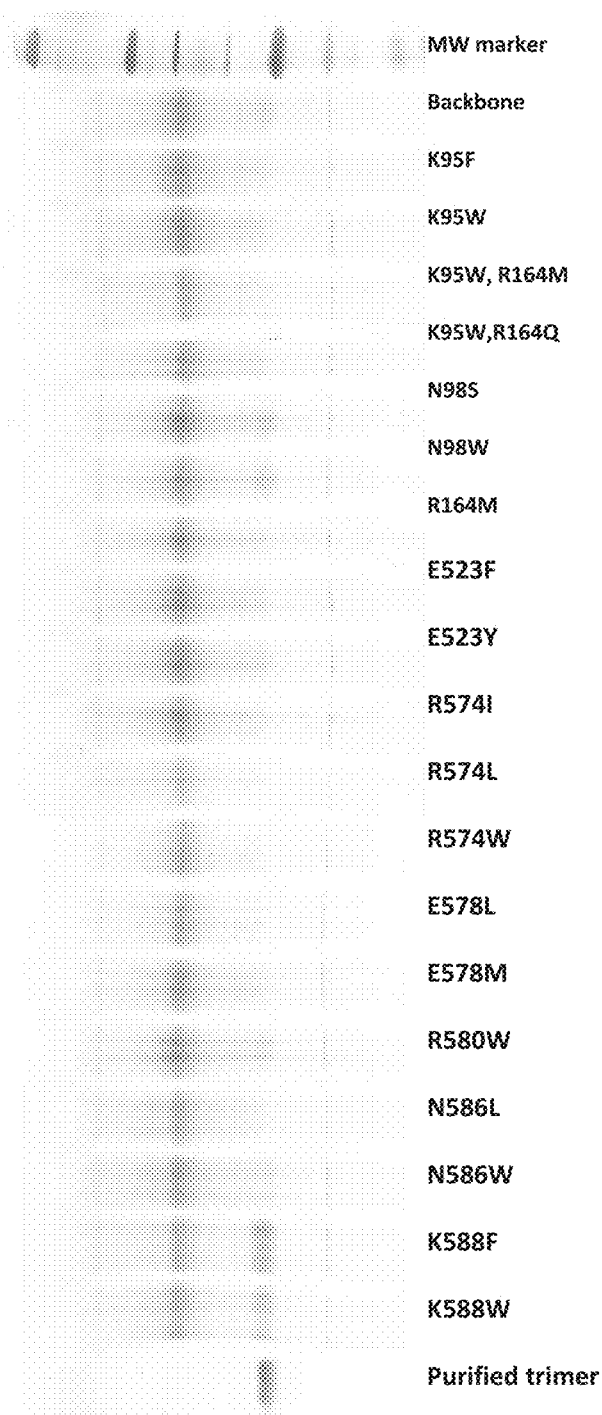
FIG. 2. Blue NativePAGE with Makona Δmucin-like GP-T577P-T42A (FIL161615) backbone and mutants. All lanes contain cell supernatants, except for the last lane which contains purified trimers indicating at what height the trimer runs.

NativePAGE was performed according to manufacturer's protocol (LifeTechnologies) using 4-16% NativePage Bis-Tris gradient gels (LifeTechnologies). The GP trimer with mucin-like domain runs at a mass of about 800 kDa, whereas the GP without the mucin-like domain runs at a mass of about 420 kDa. Initially, the Makona Δmucin GP-T577P-T42A (FIL161615), SEQ ID NO:16, was used as a backbone. T577P had been shown previously to increase trimer yield (WO 2017/037196) and the T42A was introduced to knock-out a PNGS site for allowing crystallization of the protein (Zhao et al. Nature. 2016 Jul. 7; 535(7610):169-172). The NativePAGE on FIG. 2 shows that both the K588F and K588W substitutions clearly increased the trimer yield, whereas most of the tested mutations decreased the trimer yield.

K588F in Mayinga, Kikwit and Makona

Analytical SEC Analysis

It was also tested whether K588F stabilizes Makona Δmucin-like GP, in the absence of T42A and T577P and whether it also stabilizes the delta-mucin-like GPs of Mayinga and Kikwit. K588F alone or in combination with T577P was also tested in the complete ectodomains of Makona, Mayinga and Kikwit GPs. The EBOV GP variants were expressed in 96 well format cell cultures. A high-performance liquid chromatography system (Agilent Technologies) and MiniDAWN TREOS instrument (Wyatt) coupled to an Optilab T-rEX Refractive Index Detector (Wyatt) was used for performing the analytical SEC experiment. The cleared supernatants were applied to a TSK-Gel G3000SWxl column (Tosoh Bioscience) equilibrated in running buffer (150 mM sodium phosphate, 50 mM NaCl, pH 7.0) at 1 mL/min. The data were analyzed using the Astra 6 software package.

Figure 3:
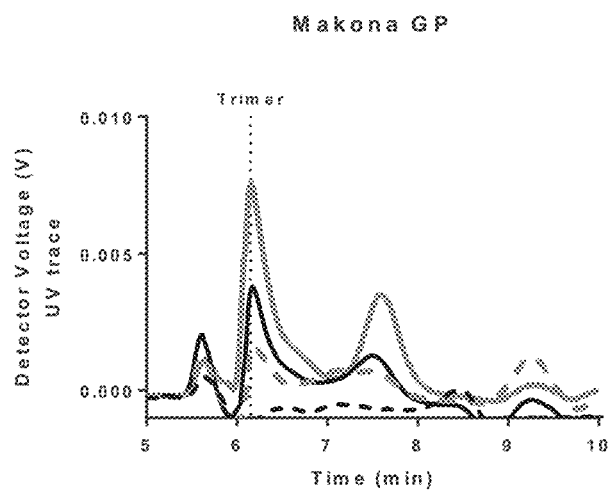
FIG. 3. Analytical SEC on cell culture supernatants containing GPs with diverse substitutions. The trimer peak is indicated with a dashed line labeled with 'trimer'. The substitutions tested are T577P, K588F and a combination of T577P-K588F. Protein expression levels which were measured using analytical SEC are disclosed for each backbone Filo GPs (black broken line) and for variants with T577P (grey broken line), K588F (solid black line) and T577P+K588F double substitutions (grey solid line). The substitutions were tested in the following backbones: A) Makona GP, B) Makona Δmucin-like domain GP, C) Kikwit GP, D) Kikwit Δmucin-like domain GP, E) Mayinga GP, F) Mayinga Δmucin-like domain GP. Protein expression levels in cell culture supernatants were tested 72 h post transfection.
Figure 3:
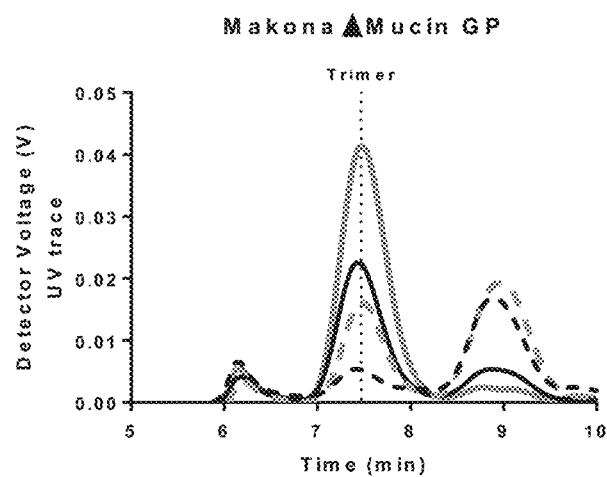
Figure 3:
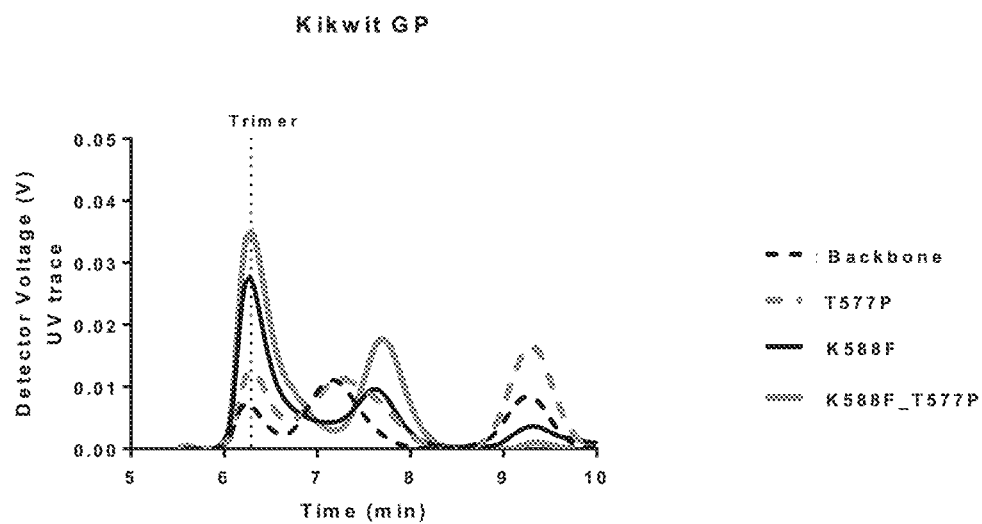
Figure 4:
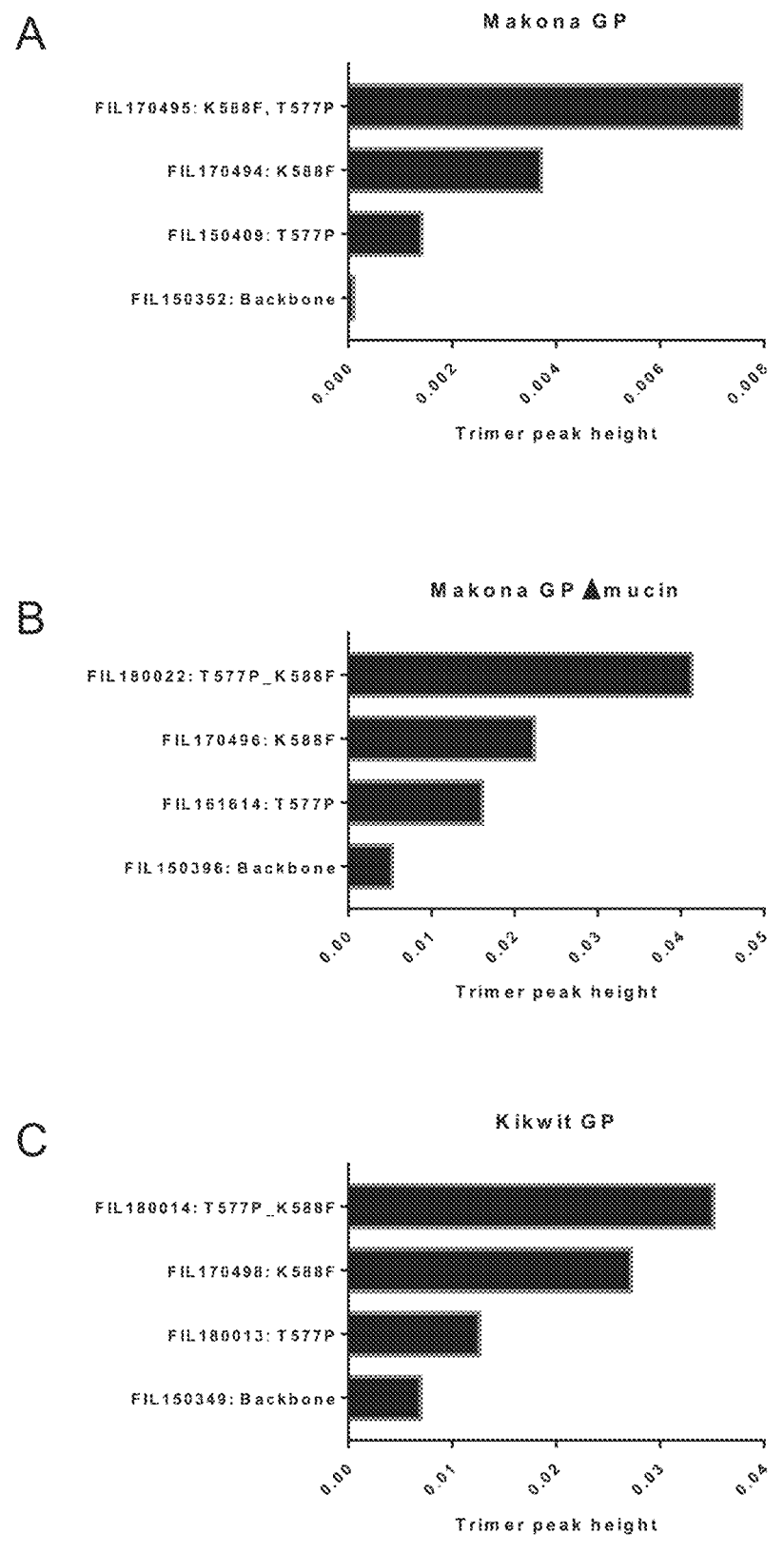
Figure 5:
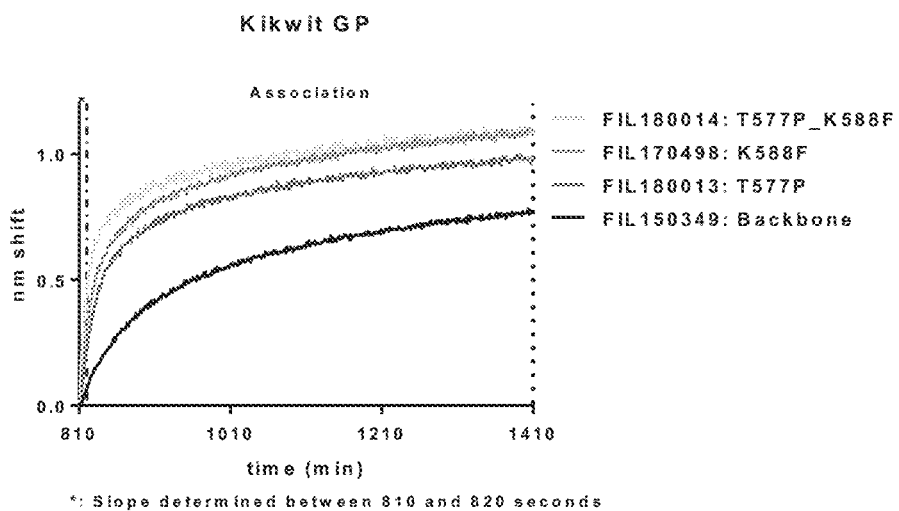
FIG. 5. Biolayer Interferometry with antibody 100.
Figure 5:
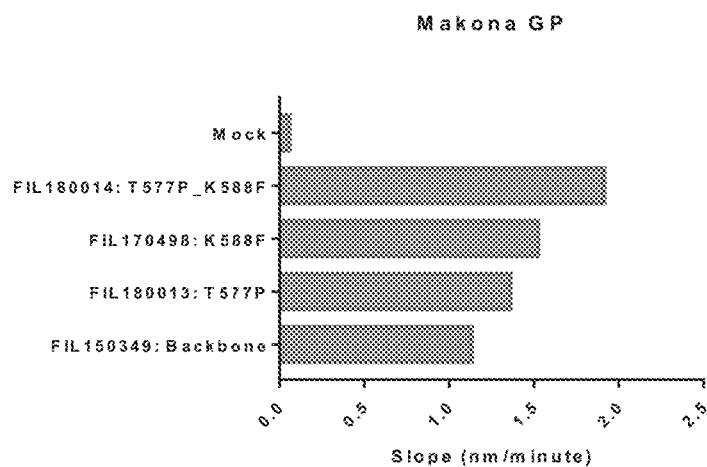
Figure 5:
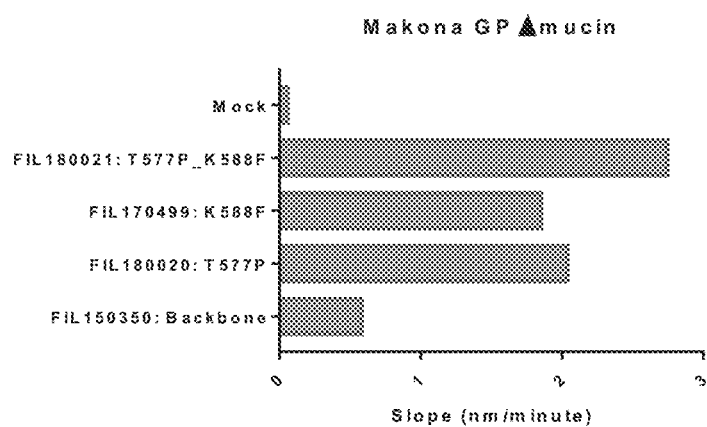

The analytical SEC chromatograms of the Ebola GPs and the variants containing either T577P, K588F or T577P combined with K588F mutations are shown in FIG. 3. The chromatogram of the GPs has multiple peaks. The trimer of the full ectodomain elutes at approximately 6.3 minutes and that of the delta-mucin variants elute at around 7.5 minutes. FIG. 4 shows a bar graph of the trimer peak heights of the SEC chromatograms in FIG. 3. Cell culture supernatants were measured using Biolayer Interferometry (BLI) using Octet for binding of antibody 100, which preferentially binds to the trimeric forms of Ebola GP (FIG. 5). Therefore, the binding rate at 10 seconds (in nm shift/minute) of antibody 100 gives a good indication of the presence of correctly folded trimers. The nm shift at 600 seconds are not as diverse as the nm shift at 10 seconds, which may indicate that antibody 100 is able to induce trimer formation by the monomers in solution. The binding rates at 10 seconds show a very similar ranking of the mutants for trimer content as was seen with analytical SEC, so the results of the analytical SEC were verified by the BLI data.

BioLayer Interferometry (BLI)

Antibody 100 was immobilized on anti-hIgG (AHC) sensors (FortéBio cat #18-5060) at a concentration of 10 µg/ml in lx kinetics buffer (FortéBio cat #18-1092) in 96-half well black flat bottom polypylene microplates (FortéBio cat #3694). The experiment was performed on an Octet HTX instrument (Pall-FortéBio) at 30° C. shaking speed 1,000 rpm. Activation was 60s, immobilization of antibodies 600s, then washing 150s and then binding the Envs 600s, followed by a dissociation of 60 s, all shaking at 1000 rpm. The data analysis was performed using the FortéBio Data Analysis 8.1 software (FortéBio). The binding slope was determined at 10 seconds in nm/minute.

Example 3: Hydrophobic Residues at Position 588 Increase Trimer Yield

Substitutions at position 588 with phenylalanine, alanine, valine, isoleucine, leucine, methionine and tyrosine were tested with analytical SEC and BLI (Octet) using antibody 100 for Mayinga GP and Mayinga delta mucin GP (FIG. 6). Substitutions with phenylalanine, valine, isoleucine, leucine, methionine and tyrosine increased the trimer yields substantially. Alanine and tryptophan did not increase the trimer yield so much in the Mayinga delta mucin GP. In Mayinga delta mucin GP all other possible amino acids substitutions were tested, but none of the additional possibilities resulted in an increase in trimer yield (FIG. 6)

Example 4: Stability of Trimeric Marburg GPs

Substitution at 588 Stabilizes Marburg GP

Figure 7:
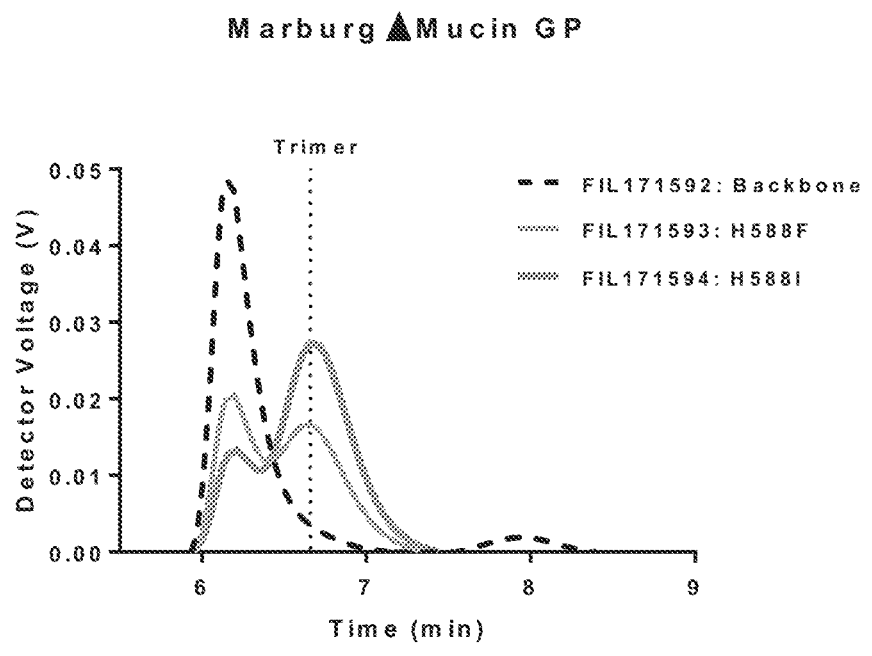

To establish the universality of the stabilizing substitution for other Filoviridae, the substitution at position 588 was also introduced in Marburg GP which only has ~32% identity to Ebola GP. The position that is homologous to the 588 position in the Ebola GP is located at position 589 in the Marburg GP sequence (SEQ ID NO:43). However, since we use the numbering according to the numbering of Mayinga GP (Z/Zaire/Yambuku/1976/057935), SEQ ID NO:1 (Sanchez, A. et al. 1996 PNAS USA 93:3602-3607), we will refer herein to position 588. As a backbone (FIL171592, SEQ ID NO: 27) we used a Marburg GP with the mucin-like domain deleted and with four mutations, i.e. F438L, W439A, F445G, and F447N, to increase furin cleavage (Hashiguchi et al. Cell, 2015 160, 904-912, February 26), to which we refer to here as Marburg Δmucin GP. The H588F and H588I substitutions in the Marburg Δmucin GP had a very favorable effect on the native folding of the Marburg Δmucin GP trimer. The unmutated Marburg Δmucin GP produced mainly aggregates but in contrast, especially the H588I produced much less aggregates and a clear product peak (FIG. 7). The H588I/F mutations increased trimer yield and percentage in the Marburg Δmucin-like domain GP.

The examples above demonstrate that the invention provides a universal approach to optimize the folding and stability of prefusion-closed Filovirus GP trimer proteins.

It is understood that the examples and embodiments described herein are for illustrative purposes only, and that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claims.

LIST OF SEQUENCES

Sequences of Backbones and Mutants for Testing Substitutions

SEQ ID NO: 1 (NP_066246.1 spike glycoprotein [Zaire ebolavirus] (Z/Zaire/Yambuku/1976/057935)) (signal sequence in bold italics)
MGVTGILQLPRDRFKRTSFFLWVIILFQRTF-SIPLGVIHN-
STLQVSDVDKLVCRDKLSSTNQLRSVGLNL EGNG-
VATDVPSATKRWGFRSGVPPKVVNYEAGEWAENCYN-
LEIKKPDGSECLPAAPDGIRGFPRCRYV
HKVSGTGPCAGDFAFHKEGAFFLYDRLAST-
VIYRGTTFAEGVVAFLILPQAKKDFFSSHPL-
REPVNATEDP SSGYYSTTIRYQATGFGTNETEYLFE-
VDNLTYVQLESRFTPQFLLQLNETIYTSGKRSNTTGK-
LIWKVNPE
IDTTIGEWARNETKKNLTRKIRSEELSFTVVSN-
GAKNISGQSPARTSSDPGTNTTTEDHKIMASENSSAM
VQVHSQGREAAVSHLTTLATISTSPQSLTTKPGPDN-
STHNTPVYKLDISEATQVEQHHRRTDNDSTASDT
PSATTAAGPPKAENTNTSKSTDFLDPATTTSPQNH-
SETAGNNNTHHQDTGEESASSGKLGLITNTIAGVA
GLITGGRRTRREAIVNAQPKCNPNLHYWTTQDE-
GAAIGLAWIPYFGPAAEGIYIEGLMHNQDGLICGLRQ
LANETTQALQLFLRATTELRTFSILNRKAID-
FLLQRWGGTCHILGPDCCIEPHDWTKNITD-
KIDQIIHDF VDKTLPDQGDNDNWWTGWRQWIPA-
GIGVTGVIIAVIALFCICKFVF SEQ ID NO: 2 (FIL150282 Mayinga GP-647) (mucin-like domain underlined)
IPLGVIHN-
STLQVSDVDKLVCRDKLSSTNQLRSVGLNLEGNG-
VATDVPSATKRWGFRSGVPPKVVNYEA GEWAEN-
CYNLEIKKPDGSECLPAAPDGIRGFPRCRYVHKVSG-
TGPCAGDFAFHKEGAFFLYDRLASTVIY RGTTFAE-
GVVAFLILPQAKKDFFSSHPLREPVNAT-
EDPSSGYYSTTIRYQATGFGTNETEYLFEVDNLTYV
QLESRFTPQFLLQLNETIYTSGKRSNTTGKLIWKVN-
PEIDTTIGEWAFWETKKNLTRKIRSEELSFTVVSNG
AKNISGQSPARTSSDPGTNTTTEDHKIMASENSSA-
MVQVHSQGREAAVSHLTTLATISTSPQSLTTKPGP
DNSTHNTPVYKLDISEATQVEQHHRRTDNDST-
ASDTPSATTAAGPPKAENTNTSKSTDFLDPATTTSPQN
HSETAGNNNTHHQDTGEESASSGKLGLITNTIAGVA-
GLITGGRRTRREAIVNAQPKCNPNLHYWTTQDEG
AAIGLAWIPYFGPAAEGIYIEGLMHNQDG-
LICGLRQLANETTQALQLFLRATTELRTFSILNRKAID-
FLLQRW GGTCHILGPDCCIEPHDWTKNITD-
KIDQIIHDFVDKTLPDQGDNDNWWTG SEQ ID NO: 3 (FIL180011 Mayinga GP-647, T577P) (introduced mutation indicated by grey shading)
IPLGVIHN-
STLQVSDVDKLVCRDKLSSTNQLRSVGLNLEGNG-
VATDVPSATKRWGFRSGVPPKVVNYEA GEWAEN-
CYNLEIKKPDGSECLPAAPDGIRGFPRCRYVHKVSG-
TGPCAGDFAFHKEGAFFLYDRLASTVIY RGTTFAE-
GVVAFLILPQAKKDFFSSHPLREPVNAT-
EDPSSGYYSTTIRYQATGFGTNETEYLFEVDNLTYV
QLESRFTPQFLLQLNETIYTSGKRSNTTGKLIWKVN-
PEIDTTIGEWAFWETKKNLTRKIRSEELSFTVVSNG
AKNISGQSPARTSSDPGTNTTTEDHKIMASENSSA-
MVQVHSQGREAAVSHLTTLATISTSPQSLTTKPGP
DNSTHNTPVYKLDISEATQVEQHHRRTDNDST-
ASDTPSATTAAGPPKAENTNTSKSTDFLDPATTTSPQN
HSETAGNNNTHHQDTGEESASSGKLGLITNTIAGVA-
GLITGGRRTRREAIVNAQPKCNPNLHYWTTQDEG
AAIGLAWIPYFGPAAEGIYIEGLMHNQDG-
LICGLRQLANETTQALQLFLRATPELRTFSILNRKAID-
FLLQRW GGTCHILGPDCCIEPHDWTKNITD-
KIDQIIHDFVDKTLPDQGDNDNWWTG SEQ ID NO: 4 (FIL170497 Mayinga GP-647, K588F) (introduced mutation indicated by grey shading)
IPLGVIHN-
STLQVSDVDKLVCRDKLSSTNQLRSVGLNLEGNG-
VATDVPSATKRWGFRSGVPPKVVNYEA GEWAEN-
CYNLEIKKPDGSECLPAAPDGIRGFPRCRYVHKVSG-
TGPCAGDFAFHKEGAFFLYDRLASTVIY RGTTFAE-
GVVAFLILPQAKKDFFSSHPLREPVNAT-
EDPSSGYYSTTIRYQATGFGTNETEYLFEVDNLTYV
QLESRFTPQFLLQLNETIYTSGKRSNTTGKLIWKVN-
PEIDTTIGEWAFWETKKNLTRKIRSEELSFTVVSNG
AKNISGQSPARTSSDPGTNTTTEDHKIMASENSSA-
MVQVHSQGREAAVSHLTTLATISTSPQSLTTKPGP
DNSTHNTPVYKLDISEATQVEQHHRRTDNDST-
ASDTPSATTAAGPPKAENTNTSKSTDFLDPATTTSPQN
HSETAGNNNTHHQDTGEESASSGKLGLITNTIAGVA-
GLITGGRRTRREAIVNAQPKCNPNLHYWTTQDEG
AAIGLAWIPYFGPAAEGIYIEGLMHNQDG-
LICGLRQLANETTQALQLFLRATTELRTFSILNRFAID-
FLLQRW GGTCHILGPDCCIEPHDWTKNITD-
KIDQIIHDFVDKTLPDQGDNDNWWTG SEQ ID NO: 5 (FIL180012 Mayinga GP-647-T577P, K588F) (introduced mutations indicated by grey shading)
IPLGVIHN-
STLQVSDVDKLVCRDKLSSTNQLRSVGLNLEGNG-
VATDVPSATKRWGFRSGVPPKVVNYEA GEWAEN-
CYNLEIKKPDGSECLPAAPDGIRGFPRCRYVHKVSG-
TGPCAGDFAFHKEGAFFLYDRLASTVIY RGTTFAE-
GVVAFLILPQAKKDFFSSHPLREPVNAT-
EDPSSGYYSTTIRYQATGFGTNETEYLFEVDNLTYV
QLESRFTPQFLLQLNETIYTSGKRSNTTGKLIWKVN-
PEIDTTIGEWAFWETKKNLTRKIRSEELSFTVVSNG
AKNISGQSPARTSSDPGTNTTTEDHKIMASENSSA-
MVQVHSQGREAAVSHLTTLATISTSPQSLTTKPGP
DNSTHNTPVYKLDISEATQVEQHHRRTDNDST-
ASDTPSATTAAGPPKAENTNTSKSTDFLDPATTTSPQN
HSETAGNNNTHHQDTGEESASSGKLGLITNTIAGVA-
GLITGGRRTRREAIVNAQPKCNPNLHYWTTQDEG
AAIGLAWIPYFGPAAEGIYIEGLMHNQDG-
LICGLRQLANETTQALQLFLRATPELRTFSILNRKAID-
FLLQRW GGTCHILGPDCCIEPHDWTKNITD-
KIDQIIHDFVDKTLPDQGDNDNWWTG SEQ ID NO: 6 (FIL150351 Mayinga GP-647, delta mucin-like domain (4320-476))
IPLGVIHN-
STLQVSDVDKLVCRDKLSSTNQLRSVGLNLEGNG-
VATDVPSATKRWGFRSGVPPKVVNYEA GEWAEN-
CYNLEIKKPDGSECLPAAPDGIRGFPRCRYVHKVSG-
TGPCAGDFAFHKEGAFFLYDRLASTVIY RGTTFAE-
GVVAFLILPQAKKDFFSSHPLREPVNAT-
EDPSSGYYSTTIRYQATGFGTNETEYLFEVDNLTYV QLESRFTPQFLLQLNETIYTSGKRSNTTGKLIWKVNPEIDTTIGEWAFWETKKNLTRKIRSEELSFTVVSNGAKNISGKLGLITNTIAGVAGLITGGRRTRREAIVNAQPKCNPNLHYWTTQDEGAAIGLAWIPYFGPAAEGIYI EGLMHNQDGLICGLRQLANETTQALQLFLRATTELRTFSILNRKAIDFLLQRWGGTCHILGPDCCIEPHDW TKNITDKIDQIIHDFVDKTLPDQGDNDNWWTG SEQ ID NO: 7 (FIL180018 Mayinga GP-647, delta mucin-like domain (4320-476), T577P) (introduced mutation indicated by grey shading)
IPLGVIHNSTLQVSDVDKLVCRDKLSSTNQLRSVGLNLEGNGVATDVPSATKRWGFRSGVPPKVVNYEA GEWAENCYNLEIKKPDGSECLPAAPDGIRGFPRCRYVHKVSGTGPCAGDFAFHKEGAFFLYDRLASTVIY RGTTFAEGVVAFLILPQAKKDFFSSHPLREPVNATEDPSSGYYSTTIRYQATGFGTNETEYLFEVDNLTYVQLESRFTPQFLLQLNETIYTSGKRSNTTGKLIWKVNPEIDTTIGEWAFWETKKNLTRKIRSEELSFTVVSNGAKNISGKLGLITNTIAGVAGLITGGRRTRREAIVNAQPKCNPNLHYWTTQDEGAAIGLAWIPYFGPAAEGIYI EGLMHNQDGLICGLRQLANETTQALQLFLRATPELRTFSILNRKAIDFLLQRWGGTCHILGPDCCIEPHDW TKNITDKIDQIIHDFVDKTLPDQGDNDNWWTG SEQ ID NO: 8 (FIL170500 Mayinga GP-647, delta mucin-like domain (4320-476), K588F) (introduced mutation indicated by grey shading)
IPLGVIHNSTLQVSDVDKLVCRDKLSSTNQLRSVGLNLEGNGVATDVPSATKRWGFRSGVPPKVVNYEA GEWAENCYNLEIKKPDGSECLPAAPDGIRGFPRCRYVHKVSGTGPCAGDFAFHKEGAFFLYDRLASTVIY RGTTFAEGVVAFLILPQAKKDFFSSHPLREPVNATEDPSSGYYSTTIRYQATGFGTNETEYLFEVDNLTYVQLESRFTPQFLLQLNETIYTSGKRSNTTGKLIWKVNPEIDTTIGEWAFWETKKNLTRKIRSEELSFTVVSNGAKNISGKLGLITNTIAGVAGLITGGRRTRREAIVNAQPKCNPNLHYWTTQDEGAAIGLAWIPYFGPAAEGIYI EGLMHNQDGLICGLRQLANETTQALQLFLRATTELRTFSILNRFAIDFLLQRWGGTCHILGPDCCIEPHDW TKNITDKIDQIIHDFVDKTLPDQGDNDNWWTG SEQ ID NO: 9 (FIL180019 Mayinga GP-647, delta mucin-like domain (4320-476), T577P) (introduced mutations indicated by grey shading)
IPLGVIHNSTLQVSDVDKLVCRDKLSSTNQLRSVGLNLEGNGVATDVPSATKRWGFRSGVPPKVVNYEA GEWAENCYNLEIKKPDGSECLPAAPDGIRGFPRCRYVHKVSGTGPCAGDFAFHKEGAFFLYDRLASTVIY RGTTFAEGVVAFLILPQAKKDFFSSHPLREPVNATEDPSSGYYSTTIRYQATGFGTNETEYLFEVDNLTYVQLESRFTPQFLLQLNETIYTSGKRSNTTGKLIWKVNPEIDTTIGEWAFWETKKNLTRKIRSEELSFTVVSNGAKNISGKLGLITNTIAGVAGLITGGRRTRREAIVNAQPKCNPNLHYWTTQDEGAAIGLAWIPYFGPAAEGIYI EGLMHNQDGLICGLRQLANETTQALQLFLRATPELRTFSILNRFAIDFLLQRWGGTCHILGPDCCIEPHDW TKNITDKIDQIIHDFVDKTLPDQGDNDNWWTG SEQ ID NO: 10 (FIL150352 Makona GP-647) (mucin-like domain underlined)
IPLGVIHNSTLQVSDVDKLVCRDKLSSTNQLRSVGLNLEGNGVATDVPSVTKRWGFRSGVPPKVVNYEA GEWAENCYNLEIKKPDGSECLPAAPDGIRGFPRCRYVHKVSGTGPCAGDFAFHKEGAFFLYDRLASTVIY RGTTFAEGVVAFLILPQAKKDFFSSHPLREPVNATEDPSSGYYSTTIRYQATGFGTNETEYLFEVDNLTYVQLESRFTPQFLLQLNETIYASGKRSNTTGKLIWKVNPEIDTTIGEWARNETKKNLTRKIRSEELSFTAVSNGPKNISGQSPARTSSDPETNTTNEDHKIMASENSSAMVQVHSQGRKAAVSHLTTLATISTSPQPPTTKTGPDNSTHNTPVYKLDISEATQVGQHHRRADNDSTASDTPPATTAAGPLKAENTNTSKSADSLDLATTTSPQN YSETAGNNNTHHQDTGEESASSGKLGLITNTIAGVAGLITGGRRTRREVIVNAQPKCNPNLHYWTTQDEG AAIGLAWIPYFGPAAEGIYTEGLMHNQDGLICGLRQLANETTQALQLFLRATTELRTFSILNRKAIDFLLQR WGGTCHILGPDCCIEPHDWTKNITDKIDQIIHDFVDKTLPDQGDNDNWWTG SEQ ID NO: 11 (FIL150409 Makona GP-647, T577P) (introduced mutation indicated by grey shading)
IPLGVIHNSTLQVSDVDKLVCRDKLSSTNQLRSVGLNLEGNGVATDVPSVTKRWGFRSGVPPKVVNYEA GEWAENCYNLEIKKPDGSECLPAAPDGIRGFPRCRYVHKVSGTGPCAGDFAFHKEGAFFLYDRLASTVIY RGTTFAEGVVAFLILPQAKKDFFSSHPLREPVNATEDPSSGYYSTTIRYQATGFGTNETEYLFEVDNLTYVQLESRFTPQFLLQLNETIYASGKRSNTTGKLIWKVNPEIDTTIGEWARNETKKNLTRKIRSEELSFTAVSNGPKNISGQSPARTSSDPETNTTNEDHKIMASENSSAMVQVHSQGRKAAVSHLTTLATISTSPQPPTTKTGPDNSTHNTPVYKLDISEATQVGQHHRRADNDSTASDTPPATTAAGPLKAENTNTSKSADSLDLATTTSPQN YSETAGNNNTHHQDTGEESASSGKLGLITNTIAGVAGLITGGRRTRREVIVNAQPKCNPNLHYWTTQDEG AAIGLAWIPYFGPAAEGIYTEGLMHNQDGLICGLRQLANETTQALQLFLRATPELRTFSILNRKAIDFLLQR WGGTCHILGPDCCIEPHDWTKNITDKIDQIIHDFVDKTLPDQGDNDNWWTG SEQ ID NO: 12 (FIL170494 Makona GP-647, K588F) (introduced mutation indicated by grey shading)
IPLGVIHNSTLQVSDVDKLVCRDKLSSTNQLRSVGLNLEGNGVATDVPSVTKRWGFRSGVPPKVVNYEA GEWAENCYNLEIKKPDGSECLPAAPDGIRGFPRCRYVHKVSGTGPCAGDFAFHKEGAFFLYDRLASTVIY RGTTFAEGVVAFLILPQAKKDFFSSHPLREPVNATEDPSSGYYSTTIRYQATGFGTNETEYLFEVDNLTYVQLESRFTPQFLLQLNETIYASGKRSNTTGKLIWKVNPEIDTTIGEWARNETKKNLTRKIRSEELSFTAVSNGPKNISGQSPARTSSDPETNTTNEDHKIMASENSSAMVQVHSQGRKAAVSHLTTLATISTSPQPPTTKTGPDNSTHNTPVYKLDISEATQVGQHHRRADNDSTASDTPPATTAAGPLKAENTNTSKSADSLDLATTTSPQN YSETAGNNNTHHQDTGEESASSGKLGLITNTIAGVAGLITGGRRTRREVIVNAQPKCNPNLHYWTTQDEG AAIGLAWIPYFGPAAEGIYTEGLMHNQDGLICGLRQLANETTQALQLFLRATTELRTFSILNRFAIDFLLQR WGGTCHILGPDCCIEPHDWTKNITDKIDQIIHDFVDKTLPDQGDNDNWWTG SEQ ID NO: 13 (FIL170495 Makona GP-647, T577P, K588F) (introduced mutations indicated by grey shading)
IPLGVIHNSTLQVSDVDKLVCRDKLSSTNQLRSVGLNLEGNGVATDVPSVTKRWGFRSGVPPKVVNYEA GEWAENCYNLEIKKPDGSECLPAAPDGIRGFPRCRYVHKVSGTGPCAGDFAFHKEGAFFLYDRLASTVIY RGTTFAEGVVAFLILPQAKKDFFSSHPLREPVNATEDPSSGYYSTTIRYQATGFGTNETEYLFEVDNLTYV QLESRFTPQFLLQLNETIYASGKRSNTTGKLIWKVNPEIDTTIGEWARNETKKNLTRKIRSEELSFTAVSNGPKNISGQSPARTSSDPETNTTNEDHKIMASENSSAMVQVHSQGRKAAVSHLTTLATISTSPQPPTTKTGPDNSTHNTPVYKLDISEATQVGQHHRRADNDSTASDTPPATTAAGPLKAENTNTSKSADSLDLATTTSPQN YSETAGNNNTHHQDTGEESASSGKLGLITNTIAGVAGLITGGRRTRREVIVNAQPKCNPNLHYWTTQDEG AAIGLAWIPYFGPAAEGIYTEGLMHNQDGLICGLRQLANETTQALQLFLRATPELRTFSILNRFAIDFLLQR WGGTCHILGPDCCIEPHDWTKNITDKIDQIIHDFVDKTLPDQGDNDNWWTG SEQ ID NO: 14 (FIL150396 Makona GP-647, delta mucin-like domain (4314-472))
IPLGVIHNSTLQVSDVDKLVCRDKLSSTNQLRSVGLNLEGNGVATDVPSVTKRWGFRSGVPPKVVNYEA GEWAENCYNLEIKKPDGSECLPAAPDGIRGFPRCRYVHKVSGTGPCAGDFAFHKEGAFFLYDRLASTVIY RGTTFAEGVVAFLILPQAKKDFFSSHPLREPVNATEDPSSGYYSTTIRYQATGFGTNETEYLFEVDNLTYVQLESRFTPQFLLQLNETIYASGKRSNTTGKLIWKVNPEIDTTIGEWAFWETKKNLTRKIRSEELSFTAVSNSASSGKLGLITNTIAGVAGLITGGRRTRREVIVNAQPKCNPNLHYWTTQDEGAAIGLAWIPYFGPAAEGIYTE GLMHNQDGLICGLRQLANETTQALQLFLRATTELRTFSILNRKAIDFLLQRWGGTCHILGPDCCIEPHDWT KNITDKIDQIIHDFVDKTLPDQGDNDNWWTG SEQ ID NO: 15 (FIL161614 Makona GP-647, delta mucin-like domain (4314-472), T577P) (introduced mutation indicated by grey shading)
IPLGVIHNSTLQVSDVDKLVCRDKLSSTNQLRSVGLNLEGNGVATDVPSVTKRWGFRSGVPPKVVNYEA GEWAENCYNLEIKKPDGSECLPAAPDGIRGFPRCRYVHKVSGTGPCAGDFAFHKEGAFFLYDRLASTVIY RGTTFAEGVVAFLILPQAKKDFFSSHPLREPVNATEDPSSGYYSTTIRYQATGFGTNETEYLFEVDNLTYVQLESRFTPQFLLQLNETIYASGKRSNTTGKLIWKVNPEIDTTIGEWARNETKKNLTRKIRSEELSFTAVSNSASSGKLGLITNTIAGVAGLITGGRRTRREVIVNAQPKCNPNLHYWTTQDEGAAIGLAWIPYFGPAAEGIYTE GLMHNQDGLICGLRQLANETTQALQLFLRATPELRTFSILNRKAIDFLLQRWGGTCHILGPDCCIEPHDWT KNITDKIDQIIHDFVDKTLPDQGDNDNWWTG SEQ ID NO: 16 (FIL161615 Makona GP-647, delta mucin-like domain (4314-472), T577P, T42A) (introduced mutations indicated by grey shading)
IPLGVIHNSALQVSDVDKLVCRDKLSSTNQLRSVGLNLEGNGVATDVPSVTKRWGFRSGVPPKVVNYEA GEWAENCYNLEIKKPDGSECLPAAPDGIRGFPRCRYVHKVSGTGPCAGDFAFHKEGAFFLYDRLASTVIY RGTTFAEGVVAFLILPQAKKDFFSSHPLREPVNATEDPSSGYYSTTIRYQATGFGTNETEYLFEVDNLTYVQLESRFTPQFLLQLNETIYASGKRSNTTGKLIWKVNPEIDTTIGEWARNETKKNLTRKIRSEELSFTAVSNSASSGKLGLITNTIAGVAGLITGGRRTRREVIVNAQPKCNPNLHYWTTQDEGAAIGLAWIPYFGPAAEGIYTE GLMHNQDGLICGLRQLANETTQALQLFLRATPELRTFSILNRKAIDFLLQRWGGTCHILGPDCCIEPHDWT KNITDKIDQIIHDFVDKTLPDQGDNDNWWTG SEQ ID NO: 17 (FIL170496 Makona GP-647, delta mucin-like domain (4314-472), K588F) (introduced mutation indicated by grey shading)
IPLGVIHNSTLQVSDVDKLVCRDKLSSTNQLRSVGLNLEGNGVATDVPSVTKRWGFRSGVPPKVVNYEA GEWAENCYNLEIKKPDGSECLPAAPDGIRGFPRCRYVHKVSGTGPCAGDFAFHKEGAFFLYDRLASTVIY RGTTFAEGVVAFLILPQAKKDFFSSHPLREPVNATEDPSSGYYSTTIRYQATGFGTNETEYLFEVDNLTYVQLESRFTPQFLLQLNETIYASGKRSNTTGKLIWKVNPEIDTTIGEWARNETKKNLTRKIRSEELSFTAVSNSASSGKLGLITNTIAGVAGLITGGRRTRREVIVNAQPKCNPNLHYWTTQDEGAAIGLAWIPYFGPAAEGIYTE GLMHNQDGLICGLRQLANETTQALQLFLRATTELRTFSILNRFAIDFLLQRWGGTCHILGPDCCIEPHDWT KNITDKIDQIIHDFVDKTLPDQGDNDNWWTG SEQ ID NO: 18 (FIL180022 Makona GP-647, delta mucin-like domain (4314-472), T577P, K588F) (introduced mutations indicated by grey shading)
IPLGVIHNSTLQVSDVDKLVCRDKLSSTNQLRSVGLNLEGNGVATDVPSVTKRWGFRSGVPPKVVNYEA GEWAENCYNLEIKKPDGSECLPAAPDGIRGFPRCRYVHKVSGTGPCAGDFAFHKEGAFFLYDRLASTVIY RGTTFAEGVVAFLILPQAKKDFFSSHPLREPVNATEDPSSGYYSTTIRYQATGFGTNETEYLFEVDNLTYV QLESRFTPQFLLQLNETIYASGKRSNTTGKLIWKVNPEIDTTIGEWAFWETKKNLTRKIRSEELSFTAVSNS ASSGKLGLITNTIAGVAGLITGGRRTRREVIVNAQPKCNPNLHYWTTQDEGAAIGLAWIPYFGPAAEGIYTE GLMHNQDGLICGLRQLANETTQALQLFLRATPELRTFSILNRFAIDFLLQRWGGTCHILGPDCCIEPHDWT KNITDKIDQIIHDFVDKTLPDQGDNDNWWTG SEQ ID NO: 19 (FIL150349 Kikwit GP-647) (mucin-like domain underlined)
IPLGVIHNSTLQVSDVDKLVCRDKLSSTNQLRSVGLNLEGNGVATDVPSATKRWGFRSGVPPKVVNYEA GEWAENCYNLEIKKPDGSECLPAAPDGIRGFPRCRYVHKVSGTGPCAGDFAFHKEGAFFLYDRLASTVIY RGTTFAEGVVAFLILPQAKKDFFSSHPLREPVNATEDPSSGYYSTTIRYQATGFGTNETEYLFEVDNLTYV QLESRFTPQFLLQLNETIYTSGKRSNTTGKLIWKVNPEIDTTIGEWAFWETKKNLTRKIRSEELSFTAVSNR AKNISGQSPARTSSDPGTNTTTEDHKIMASENSSAMVQVHSQGREAAVSHLTTLATISTSPQPPTTKPGPDNSTHNTPVYKLDISEATQVEQHHRRTDNDSTASDTPPATTAAGPLKAENTNTSKGTDLLDPATTTSPQN HSETAGNNNTHHQDTGEESASSGKLGLITNTIAGVAGLITGGRRARREAIVNAQPKCNPNLHYWTTQDE GAAIGLAWIPYFGPAAEGIYIEGLMHNQDGLICGLRQLANETTQALQLFLRATTELRTFSILNRKAIDFLLQR WGGTCHILGPDCCIEPHDWTKNITDKIDQIIHDFVDKTLPDQGDNDNWWTG SEQ ID NO: 20 (FIL180013 Kikwit GP-647, T577P) (introduced mutation indicated by grey shading)
IPLGVIHNSTLQVSDVDKLVCRDKLSSTNQLRSVGLNLEGNGVATDVPSATKRWGFRSGVPPKVVNYEA GEWAENCYNLEIKKPDGSECLPAAPDGIRGFPRCRYVHKVSGTGPCAGDFAFHKEGAFFLYDRLASTVIY RGTTFAEGVVAFLILPQAKKDFFSSHPLREPVNATEDPSSGYYSTTIRYQATGFGTNETEYLFEVDNLTYV QLESRFTPQFLLQLNETIYTSGKRSNTTGKLIWKVNPEIDTTIGEWAFWETKKNLTRKIRSEELSFTAVSNR AKNISGQSPARTSSDPGTNTTTEDHKIMASENSSAMVQVHSQGREAAVSHLTTLATISTSPQPPTTKPGPDNSTHNTPVYKLDISEATQVEQHHRRTDNDSTASDTPPATTAAGPLKAENTNTSKGTDLLDPATTTSPQN HSETAGNNNTHHQDTGEESASSGKLGLITNTIAGVAGLITGGRRARREAIVNAQPKCNPNLHYWTTQDE GAAIGLAWIPYFGPAAEGIYIEGLMHNQDGLICGLRQLANETTQALQLFLRATPELRTFSILNRKAIDFLLQR WGGTCHILGPDCCIEPHDWTKNITDKIDQIIHDFVDKTLPDQGDNDNWWTG SEQ ID NO: 21 (FIL170498 Kikwit GP-647, K588F) (introduced mutation indicated by grey shading)
IPLGVIHNSTLQVSDVDKLVCRDKLSSTNQLRSVGLNLEGNGVATDVPSATKRWGFRSGVPPKVVNYEA GEWAENCYNLEIKKPDGSECLPAAPDGIRGFPRCRYVHKVSGTGPCAGDFAFHKEGAFFLYDRLASTVIY RGTTFAEGVVAFLILPQAKKDFFSSHPLREPVNATEDPSSGYYSTTIRYQATGFGTNETEYLFEVDNLTYVQLESRFTPQFLLQLNETIYTSGKRSNTTGKLIWKVNPEIDTTIGEWAFWETKKNLTRKIRSEELSFTAVSNRAKNISGQSPARTSSDPGTNTTTEDHKIMASENSSAMVQVHSQGREAAVSHLTTLATISTSPQPPTTKPGPDNSTHNTPVYKLDISEATQVEQHHRRTDNDSTASDTPPATTAAGPLKAENTNTSKGTDLLDPATTTSPQN HSETAGNNNTHHQDTGEESASSGKLGLITNTIAGVAGLITGGRRARREAIVNAQPKCNPNLHYWTTQDE GAAIGLAWIPYFGPAAEGIYIEGLMHNQDGLICGLRQLANETTQALQLFLRATTELRTFSILNRFAIDFLLQR WGGTCHILGPDCCIEPHDWTKNITDKIDQIIHDFVDKTLPDQGDNDNWWTG SEQ ID NO: 22 (FIL180014 Kikwit GP-647, T577P, K588F) (introduced mutations indicated by grey shading)
IPLGVIHNSTLQVSDVDKLVCRDKLSSTNQLRSVGLNLEGNGVATDVPSATKRWGFRSGVPPKVVNYEA GEWAENCYNLEIKKPDGSECLPAAPDGIRGFPRCRYVHKVSGTGPCAGDFAFHKEGAFFLYDRLASTVIY RGTTFAEGVVAFLILPQAKKDFFSSHPLREPVNATEDPSSGYYSTTIRYQATGFGTNETEYLFEVDNLTYVQLESRFTPQFLLQLNETIYTSGKRSNTTGKLIWKVNPEIDTTIGEWAFWETKKNLTRKIRSEELSFTAVSNRAKNISGQSPARTSSDPGTNTTTEDHKIMASENSSAMVQVHSQGREAAVSHLTTLATISTSPQPPTTKPGPDNSTHNTPVYKLDISEATQVEQHHRRTDNDSTASDTPPATTAAGPLKAENTNTSKGTDLLDPATTTSPQN HSETAGNNNTHHQDTGEESASSGKLGLITNTIAGVAGLITGGRRARREAIVNAQPKCNPNLHYWTTQDE GAAIGLAWIPYFGPAAEGIYIEGLMHNQDGLICGLRQLANETTQALQLFLRATPELRTFSILNRFAIDFLLQR WGGTCHILGPDCCIEPHDWTKNITDKIDQIIHDFVDKTLPDQGDNDNWWTG SEQ ID NO: 23 (FIL150350 Kikwit GP-647, delta mucin-like domain (4314-472))
IPLGVIHNSTLQVSDVDKLVCRDKLSSTNQLRSVGLNLEGNGVATDVPSATKRWGFRSGVPPKVVNYEA GEWAENCYNLEIKKPDGSECLPAAPDGIRGFPRCRYVHKVSGTGPCAGDFAFHKEGAFFLYDRLASTVIY RGTTFAEGVVAFLILPQAKKDFFSSHPLREPVNATEDPSSGYYSTTIRYQATGFGTNETEYLFEVDNLTYVQLESRFTPQFLLQLNETIYTSGKRSNTTGKLIWKVNPEIDTTIGEWAFWETKKNLTRKIRSEELSFTAVSNSASSGKLGLITNTIAGVAGLITGGRRARREAIVNAQPKCNPNLHYWTTQDEGAAIGLAWIPYFGPAAEGIYIE GLMHNQDGLICGLRQLANETTQALQLFLRATTELRTFSILNRKAIDFLLQRWGGTCHILGPDCCIEPHDWT KNITDKIDQIIHDFVDKTLPDQGDNDNWWTG SEQ ID NO: 24 (FIL180020 Kikwit GP-647, delta mucin-like domain (4314-472), T577P) (introduced mutation indicated by grey shading)
IPLGVIHNSTLQVSDVDKLVCRDKLSSTNQLRSVGLNLEGNGVATDVPSATKRWGFRSGVPPKVVNYEA GEWAENCYNLEIKKPDGSECLPAAPDGIRGFPRCRYVHKVSGTGPCAGDFAFHKEGAFFLYDRLASTVIY RGTTFAEGVVAFLILPQAKKDFFSSHPLREPVNATEDPSSGYYSTTIRYQATGFGTNETEYLFEVDNLTYVQLESRFTPQFLLQLNETIYTSGKRSNTTGKLIWKVNPEIDTTIGEWAFWETKKNLTRKIRSEELSFTAVSNSASSGKLGLITNTIAGVAGLITGGRRARREAIVNAQPKCNPNLHYWTTQDEGAAIGLAWIPYFGPAAEGIYIE GLMHNQDGLICGLRQLANETTQALQLFLRATPELRTFSILNRKAIDFLLQRWGGTCHILGPDCCIEPHDWT KNITDKIDQIIHDFVDKTLPDQGDNDNWWTG SEQ ID NO: 25 (FIL170499 Kikwit GP-647, delta mucin-like domain (4314-472), K588F) (introduced mutation indicated by grey shading)
IPLGVIHNSTLQVSDVDKLVCRDKLSSTNQLRSVGLNLEGNGVATDVPSATKRWGFRSGVPPKVVNYEA GEWAENCYNLEIKKPDGSECLPAAPDGIRGFPRCRYVHKVSGTGPCAGDFAFHKEGAFFLYDRLASTVIY RGTTFAEGVVAFLILPQAKKDFFSSHPLREPVNATEDPSSGYYSTTIRYQATGFGTNETEYLFEVDNLTYVQLESRFTPQFLLQLNETIYTSGKRSNTTGKLIWKVNPEIDTTIGEWAFWETKKNLTRKIRSEELSFTAVSNSASSGKLGLITNTIAGVAGLITGGRRARREAIVNAQPKCNPNLHYWTTQDEGAAIGLAWIPYFGPAAEGIYIE GLMHNQDGLICGLRQLANETTQALQLFLRATTELRTFSILNRFAIDFLLQRWGGTCHILGPDCCIEPHDWT KNITDKIDQIIHDFVDKTLPDQGDNDNWWTG SEQ ID NO: 26 (FIL180021 Kikwit GP-647, delta mucin-like domain (4314-472), T577P, K588F) (introduced mutations indicated by grey shading)
IPLGVIHNSTLQVSDVDKLVCRDKLSSTNQLRSVGLNLEGNGVATDVPSATKRWGFRSGVPPKVVNYEA GEWAENCYNLEIKKPDGSECLPAAPDGIRGFPRCRYVHKVSGTGPCAGDFAFHKEGAFFLYDRLASTVIY RGTTFAEGVVAFLILPQAKKDFFSSHPLREPVNATEDPSSGYYSTTIRYQATGFGTNETEYLFEVDNLTYVQLESRFTPQFLLQLNETIYTSGKRSNTTGKLIWKVNPEIDTTIGEWAFWETKKNLTRKIRSEELSFTAVSNSASSGKLGLITNTIAGVAGLITGGRRARREAIVNAQPKCNPNLHYWTTQDEGAAIGLAWIPYFGPAAEGIYIE GLMHNQDGLICGLRQLANETTQALQLFLRATPELRTFSILNRFAIDFLLQRWGGTCHILGPDCCIEPHDWT KNITDKIDQIIHDFVDKTLPDQGDNDNWWTG SEQ ID NO: 27 (FIL171592 Marburg GP-637 (MARV) delta mucin-like domain (4255-423))
LPVLEIASNSQPQDVDSVCSGTLQKTEDVHLMGFTLSGQKVADSPLEASKRWAFRTGVPPKNVEYTEGE EAKTCYNISVTDPSGKSLLLDPPSNIRDYPKCKTVHHIQGQNPHAQGIALHLWGAFFLYDRVASTTMYRG KVFTEGNIAAMIVNKTVHRMIFSRQGQGYRHMNLTSTNKYWTSSNETQRNDTGCFGILQEYNSTNNQTCPPSLKPPSLPTVTPSIHSTNTQINTAKSGTRPPIYFRKKRSILAKEGDIGPNLDGLINTEIDFDPIPNTE- TIFDE SPSFNTSTNEEQHTPPNISLTFSYFPDKNGD-TAYSGENENDCDAELRIWSVQEDDLAAGLSWIPFF-GPGI EGLYTAGLIKNQNNLVCRLRR-LANQTAKSLELLLRVTTEERTFSLINRHAIDFLL-TRWGGTCKVLGPDCCIG IEDLSKNISEQIDKIRKDEQ-KEETG SEQ ID NO: 28 (FIL172545 Mayinga GP-647, K588A) (introduced mutation indicated by grey shading)
IPLGVIHN-STLQVSDVDKLVCRDKLSSTNQLRSVGLNLEGNG-VATDVPSATKRWGFRSGVPPKVVNYEA GEWAEN-CYNLEIKKPDGSECLPAAPDGIRGFPRCRYVHKVSG-TGPCAGDFAFHKEGAFFLYDRLASTVIY RGTTFAE-GVVAFLILPQAKKDFFSSHPLREPVNAT-EDPSSGYYSTTIRYQATGFGTNETEYLFEVDNLTYV QLESRFTPQFLLQLNETIYTSGKRSNTTGKLIWKVN-PEIDTTIGEWAFWETKKNLTRKIRSEELSFTVVSNG AKNISGQSPARTSSDPGTNTTTEDHKIMASENSSA-MVQVHSQGREAAVSHLTTLATISTSPQSLTTKPGP DNSTHNTPVYKLDISEATQVEQHHRRTDNDST-ASDTPSATTAAGPPKAENTNTSKSTDFLDPATTTSPQN HSETAGNNNTHHQDTGEESASSGKLGLITNTIAGVA-GLITGGRRTRREAIVNAQPKCNPNLHYWTTQDEG AAIGLAWIPYFGPAAEGIYIEGLMHNQDG-LICGLRQLANETTQALQLFLRATTELRTFSILNRAAID-FLLQRW GGTCHILGPDCCIEPHDWTKNITD-KIDQIIHDFVDKTLPDQGDNDNWWTG SEQ ID NO: 29 (FIL172546 Mayinga GP-647, K588V) (introduced mutation indicated by grey shading)
IPLGVIHN-STLQVSDVDKLVCRDKLSSTNQLRSVGLNLEGNG-VATDVPSATKRWGFRSGVPPKVVNYEA GEWAEN-CYNLEIKKPDGSECLPAAPDGIRGFPRCRYVHKVSG-TGPCAGDFAFHKEGAFFLYDRLASTVIY RGTTFAE-GVVAFLILPQAKKDFFSSHPLREPVNAT-EDPSSGYYSTTIRYQATGFGTNETEYLFEVDNLTYV QLESRFTPQFLLQLNETIYTSGKRSNTTGKLIWKVN-PEIDTTIGEWAFWETKKNLTRKIRSEELSFTVVSNG AKNISGQSPARTSSDPGTNTTTEDHKIMASENSSA-MVQVHSQGREAAVSHLTTLATISTSPQSLTTKPGP DNSTHNTPVYKLDISEATQVEQHHRRTDNDST-ASDTPSATTAAGPPKAENTNTSKSTDFLDPATTTSPQN HSETAGNNNTHHQDTGEESASSGKLGLITNTIAGVA-GLITGGRRTRREAIVNAQPKCNPNLHYWTTQDEG AAIGLAWIPYFGPAAEGIYIEGLMHNQDG-LICGLRQLANETTQALQLFLRATTELRTFSILNRVAID-FLLQRW GGTCHILGPDCCIEPHDWTKNITD-KIDQIIHDFVDKTLPDQGDNDNWWTG SEQ ID NO: 30 (FIL172547 Mayinga GP-647, K588I) (introduced mutation indicated by grey shading)
IPLGVIHN-STLQVSDVDKLVCRDKLSSTNQLRSVGLNLEGNG-VATDVPSATKRWGFRSGVPPKVVNYEA GEWAEN-CYNLEIKKPDGSECLPAAPDGIRGFPRCRYVHKVSG-TGPCAGDFAFHKEGAFFLYDRLASTVIY RGTTFAE-GVVAFLILPQAKKDFFSSHPLREPVNAT-EDPSSGYYSTTIRYQATGFGTNETEYLFEVDNLTYV QLESRFTPQFLLQLNETIYTSGKRSNTTGKLIWKVN-PEIDTTIGEWAFWETKKNLTRKIRSEELSFTVVSNG AKNISGQSPARTSSDPGTNTTTEDHKIMASENSSA-MVQVHSQGREAAVSHLTTLATISTSPQSLTTKPGP DNSTHNTPVYKLDISEATQVEQHHRRTDNDST-ASDTPSATTAAGPPKAENTNTSKSTDFLDPATTTSPQN HSETAGNNNTHHQDTGEESASSGKLGLITNTIAGVA-GLITGGRRTRREAIVNAQPKCNPNLHYWTTQDEG AAIGLAWIPYFGPAAEGIYIEGLMHNQDG-LICGLRQLANETTQALQLFLRATTELRTFSILNRIAID-FLLQRW GGTCHILGPDCCIEPHDWTKNITD-KIDQIIHDFVDKTLPDQGDNDNWWTG SEQ ID NO: 31 (FIL172548 Mayinga GP-647, K588L) (introduced mutation indicated by grey shading)
IPLGVIHN-STLQVSDVDKLVCRDKLSSTNQLRSVGLNLEGNG-VATDVPSATKRWGFRSGVPPKVVNYEA GEWAEN-CYNLEIKKPDGSECLPAAPDGIRGFPRCRYVHKVSG-TGPCAGDFAFHKEGAFFLYDRLASTVIY RGTTFAE-GVVAFLILPQAKKDFFSSHPLREPVNAT-EDPSSGYYSTTIRYQATGFGTNETEYLFEVDNLTYV QLESRFTPQFLLQLNETIYTSGKRSNTTGKLIWKVN-PEIDTTIGEWAFWETKKNLTRKIRSEELSFTVVSNG AKNISGQSPARTSSDPGTNTTTEDHKIMASENSSA-MVQVHSQGREAAVSHLTTLATISTSPQSLTTKPGP DNSTHNTPVYKLDISEATQVEQHHRRTDNDST-ASDTPSATTAAGPPKAENTNTSKSTDFLDPATTTSPQN HSETAGNNNTHHQDTGEESASSGKLGLITNTIAGVA-GLITGGRRTRREAIVNAQPKCNPNLHYWTTQDEG AAIGLAWIPYFGPAAEGIYIEGLMHNQDG-LICGLRQLANETTQALQLFLRATTELRTFSILNRLAID-FLLQRW GGTCHILGPDCCIEPHDWTKNITD-KIDQIIHDFVDKTLPDQGDNDNWWTG SEQ ID NO: 32 (FIL172549 Mayinga GP-647, K588M) (introduced mutation indicated by grey shading)
IPLGVIHN-STLQVSDVDKLVCRDKLSSTNQLRSVGLNLEGNG-VATDVPSATKRWGFRSGVPPKVVNYEA GEWAEN-CYNLEIKKPDGSECLPAAPDGIRGFPRCRYVHKVSG-TGPCAGDFAFHKEGAFFLYDRLASTVIY RGTTFAE-GVVAFLILPQAKKDFFSSHPLREPVNAT-EDPSSGYYSTTIRYQATGFGTNETEYLFEVDNLTYV QLESRFTPQFLLQLNETIYTSGKRSNTTGKLIWKVN-PEIDTTIGEWAFWETKKNLTRKIRSEELSFTVVSNG AKNISGQSPARTSSDPGTNTTTEDHKIMASENSSA-MVQVHSQGREAAVSHLTTLATISTSPQSLTTKPGP DNSTHNTPVYKLDISEATQVEQHHRRTDNDST-ASDTPSATTAAGPPKAENTNTSKSTDFLDPATTTSPQN HSETAGNNNTHHQDTGEESASSGKLGLITNTIAGVA-GLITGGRRTRREAIVNAQPKCNPNLHYWTTQDEG AAIGLAWIPYFGPAAEGIYIEGLMHNQDG-LICGLRQLANETTQALQLFLRATTELRTFSILNRIVI-AIDFLLQR WGGTCHILGPDCCIEPHDWTKNITD-KIDQIIHDFVDKTLPDQGDNDNWWTG SEQ ID NO: 33 (FIL172550 Mayinga GP-647, K588Y) (introduced mutation indicated by grey shading)
IPLGVIHN-STLQVSDVDKLVCRDKLSSTNQLRSVGLNLEGNG-VATDVPSATKRWGFRSGVPPKVVNYEA GEWAEN-CYNLEIKKPDGSECLPAAPDGIRGFPRCRYVHKVSG-TGPCAGDFAFHKEGAFFLYDRLASTVIY RGTTFAE-GVVAFLILPQAKKDFFSSHPLREPVNAT-EDPSSGYYSTTIRYQATGFGTNETEYLFEVDNLTYV QLESRFTPQFLLQLNETIYTSGKRSNTTGKLIWKVN-PEIDTTIGEWAFWETKKNLTRKIRSEELSFTVVSNG AKNISGQSPARTSSDPGTNTTTEDHKIMASENSSA-MVQVHSQGREAAVSHLTTLATISTSPQSLTTKPGP DNSTHNTPVYKLDISEATQVEQHHRRTDNDST-ASDTPSATTAAGPPKAENTNTSKSTDFLDPATTTSPQN HSETAGNNNTHHQDTGEESASSGKLGLITNTIAGVA-GLITGGRRTRREAIVNAQPKCNPNLHYWTTQDEG AAIGLAWIPYFGPAAEGIYIEGLMHNQDG-LICGLRQLANETTQALQLFLRATTELRTFSILNRYAID-FLLQRW GGTCHILGPDCCIEPHDWTKNITD-KIDQIIHDFVDKTLPDQGDNDNWWTG SEQ ID NO: 34 (FIL172532 Mayinga GP-647, delta mucin-like domain (4320-476), K588A) (introduced mutation indicated by grey shading)
IPLGVIHN-STLQVSDVDKLVCRDKLSSTNQLRSVGLNLEGNG-VATDVPSATKRWGFRSGVPPKVVNYEA GEWAEN-CYNLEIKKPDGSECLPAAPDGIRGFPRCRYVHKVSG-TGPCAGDFAFHKEGAFFLYDRLASTVIY RGTTFAE-GVVAFLILPQAKKDFFSSHPLREPVNAT-EDPSSGYYSTTIRYQATGFGTNETEYLFEVDNLTYV QLESRFTPQFLLQLNETIYTSGKRSNTTGKLIWKVN-PEIDTTIGEWAFWETKKNLTRKIRSEELSFTVVSNG AKNISGKLGLITNTIAGVAGLITGGRRTR-REAIVNAQPKCNPNLHYWTTQDEGAAIG-LAWIPYFGPAAEGIYI EGLMHNQDGLICGLRQLAN-ETTQALQLFLRATTELRTFSILNRAAIDFLLQRWGG-TCHILGPDCCIEPHDW TKNITD-KIDQIIHDFVDKTLPDQGDNDNWWTG SEQ ID NO: 35 (FIL172533 Mayinga GP-647, delta mucin-like domain (4320-476), K588V) (introduced mutation indicated by grey shading)
IPLGVIHN-STLQVSDVDKLVCRDKLSSTNQLRSVGLNLEGNG-VATDVPSATKRWGFRSGVPPKVVNYEA GEWAEN-CYNLEIKKPDGSECLPAAPDGIRGFPRCRYVHKVSG-TGPCAGDFAFHKEGAFFLYDRLASTVIY RGTTFAE-GVVAFLILPQAKKDFFSSHPLREPVNAT-EDPSSGYYSTTIRYQATGFGTNETEYLFEVDNLTYV QLESRFTPQFLLQLNETIYTSGKRSNTTGKLIWKVN-PEIDTTIGEWAFWETKKNLTRKIRSEELSFTVVSNG AKNISGKLGLITNTIAGVAGLITGGRRTR-REAIVNAQPKCNPNLHYWTTQDEGAAIG-LAWIPYFGPAAEGIYI EGLMHNQDGLICGLRQLAN-ETTQALQLFLRATTELRTFSILNRVAIDFLLQRWGGT-CHILGPDCCIEPHDW TKNITD-KIDQIIHDFVDKTLPDQGDNDNWWTG SEQ ID NO: 36 (FIL172534 Mayinga GP-647, delta mucin-like domain (4320-476), K588I) (introduced mutation indicated by grey shading)
IPLGVIHN-STLQVSDVDKLVCRDKLSSTNQLRSVGLNLEGNG-VATDVPSATKRWGFRSGVPPKVVNYEA GEWAEN-CYNLEIKKPDGSECLPAAPDGIRGFPRCRYVHKVSG-TGPCAGDFAFHKEGAFFLYDRLASTVIY RGTTFAE-GVVAFLILPQAKKDFFSSHPLREPVNAT-EDPSSGYYSTTIRYQATGFGTNETEYLFEVDNLTYV QLESRFTPQFLLQLNETIYTSGKRSNTTGKLIWKVN-PEIDTTIGEWAFWETKKNLTRKIRSEELSFTVVSNG AKNISGKLGLITNTIAGVAGLITGGRRTR-REAIVNAQPKCNPNLHYWTTQDEGAAIG-LAWIPYFGPAAEGIYI EGLMHNQDGLICGLRQLAN-ETTQALQLFLRATTELRTFSILNRIAIDFLLQRWGGT-CHILGPDCCIEPHDWT KNITD-KIDQIIHDFVDKTLPDQGDNDNWWTG SEQ ID NO: 37 (FIL172535 Mayinga GP-647, delta mucin-like domain (4320-476), K588L) (introduced mutation indicated by grey shading)
IPLGVIHN-STLQVSDVDKLVCRDKLSSTNQLRSVGLNLEGNG-VATDVPSATKRWGFRSGVPPKVVNYEA GEWAEN-CYNLEIKKPDGSECLPAAPDGIRGFPRCRYVHKVSG-TGPCAGDFAFHKEGAFFLYDRLASTVIY RGTTFAE-GVVAFLILPQAKKDFFSSHPLREPVNAT-EDPSSGYYSTTIRYQATGFGTNETEYLFEVDNLTYV QLESRFTPQFLLQLNETIYTSGKRSNTTGKLIWKVN-PEIDTTIGEWAFWETKKNLTRKIRSEELSFTVVSNG AKNISGKLGLITNTIAGVAGLITGGRRTR-REAIVNAQPKCNPNLHYWTTQDEGAAIG-LAWIPYFGPAAEGIYI EGLMHNQDGLICGLRQLAN-ETTQALQLFLRATTELRTFSILNRLAIDFLLQRWGGT-CHILGPDCCIEPHDW TKNITD-KIDQIIHDFVDKTLPDQGDNDNWWTG SEQ ID NO: 38 (FIL172536 Mayinga GP-647, delta mucin-like domain (4320-476), K588M) (introduced mutation indicated by grey shading)
IPLGVIHN-STLQVSDVDKLVCRDKLSSTNQLRSVGLNLEGNG-VATDVPSATKRWGFRSGVPPKVVNYEA GEWAEN-CYNLEIKKPDGSECLPAAPDGIRGFPRCRYVHKVSG-TGPCAGDFAFHKEGAFFLYDRLASTVIY RGTTFAE-GVVAFLILPQAKKDFFSSHPLREPVNAT-EDPSSGYYSTTIRYQATGFGTNETEYLFEVDNLTYV QLESRFTPQFLLQLNETIYTSGKRSNTTGKLIWKVN-PEIDTTIGEWAFWETKKNLTRKIRSEELSFTVVSNG AKNISGKLGLITNTIAGVAGLITGGRRTR-REAIVNAQPKCNPNLHYWTTQDEGAAIG-LAWIPYFGPAAEGIYI EGLMHNQDGLICGLRQLAN-ETTQALQLFLRATTELRTFSILNRMAIDFLLQRWGG-TCHILGPDCCIEPHDW TKNITD-KIDQIIHDFVDKTLPDQGDNDNWWTGH SEQ ID NO: 39 (FIL172537 Mayinga GP-647, delta mucin-like domain (4320-476), K588Y) (introduced mutation indicated by grey shading)
IPLGVIHN-STLQVSDVDKLVCRDKLSSTNQLRSVGLNLEGNG-VATDVPSATKRWGFRSGVPPKVVNYEA GEWAEN-CYNLEIKKPDGSECLPAAPDGIRGFPRCRYVHKVS-GTGPCAGDFAFHKEGAFFLYDRLASTVIY RGTTFAE-GVVAFLILPQAKKDFFSSHPLREPVNAT-EDPSSGYYSTTIRYQATGFGTNETEYLFEVDNLTYV QLESRFTPQFLLQLNETIYTSGKRSNTTGKLIWKVN-PEIDTTIGEWAFWETKKNLTRKIRSEELSFTVVSNG AKNISGKLGLITNTIAGVAGLITGGRRTR-REAIVNAQPKCNPNLHYWTTQDEGAAIG-LAWIPYFGPAAEGIYI EGLMHNQDGLICGLRQLAN-ETTQALQLFLRATTELRTFSILNRYAIDFLLQRWGG-TCHILGPDCCIEPHDW TKNITD-KIDQIIHDFVDKTLPDQGDNDNWWTG SEQ ID NO: 40 (FIL180327 Mayinga GP-647, delta mucin-like domain (4320-476), K588W) (introduced mutation indicated by grey shading)
IPLGVIHN-STLQVSDVDKLVCRDKLSSTNQLRSVGLNLEGNG-VATDVPSATKRWGFRSGVPPKVVNYEA GEWAEN-CYNLEIKKPDGSECLPAAPDGIRGFPRCRYVHKVSG-TGPCAGDFAFHKEGAFFLYDRLASTVIY RGTTFAE-GVVAFLILPQAKKDFFSSHPLREPVNAT-EDPSSGYYSTTIRYQATGFGTNETEYLFEVDNLTYV QLESRFTPQFLLQLNETIYTSGKRSNTTGKLIWKVN-PEIDTTIGEWAFWETKKNLTRKIRSEELSFTVVSNG AKNISGKLGLITNTIAGVAGLITGGRRTR-REAIVNAQPKCNPNLHYWTTQDEGAAIG-LAWIPYFGPAAEGIYI EGLMHNQDGLICGLRQLAN-ETTQALQLFLRATTELRTFSILNRWAIDFLLQRWGG-TCHILGPDCCIEPHD WTKNITD-KIDQIIHDFVDKTLPDQGDNDNWWTG SEQ ID NO: 41 (FIL171593 Marburg GP-637, (MARV) delta mucin-like domain (4255-423), H588F) (introduced mutation indicated by grey shading)
LPVLEIASNSQPQDVDSVCSGTLQKT-EDVHLMGFTLSGQKVADSPLEASKR-WAFRTGVPPKNVEYTEGE EAKTCYN-ISVTDPSGKSLLLDPPSNIRDYPKCKTVHHIQGQNP-HAQGIALHLWGAFFLYDRVASTTMYRG KVFTEGNIAAMIVNKTVHRMIFSRQGQGYRHMNLT-
STNKYWTSSNETQRNDTGCFGILQEYNSTNNQTC
PPSLKPPSLPTVTPSIHSTNTQINTAKSGTRPPIY-
FRKKRSILAKEGDIGPNLDGLINTEIDFDPIPNTE-
TIFDE SPSFNTSTNEEQHTPPNISLTFSYFPDKNGD-
TAYSGENENDCDAELRIWSVQEDDLAAGLSWIPFF-
GPGI EGLYTAGLIKNQNNLVCRLRR-
LANQTAKSLELLLRVTTEERTFSLINRFAIDFLL-
TRWGGTCKVLGPDCCIG IEDLSKNISEQIDKIRKDEQ-
KEETG SEQ ID NO: 42 (FIL171594 Marburg GP-637 (MARV) delta mucin-like domain (4255-423), H588I) (introduced mutation indicated by grey shading)
LPVLEIASNSQPQDVDSVCSGTLQKT-
EDVHLMGFTLSGQKVADSPLEASKR-
WAFRTGVPPKNVEYTEGE EAKTCYN-
ISVTDPSGKSLLLDPPSNIRDYPKCKTVHHIQGQNP-
HAQGIALHLWGAFFLYDRVASTTMYRG
KVFTEGNIAAMIVNKTVHRMIFSRQGQGYRHMNLT-
STNKYWTSSNETQRNDTGCFGILQEYNSTNNQTC
PPSLKPPSLPTVTPSIHSTNTQINTAKSGTRPPIY-
FRKKRSILAKEGDIGPNLDGLINTEIDFDPIPNTE-
TIFDE SPSFNTSTNEEQHTPPNISLTFSYFPDKNGD-
TAYSGENENDCDAELRIWSVQEDDLAAGLSWIPFFGP-
GI
EGLYTAGLIKNQNNLVCRLRR-
LANQTAKSLELLLRVTTEERTFSLINRIAIDFLL-
TRWGGTCKVLGPDCCIGI EDLSKNISEQIDKIRKDEQ-
KEETG SEQ ID NO: 43 (MARV GP (Marburg)) (ectodomain of Marburg GP, mucin-like domain underlined) (signal sequence in bold italics)
MKTIYFLISLILIQSIKTLPVLE-
IASNSQPQDVDSVCSGTLQKTEDVHLMGFTLSGQK-
VADSPLEASKRWAF RTGVPPKNVEYTEGEEAKT-
CYNISVTDPSGKSLLLDPPSNIRDYPKCKTVHHIQG-
QNPHAQGIALHLWGA FFLYDRV-
ASTTMYRGKVFTEGNIAAMIVNKTVHRMIFSRQGQ-
GYRHMNLTSTNKYWTSSNETRRNDTGC FGILQEYN-
STNNQTCSPSLKPPSLPTVTPSIHSTNTQINTAKSGTI-
NPSSDDEDLMVSGSGSGEQGPHTTL NWTE-
QKQSSTILSTPSLHPSTPQHEQN-
STNPSRHAVTEHNGTDPTTQPATLLNNTNTTPTYN-
TLKYNLS
TPSPPTRNITNNDTQRELAESEQTNAQLNTTPDPTEN-
PTTAQDTNSTTNITMTTSDITSK-
HPTNSSPDSSP TTRPPIYFRKKRSIFWKEGDIFPFLDG-
LINTEIDFDPIPNTETIFDESPSFNTSTNEEQHTPPN-
ISLTFSYFPD KNGDTAYSGENENDCDAEL-
RIWSVQEDDLAAGLSWIPFFGPGIEGLYTAGLIKNQ-
NNLVCRLRRLANQTA KSLELLLRVT-
TEERTFSLINRHAIDFLLTRWGGTCKVLGPDC-
CIGIEDLSKNISEQIDKIRKDEQKEETG SEQ ID NO: 44 Signal peptide of Ebola GP
MGVTGILQLPRDRFKRTSFFLWVIILFQRTFS SEQ ID NO: 45 Signal peptide of Marburg GP
MKTIYFLISLILIQSIKT

REFERENCES

Sanchez, A. et al. 1996 PNAS USA 93:3602-3607
Friedrich et al., Viruses. 2012 September; 4(9):1619-50
Wang et al. Cell. 2016 Jan. 14; 164(1-2):258-268
Bornholdt et al. MBio. 2016 Feb. 23; 7(1):e02154-15
Pallesen et al. Nat Microbiol. 2016 Aug. 8; 1(9):16128
Lee et al. Nature. 2008 Jul. 10; 454(7201):177-82
Sanchez et al. Proc Natl Acad Sci USA. 1996 Apr. 16; 93(8):3602-7
Eglen et al. Curr. Chem. Genomics, 2008, 25(1): 2-10
WO 2007/104792
Abbink et al., (2007) Virol. 81(9): 4654-63
Kushnir et al., Vaccine. 2012 Dec. 17; 31(1):58-83
Bale et al, J Virol. 2017 Jul. 27; 91(16). pii: e00443-17
Zhao L, et al (2014) Vaccine 32: 327-337
López-Sagaseta et al, Comput Struct Biotechnol J. 2015 Nov. 26; 14:58-68
Zhao et al. Nature. 2016 Jul. 7; 535(7610):169-172
Hashiguchi et al. Cell, 2015 Feb. 26; 160:904-912
US 2015/0291935
WO 2014/124301
US 2016/0122392
WO 2017/037196

---

What is claimed is:

1. A recombinant glycoprotein obtained by replacing an amino acid residue of a Filovirus glycoprotein with a non-charged amino acid residue,
   wherein the Filovirus glycoprotein is selected from the group consisting of:
   1) A Zaire Ebolavirus Mayinga glycoprotein comprising the amino acid sequence of SEQ ID NO: 2 or a Zaire Ebolavirus Mayinga glycoprotein with a deletion between amino acid residues 288 and 444, comprising the amino acid sequence of SEQ ID NO: 6;
      wherein the recombinant glycoprotein is obtained by replacing a lysine at position 556 with a hydrophobic amino acid residue selected from the group consisting of F, I, L, M, V, W, and Y;
      wherein the numbering of the positions is according to the numbering of the glycoprotein of SEQ ID NO: 2;
   2) A Zaire Ebolavirus Makona GP glycoprotein comprising the amino acid sequence of SEQ ID NO: 10 or a Zaire Ebolavirus Makona GP glycoprotein with a deletion between amino acid residues 282 and 440, comprising the amino acid sequence of SEQ ID NO: 14;
      wherein the recombinant glycoprotein is obtained by replacing a lysine at position 556 with a hydrophobic amino acid residue selected from the group consisting of F, I, L, M, V, W, and Y;
      wherein the numbering of the positions is according to the numbering of the glycoprotein of SEQ ID NO: 10;
   3) A Zaire Ebolavirus Kikwit glycoprotein comprising the amino acid sequence of SEQ ID NO: 19 or a Zaire Ebolavirus Kikwit glycoprotein with a deletion between amino acid residues 282 and 440, comprising the amino acid sequence of SEQ ID NO: 23;
      wherein a lysine at position 556 has been replaced with a hydrophobic amino acid residue selected from the group consisting of F, I, L, M, V, W, and Y;
      wherein the numbering of the positions is according to the numbering of the glycoprotein of SEQ ID NO: 19; and
   4) a Marburg glycoprotein with a deleted mucin-like domain, comprising the amino acid sequence of SEQ ID NO: 27,
      wherein a histidine at position 402 has been replaced with a hydrophobic amino acid residue selected from the group consisting of F, I, L, M, V, W, and Y;
      wherein the numbering of the positions is according to the numbering of the glycoprotein of SEQ ID NO: 27.

2. A recombinant Filovirus glycoprotein according to claim 1, wherein the non-charged amino acid residue is a hydrophobic amino acid residue selected from the group of F, I, L, M, V, and Y.

3. A recombinant Filovirus glycoprotein, comprising a Zaire Ebolavirus Mayinga glycoprotein comprising the amino acid sequence of SEQ ID NO: 2 or a Zaire Ebolavirus Mayinga glycoprotein with a deletion between amino acid residues 288 and 444, comprising the amino acid sequence of SEQ ID NO: 6;
   wherein the recombinant glycoprotein is obtained by replacing a lysine at position 556 with a hydrophobic amino acid residue selected from the group consisting of F, I, L, M, V, W, and Y;
   wherein the numbering of the positions is according to the numbering of the glycoprotein of SEQ ID NO: 2.

4. A recombinant Filovirus glycoprotein according to claim 2, wherein the hydrophobic amino acid residue is F.

5. A recombinant Filovirus glycoprotein according to claim 3, further comprising an amino acid residue P at position 545 and/or 547.

6. A trimeric complex comprising a noncovalent oligomer of three of the recombinant glycoproteins of claim 1.

7. A particle, displaying on its surface the recombinant glycoprotein of claim 1, wherein the particle is a liposome, a virus-like particle (VLP), a nanoparticle, a virosome, or an exosome.

8. An isolated nucleic acid molecule encoding the recombinant Filovirus glycoprotein of claim 1.

9. A vector comprising the isolated nucleic acid molecule of claim 8 operably linked to a promoter.

10. The vector of claim 9, wherein the vector is an adenovirus vector.

11. A host cell comprising the isolated nucleic acid molecule of claim 8.

12. A method of producing a recombinant Filovirus glycoprotein, comprising growing the host cell of claim 11 under conditions suitable for production of the recombinant Filovirus glycoprotein.

13. A method of improving the trimer formation of a Filovirus glycoprotein, the method comprising substituting a lysine amino acid residue at position 556 of the Filovirus glycoprotein for a hydrophobic amino acid residue selected from the group consisting of F, I, L, M, V, W, and Y, wherein:
the Filovirus glycoprotein is a Zaire Ebolavirus Mayinga glycoprotein comprising the amino acid sequence of SEQ ID NO: 2 or a Zaire Ebolavirus Mayinga glycoprotein with a deletion between amino acid residues 288 and 444, comprising the amino acid sequence of SEQ ID NO: 6; and
the numbering of the positions is according to the numbering of the glycoprotein of SEQ ID NO: 2;
wherein the substitution at position 556 increases the percentage of trimer formation.

14. A method according to claim 13, the method further comprising substituting at least one of an amino acid residue at position 545 and an amino acid residue at position 547 of the Zaire Ebolavirus Mayinga glycoprotein for a P residue.

15. A trimeric complex comprising a noncovalent oligomer of three of the recombinant Filovirus glycoproteins of claim 3.

16. A particle, displaying on its surface the trimeric complex of claim 6, wherein the particle is a liposome, a virus-like particle (VLP), a nanoparticle, a virosome, or an exosome.

17. A host cell comprising the vector of claim 9.

18. A host cell comprising the vector of claim 10.

19. A composition comprising:
a)
  a recombinant Filovirus glycoprotein, comprising a Zaire Ebolavirus Mayinga glycoprotein comprising the amino acid sequence of SEQ ID NO: 2 or a Zaire Ebolavirus Mayinga glycoprotein with a deletion between amino acid residues 288 and 444, comprising the amino acid sequence of SEQ ID NO: 6;
  wherein the recombinant glycoprotein is obtained by replacing a lysine at position 556 with a hydrophobic amino acid residue selected from the group consisting of F, I, L, M, V, W, and Y;
  wherein the numbering of the positions is according to the numbering of the glycoprotein of SEQ ID NO: 2;
and
b) a pharmaceutically acceptable carrier.

20. A composition comprising:
a) a trimeric complex comprising a noncovalent oligomer of three recombinant Filovirus glycoproteins, each recombinant Filovirus glycoprotein comprising a Zaire Ebolavirus Mayinga glycoprotein comprising the amino acid sequence of SEQ ID NO: 2 or a Zaire Ebolavirus Mayinga glycoprotein with a deletion between amino acid residues 288 and 444, comprising the amino acid sequence of SEQ ID NO: 6;
  wherein the recombinant glycoprotein is obtained by replacing a lysine at position 556 with a hydrophobic amino acid residue selected from the group consisting of F, I, L, M, V, W, and Y;
  wherein the numbering of the positions is according to the numbering of the glycoprotein of SEQ ID NO: 2;
and
b) a pharmaceutically acceptable carrier.

21. A composition comprising:
a) a particle displaying on its surface a recombinant Filovirus glycoprotein comprising a Zaire Ebolavirus Mayinga glycoprotein comprising the amino acid sequence of SEQ ID NO: 2 or a Zaire Ebolavirus Mayinga glycoprotein with a deletion between amino acid residues 288 and 444, comprising the amino acid sequence of SEQ ID NO: 6;
  wherein the recombinant glycoprotein is obtained by replacing a lysine at position 556 with a hydrophobic amino acid residue selected from the group consisting of F, I, L, M, V, W, and Y;
  wherein the numbering of the positions is according to the numbering of the glycoprotein of SEQ ID NO: 2
  wherein the particle is a liposome, a virus-like particle (VLP), a nanoparticle, a virosome, or an exosome; and
a) a pharmaceutically acceptable carrier.

* * * * *

SEQUENCE LISTING

```
<160> NUMBER OF SEQ ID NOS: 46

<210> SEQ ID NO 1
<211> LENGTH: 676
<212> TYPE: PRT
<213> ORGANISM: Zaire ebolavirus

<400> SEQUENCE: 1

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80
```

-continued

Ser Ala Thr Lys Arg Trp Gly Phe Arg Ser Gly Val Pro Lys Val
            85                  90                  95

Val Asn Tyr Glu Ala Gly Trp Ala Glu Asn Cys Tyr Asn Leu Glu
            100                 105                 110

Ile Lys Lys Pro Asp Gly Ser Glu Cys Leu Pro Ala Ala Pro Asp Gly
            115                 120                 125

Ile Arg Gly Phe Pro Arg Cys Arg Tyr Val His Lys Val Ser Gly Thr
130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
            165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
            195                 200                 205

Pro Ser Ser Gly Tyr Tyr Ser Thr Thr Ile Arg Tyr Gln Ala Thr Gly
            210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
            245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
            275                 280                 285

Ala Phe Trp Glu Thr Lys Lys Asn Leu Thr Arg Lys Ile Arg Ser Glu
            290                 295                 300

Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
            325                 330                 335

Glu Asp His Lys Ile Met Ala Ser Glu Asn Ser Ser Ala Met Val Gln
            340                 345                 350

Val His Ser Gln Gly Arg Glu Ala Ala Val Ser His Leu Thr Thr Leu
            355                 360                 365

Ala Thr Ile Ser Thr Ser Pro Gln Ser Leu Thr Thr Lys Pro Gly Pro
            370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
            405                 410                 415

Ala Ser Asp Thr Pro Ser Ala Thr Thr Ala Ala Gly Pro Pro Lys Ala
            420                 425                 430

Glu Asn Thr Asn Thr Ser Lys Ser Thr Asp Phe Leu Asp Pro Ala Thr
            435                 440                 445

Thr Thr Ser Pro Gln Asn His Ser Glu Thr Ala Gly Asn Asn Asn Thr
            450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
            485                 490                 495

```
Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
            515                 520                 525

Leu Ala Trp Ile Pro Tyr Phe Gly Pro Ala Ala Glu Gly Ile Tyr Ile
            530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
            565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
            595                 600                 605

Cys Ile Glu Pro His Asp Trp Thr Lys Asn Ile Thr Asp Lys Ile Asp
            610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
            645                 650                 655

Gly Val Thr Gly Val Ile Ile Ala Val Ile Ala Leu Phe Cys Ile Cys
            660                 665                 670

Lys Phe Val Phe
            675

<210> SEQ ID NO 2
<211> LENGTH: 615
<212> TYPE: PRT
<213> ORGANISM: Zaire ebolavirus

<400> SEQUENCE: 2

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190
```

```
Phe Gly Thr Asn Glu Thr Glu Tyr Leu Phe Glu Val Asp Asn Leu Thr
            195                 200                 205

Tyr Val Gln Leu Glu Ser Arg Phe Thr Pro Gln Phe Leu Leu Gln Leu
    210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
                260                 265                 270

Glu Leu Ser Phe Thr Val Val Ser Asn Gly Ala Lys Asn Ile Ser Gly
            275                 280                 285

Gln Ser Pro Ala Arg Thr Ser Ser Asp Pro Gly Thr Asn Thr Thr Thr
        290                 295                 300

Glu Asp His Lys Ile Met Ala Ser Glu Asn Ser Ser Ala Met Val Gln
305                 310                 315                 320

Val His Ser Gln Gly Arg Glu Ala Ala Val Ser His Leu Thr Thr Leu
                325                 330                 335

Ala Thr Ile Ser Thr Ser Pro Gln Ser Leu Thr Thr Lys Pro Gly Pro
                340                 345                 350

Asp Asn Ser Thr His Asn Thr Pro Val Tyr Lys Leu Asp Ile Ser Glu
            355                 360                 365

Ala Thr Gln Val Glu Gln His His Arg Arg Thr Asp Asn Asp Ser Thr
    370                 375                 380

Ala Ser Asp Thr Pro Ser Ala Thr Thr Ala Ala Gly Pro Pro Lys Ala
385                 390                 395                 400

Glu Asn Thr Asn Thr Ser Lys Ser Thr Asp Phe Leu Asp Pro Ala Thr
                405                 410                 415

Thr Thr Ser Pro Gln Asn His Ser Glu Thr Ala Gly Asn Asn Asn Thr
                420                 425                 430

His His Gln Asp Thr Gly Glu Glu Ser Ala Ser Ser Gly Lys Leu Gly
        435                 440                 445

Leu Ile Thr Asn Thr Ile Ala Gly Val Ala Gly Leu Ile Thr Gly Gly
    450                 455                 460

Arg Arg Thr Arg Arg Glu Ala Ile Val Asn Ala Gln Pro Lys Cys Asn
465                 470                 475                 480

Pro Asn Leu His Tyr Trp Thr Thr Gln Asp Glu Gly Ala Ala Ile Gly
                485                 490                 495

Leu Ala Trp Ile Pro Tyr Phe Gly Pro Ala Ala Glu Gly Ile Tyr Ile
            500                 505                 510

Glu Gly Leu Met His Asn Gln Asp Gly Leu Ile Cys Gly Leu Arg Gln
            515                 520                 525

Leu Ala Asn Glu Thr Thr Gln Ala Leu Gln Leu Phe Leu Arg Ala Thr
        530                 535                 540

Thr Glu Leu Arg Thr Phe Ser Ile Leu Asn Arg Lys Ala Ile Asp Phe
545                 550                 555                 560

Leu Leu Gln Arg Trp Gly Gly Thr Cys His Ile Leu Gly Pro Asp Cys
                565                 570                 575

Cys Ile Glu Pro His Asp Trp Thr Lys Asn Ile Thr Asp Lys Ile Asp
            580                 585                 590

Gln Ile Ile His Asp Phe Val Asp Lys Thr Leu Pro Asp Gln Gly Asp
            595                 600                 605
```

```
Asn Asp Asn Trp Trp Thr Gly
    610             615

<210> SEQ ID NO 3
<211> LENGTH: 615
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65              70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
    210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270

Glu Leu Ser Phe Thr Val Val Ser Asn Gly Ala Lys Asn Ile Ser Gly
        275                 280                 285

Gln Ser Pro Ala Arg Thr Ser Ser Asp Pro Gly Thr Asn Thr Thr Thr
    290                 295                 300

Glu Asp His Lys Ile Met Ala Ser Glu Asn Ser Ser Ala Met Val Gln
305                 310                 315                 320

Val His Ser Gln Gly Arg Glu Ala Ala Val Ser His Leu Thr Thr Leu
                325                 330                 335
```

```
Ala Thr Ile Ser Thr Ser Pro Gln Ser Leu Thr Thr Lys Pro Gly Pro
            340                 345                 350

Asp Asn Ser Thr His Asn Thr Pro Val Tyr Lys Leu Asp Ile Ser Glu
            355                 360                 365

Ala Thr Gln Val Glu Gln His His Arg Arg Thr Asp Asn Asp Ser Thr
370                 375                 380

Ala Ser Asp Thr Pro Ser Ala Thr Thr Ala Ala Gly Pro Pro Lys Ala
385                 390                 395                 400

Glu Asn Thr Asn Thr Ser Lys Ser Thr Asp Phe Leu Asp Pro Ala Thr
            405                 410                 415

Thr Thr Ser Pro Gln Asn His Ser Glu Thr Ala Gly Asn Asn Asn Thr
            420                 425                 430

His His Gln Asp Thr Gly Glu Glu Ser Ala Ser Ser Gly Lys Leu Gly
            435                 440                 445

Leu Ile Thr Asn Thr Ile Ala Gly Val Ala Gly Leu Ile Thr Gly Gly
            450                 455                 460

Arg Arg Thr Arg Arg Glu Ala Ile Val Asn Ala Gln Pro Lys Cys Asn
465                 470                 475                 480

Pro Asn Leu His Tyr Trp Thr Thr Gln Asp Glu Gly Ala Ala Ile Gly
            485                 490                 495

Leu Ala Trp Ile Pro Tyr Phe Gly Pro Ala Ala Glu Gly Ile Tyr Ile
            500                 505                 510

Glu Gly Leu Met His Asn Gln Asp Gly Leu Ile Cys Gly Leu Arg Gln
            515                 520                 525

Leu Ala Asn Glu Thr Thr Gln Ala Leu Gln Leu Phe Leu Arg Ala Thr
            530                 535                 540

Pro Glu Leu Arg Thr Phe Ser Ile Leu Asn Arg Lys Ala Ile Asp Phe
545                 550                 555                 560

Leu Leu Gln Arg Trp Gly Gly Thr Cys His Ile Leu Gly Pro Asp Cys
            565                 570                 575

Cys Ile Glu Pro His Asp Trp Thr Lys Asn Ile Thr Asp Lys Ile Asp
            580                 585                 590

Gln Ile Ile His Asp Phe Val Asp Lys Thr Leu Pro Asp Gln Gly Asp
            595                 600                 605

Asn Asp Asn Trp Trp Thr Gly
610                 615

<210> SEQ ID NO 4
<211> LENGTH: 615
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
            35                  40                  45

Ser Ala Thr Lys Arg Trp Gly Phe Arg Ser Gly Val Pro Pro Lys Val
50                  55                  60
```

```
Val Asn Tyr Glu Ala Gly Glu Trp Ala Glu Asn Cys Tyr Asn Leu Glu
 65                  70                  75                  80

Ile Lys Lys Pro Asp Gly Ser Glu Cys Leu Pro Ala Ala Pro Asp Gly
                 85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
    210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270

Glu Leu Ser Phe Thr Val Val Ser Asn Gly Ala Lys Asn Ile Ser Gly
        275                 280                 285

Gln Ser Pro Ala Arg Thr Ser Ser Asp Pro Gly Thr Asn Thr Thr Thr
    290                 295                 300

Glu Asp His Lys Ile Met Ala Ser Glu Asn Ser Ser Ala Met Val Gln
305                 310                 315                 320

Val His Ser Gln Gly Arg Glu Ala Ala Val Ser His Leu Thr Thr Leu
                325                 330                 335

Ala Thr Ile Ser Thr Ser Pro Gln Ser Leu Thr Thr Lys Pro Gly Pro
            340                 345                 350

Asp Asn Ser Thr His Asn Thr Pro Val Tyr Lys Leu Asp Ile Ser Glu
        355                 360                 365

Ala Thr Gln Val Glu Gln His His Arg Arg Thr Asp Asn Asp Ser Thr
    370                 375                 380

Ala Ser Asp Thr Pro Ser Ala Thr Thr Ala Ala Gly Pro Pro Lys Ala
385                 390                 395                 400

Glu Asn Thr Asn Thr Ser Lys Ser Thr Asp Phe Leu Asp Pro Ala Thr
                405                 410                 415

Thr Thr Ser Pro Gln Asn His Ser Glu Thr Ala Gly Asn Asn Asn Thr
            420                 425                 430

His His Gln Asp Thr Gly Glu Glu Ser Ala Ser Ser Gly Lys Leu Gly
        435                 440                 445

Leu Ile Thr Asn Thr Ile Ala Gly Val Ala Gly Leu Ile Thr Gly Gly
    450                 455                 460

Arg Arg Thr Arg Arg Glu Ala Ile Val Asn Ala Gln Pro Lys Cys Asn
465                 470                 475                 480
```

```
Pro Asn Leu His Tyr Trp Thr Thr Gln Asp Glu Gly Ala Ala Ile Gly
            485                 490                 495

Leu Ala Trp Ile Pro Tyr Phe Gly Pro Ala Ala Glu Gly Ile Tyr Ile
            500                 505                 510

Glu Gly Leu Met His Asn Gln Asp Gly Leu Ile Cys Gly Leu Arg Gln
            515                 520                 525

Leu Ala Asn Glu Thr Thr Gln Ala Leu Gln Leu Phe Leu Arg Ala Thr
            530                 535                 540

Thr Glu Leu Arg Thr Phe Ser Ile Leu Asn Arg Phe Ala Ile Asp Phe
545                 550                 555                 560

Leu Leu Gln Arg Trp Gly Gly Thr Cys His Ile Leu Gly Pro Asp Cys
            565                 570                 575

Cys Ile Glu Pro His Asp Trp Thr Lys Asn Ile Thr Asp Lys Ile Asp
            580                 585                 590

Gln Ile Ile His Asp Phe Val Asp Lys Thr Leu Pro Asp Gln Gly Asp
            595                 600                 605

Asn Asp Asn Trp Trp Thr Gly
            610                 615

<210> SEQ ID NO 5
<211> LENGTH: 615
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
            85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
            115                 120                 125

Leu Tyr Asp Arg Leu Ala Ser Thr Val Ile Tyr Arg Gly Thr Thr Phe
            130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
            165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
            195                 200                 205
```

```
Tyr Val Gln Leu Glu Ser Arg Phe Thr Pro Gln Phe Leu Leu Gln Leu
210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
                260                 265                 270

Glu Leu Ser Phe Thr Val Val Ser Asn Gly Ala Lys Asn Ile Ser Gly
                275                 280                 285

Gln Ser Pro Ala Arg Thr Ser Ser Asp Pro Gly Thr Asn Thr Thr Thr
290                 295                 300

Glu Asp His Lys Ile Met Ala Ser Glu Asn Ser Ser Ala Met Val Gln
305                 310                 315                 320

Val His Ser Gln Gly Arg Glu Ala Ala Val Ser His Leu Thr Thr Leu
                325                 330                 335

Ala Thr Ile Ser Thr Ser Pro Gln Ser Leu Thr Thr Lys Pro Gly Pro
                340                 345                 350

Asp Asn Ser Thr His Asn Thr Pro Val Tyr Lys Leu Asp Ile Ser Glu
                355                 360                 365

Ala Thr Gln Val Glu Gln His His Arg Arg Thr Asp Asn Asp Ser Thr
370                 375                 380

Ala Ser Asp Thr Pro Ser Ala Thr Thr Ala Ala Gly Pro Pro Lys Ala
385                 390                 395                 400

Glu Asn Thr Asn Thr Ser Lys Ser Thr Asp Phe Leu Asp Pro Ala Thr
                405                 410                 415

Thr Thr Ser Pro Gln Asn His Ser Glu Thr Ala Gly Asn Asn Asn Thr
                420                 425                 430

His His Gln Asp Thr Gly Glu Glu Ser Ala Ser Ser Gly Lys Leu Gly
                435                 440                 445

Leu Ile Thr Asn Thr Ile Ala Gly Val Ala Gly Leu Ile Thr Gly Gly
                450                 455                 460

Arg Arg Thr Arg Arg Glu Ala Ile Val Asn Ala Gln Pro Lys Cys Asn
465                 470                 475                 480

Pro Asn Leu His Tyr Trp Thr Thr Gln Asp Glu Gly Ala Ala Ile Gly
                485                 490                 495

Leu Ala Trp Ile Pro Tyr Phe Gly Pro Ala Ala Glu Gly Ile Tyr Ile
                500                 505                 510

Glu Gly Leu Met His Asn Gln Asp Gly Leu Ile Cys Gly Leu Arg Gln
                515                 520                 525

Leu Ala Asn Glu Thr Thr Gln Ala Leu Gln Leu Phe Leu Arg Ala Thr
530                 535                 540

Pro Glu Leu Arg Thr Phe Ser Ile Leu Asn Arg Lys Ala Ile Asp Phe
545                 550                 555                 560

Leu Leu Gln Arg Trp Gly Gly Thr Cys His Ile Leu Gly Pro Asp Cys
                565                 570                 575

Cys Ile Glu Pro His Asp Trp Thr Lys Asn Ile Thr Asp Lys Ile Asp
                580                 585                 590

Gln Ile Ile His Asp Phe Val Asp Lys Thr Leu Pro Asp Gln Gly Asp
                595                 600                 605

Asn Asp Asn Trp Trp Thr Gly
610                 615
```

-continued

```
<210> SEQ ID NO 6
<211> LENGTH: 458
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
                20                  25                  30

Ser Val Gly Leu Asn Leu Glu Gly Asn Gly Val Ala Thr Asp Val Pro
            35                  40                  45

Ser Ala Thr Lys Arg Trp Gly Phe Arg Ser Gly Val Pro Pro Lys Val
        50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
    210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270

Glu Leu Ser Phe Thr Val Val Ser Asn Gly Ala Lys Asn Ile Ser Gly
        275                 280                 285

Lys Leu Gly Leu Ile Thr Asn Thr Ile Ala Gly Val Ala Gly Leu Ile
    290                 295                 300

Thr Gly Gly Arg Arg Thr Arg Arg Glu Ala Ile Val Asn Ala Gln Pro
305                 310                 315                 320

Lys Cys Asn Pro Asn Leu His Tyr Trp Thr Thr Gln Asp Glu Gly Ala
                325                 330                 335

Ala Ile Gly Leu Ala Trp Ile Pro Tyr Phe Gly Pro Ala Ala Glu Gly
            340                 345                 350

Ile Tyr Ile Glu Gly Leu Met His Asn Gln Asp Gly Leu Ile Cys Gly
        355                 360                 365
```

```
Leu Arg Gln Leu Ala Asn Glu Thr Thr Gln Ala Leu Gln Leu Phe Leu
    370                 375                 380

Arg Ala Thr Thr Glu Leu Arg Thr Phe Ser Ile Leu Asn Arg Lys Ala
385                 390                 395                 400

Ile Asp Phe Leu Leu Gln Arg Trp Gly Gly Thr Cys His Ile Leu Gly
                405                 410                 415

Pro Asp Cys Cys Ile Glu Pro His Asp Trp Thr Lys Asn Ile Thr Asp
                420                 425                 430

Lys Ile Asp Gln Ile Ile His Asp Phe Val Asp Lys Thr Leu Pro Asp
            435                 440                 445

Gln Gly Asp Asn Asp Asn Trp Trp Thr Gly
    450                 455
```

<210> SEQ ID NO 7
<211> LENGTH: 458
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

```
Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
                20                  25                  30

Ser Val Gly Leu Asn Leu Glu Gly Asn Gly Val Ala Thr Asp Val Pro
            35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
                100                 105                 110

Gly Pro Cys Ala Gly Asp Phe Ala Phe His Lys Glu Gly Ala Phe Phe
            115                 120                 125

Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
    195                 200                 205

Tyr Val Gln Leu Glu Ser Arg Phe Thr Pro Gln Phe Leu Leu Gln Leu
    210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255
```

```
Ala Phe Trp Glu Thr Lys Lys Asn Leu Thr Arg Lys Ile Arg Ser Glu
            260                 265                 270

Glu Leu Ser Phe Thr Val Val Ser Asn Gly Ala Lys Asn Ile Ser Gly
        275                 280                 285

Lys Leu Gly Leu Ile Thr Asn Thr Ile Ala Gly Val Ala Gly Leu Ile
    290                 295                 300

Thr Gly Gly Arg Arg Thr Arg Arg Glu Ala Ile Val Asn Ala Gln Pro
305                 310                 315                 320

Lys Cys Asn Pro Asn Leu His Tyr Trp Thr Thr Gln Asp Glu Gly Ala
                325                 330                 335

Ala Ile Gly Leu Ala Trp Ile Pro Tyr Phe Gly Pro Ala Ala Glu Gly
            340                 345                 350

Ile Tyr Ile Glu Gly Leu Met His Asn Gln Asp Gly Leu Ile Cys Gly
        355                 360                 365

Leu Arg Gln Leu Ala Asn Glu Thr Thr Gln Ala Leu Gln Leu Phe Leu
    370                 375                 380

Arg Ala Thr Pro Glu Leu Arg Thr Phe Ser Ile Leu Asn Arg Lys Ala
385                 390                 395                 400

Ile Asp Phe Leu Leu Gln Arg Trp Gly Gly Thr Cys His Ile Leu Gly
                405                 410                 415

Pro Asp Cys Cys Ile Glu Pro His Asp Trp Thr Lys Asn Ile Thr Asp
            420                 425                 430

Lys Ile Asp Gln Ile Ile His Asp Phe Val Asp Lys Thr Leu Pro Asp
        435                 440                 445

Gln Gly Asp Asn Asp Asn Trp Trp Thr Gly
    450                 455

<210> SEQ ID NO 8
<211> LENGTH: 458
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
    130                 135                 140
```

-continued

```
Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
            165                 170                 175

Pro Ser Ser Gly Tyr Tyr Ser Thr Thr Ile Arg Tyr Gln Ala Thr Gly
        180                 185                 190

Phe Gly Thr Asn Glu Thr Glu Tyr Leu Phe Glu Val Asp Asn Leu Thr
    195                 200                 205

Tyr Val Gln Leu Glu Ser Arg Phe Thr Pro Gln Phe Leu Leu Gln Leu
210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
            245                 250                 255

Ala Phe Trp Glu Thr Lys Lys Asn Leu Thr Arg Lys Ile Arg Ser Glu
        260                 265                 270

Glu Leu Ser Phe Thr Val Val Ser Asn Gly Ala Lys Asn Ile Ser Gly
    275                 280                 285

Lys Leu Gly Leu Ile Thr Asn Thr Ile Ala Gly Val Ala Gly Leu Ile
290                 295                 300

Thr Gly Gly Arg Arg Thr Arg Arg Glu Ala Ile Val Asn Ala Gln Pro
305                 310                 315                 320

Lys Cys Asn Pro Asn Leu His Tyr Trp Thr Thr Gln Asp Glu Gly Ala
            325                 330                 335

Ala Ile Gly Leu Ala Trp Ile Pro Tyr Phe Gly Pro Ala Ala Glu Gly
        340                 345                 350

Ile Tyr Ile Glu Gly Leu Met His Asn Gln Asp Gly Leu Ile Cys Gly
    355                 360                 365

Leu Arg Gln Leu Ala Asn Glu Thr Thr Gln Ala Leu Gln Leu Phe Leu
370                 375                 380

Arg Ala Thr Thr Glu Leu Arg Thr Phe Ser Ile Leu Asn Arg Phe Ala
385                 390                 395                 400

Ile Asp Phe Leu Leu Gln Arg Trp Gly Gly Thr Cys His Ile Leu Gly
            405                 410                 415

Pro Asp Cys Cys Ile Glu Pro His Asp Trp Thr Lys Asn Ile Thr Asp
        420                 425                 430

Lys Ile Asp Gln Ile Ile His Asp Phe Val Asp Lys Thr Leu Pro Asp
    435                 440                 445

Gln Gly Asp Asn Asp Asn Trp Trp Thr Gly
450                 455
```

<210> SEQ ID NO 9
<211> LENGTH: 458
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

```
Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30
```

```
Ser Val Gly Leu Asn Leu Glu Gly Asn Gly Val Ala Thr Asp Val Pro
        35                  40                  45
Ser Ala Thr Lys Arg Trp Gly Phe Arg Ser Gly Val Pro Pro Lys Val
 50                  55                  60
Val Asn Tyr Glu Ala Gly Glu Trp Ala Glu Asn Cys Tyr Asn Leu Glu
 65                  70                  75                  80
Ile Lys Lys Pro Asp Gly Ser Glu Cys Leu Pro Ala Ala Pro Asp Gly
                 85                  90                  95
Ile Arg Gly Phe Pro Arg Cys Arg Tyr Val His Lys Val Ser Gly Thr
                100                 105                 110
Gly Pro Cys Ala Gly Asp Phe Ala Phe His Lys Glu Gly Ala Phe Phe
        115                 120                 125
Leu Tyr Asp Arg Leu Ala Ser Thr Val Ile Tyr Arg Gly Thr Thr Phe
    130                 135                 140
Ala Glu Gly Val Val Ala Phe Leu Ile Leu Pro Gln Ala Lys Lys Asp
145                 150                 155                 160
Phe Phe Ser Ser His Pro Leu Arg Glu Pro Val Asn Ala Thr Glu Asp
                165                 170                 175
Pro Ser Ser Gly Tyr Tyr Ser Thr Thr Ile Arg Tyr Gln Ala Thr Gly
                180                 185                 190
Phe Gly Thr Asn Glu Thr Glu Tyr Leu Phe Glu Val Asp Asn Leu Thr
        195                 200                 205
Tyr Val Gln Leu Glu Ser Arg Phe Thr Pro Gln Phe Leu Leu Gln Leu
    210                 215                 220
Asn Glu Thr Ile Tyr Thr Ser Gly Lys Arg Ser Asn Thr Thr Gly Lys
225                 230                 235                 240
Leu Ile Trp Lys Val Asn Pro Glu Ile Asp Thr Thr Ile Gly Glu Trp
                245                 250                 255
Ala Phe Trp Glu Thr Lys Lys Asn Leu Thr Arg Lys Ile Arg Ser Glu
                260                 265                 270
Glu Leu Ser Phe Thr Val Val Ser Asn Gly Ala Lys Asn Ile Ser Gly
        275                 280                 285
Lys Leu Gly Leu Ile Thr Asn Thr Ile Ala Gly Val Ala Gly Leu Ile
    290                 295                 300
Thr Gly Gly Arg Arg Thr Arg Arg Glu Ala Ile Val Asn Ala Gln Pro
305                 310                 315                 320
Lys Cys Asn Pro Asn Leu His Tyr Trp Thr Thr Gln Asp Glu Gly Ala
                325                 330                 335
Ala Ile Gly Leu Ala Trp Ile Pro Tyr Phe Gly Pro Ala Ala Glu Gly
        340                 345                 350
Ile Tyr Ile Glu Gly Leu Met His Asn Gln Asp Gly Leu Ile Cys Gly
    355                 360                 365
Leu Arg Gln Leu Ala Asn Glu Thr Thr Gln Ala Leu Gln Leu Phe Leu
370                 375                 380
Arg Ala Thr Pro Glu Leu Arg Thr Phe Ser Ile Leu Asn Arg Phe Ala
385                 390                 395                 400
Ile Asp Phe Leu Leu Gln Arg Trp Gly Gly Thr Cys His Ile Leu Gly
                405                 410                 415
Pro Asp Cys Cys Ile Glu Pro His Asp Trp Thr Lys Asn Ile Thr Asp
                420                 425                 430
Lys Ile Asp Gln Ile Ile His Asp Phe Val Asp Lys Thr Leu Pro Asp
        435                 440                 445
```

```
Gln Gly Asp Asn Asp Asn Trp Trp Thr Gly
    450                 455
```

<210> SEQ ID NO 10
<211> LENGTH: 615
<212> TYPE: PRT
<213> ORGANISM: Zaire ebolavirus

<400> SEQUENCE: 10

```
Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Val Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
    210                 215                 220

Asn Glu Thr Ile Tyr Ala Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270

Glu Leu Ser Phe Thr Ala Val Ser Asn Gly Pro Lys Asn Ile Ser Gly
        275                 280                 285

Gln Ser Pro Ala Arg Thr Ser Ser Asp Pro Glu Thr Asn Thr Thr Asn
    290                 295                 300

Glu Asp His Lys Ile Met Ala Ser Glu Asn Ser Ser Ala Met Val Gln
305                 310                 315                 320

Val His Ser Gln Gly Arg Lys Ala Ala Val Ser His Leu Thr Thr Leu
                325                 330                 335

Ala Thr Ile Ser Thr Ser Pro Gln Pro Pro Thr Thr Lys Thr Gly Pro
            340                 345                 350
```

-continued

```
Asp Asn Ser Thr His Asn Thr Pro Val Tyr Lys Leu Asp Ile Ser Glu
            355                 360                 365

Ala Thr Gln Val Gly Gln His His Arg Arg Ala Asp Asn Asp Ser Thr
370                 375                 380

Ala Ser Asp Thr Pro Pro Ala Thr Thr Ala Ala Gly Pro Leu Lys Ala
385                 390                 395                 400

Glu Asn Thr Asn Thr Ser Lys Ser Ala Asp Ser Leu Asp Leu Ala Thr
                405                 410                 415

Thr Thr Ser Pro Gln Asn Tyr Ser Glu Thr Ala Gly Asn Asn Asn Thr
            420                 425                 430

His His Gln Asp Thr Gly Glu Glu Ser Ala Ser Ser Gly Lys Leu Gly
        435                 440                 445

Leu Ile Thr Asn Thr Ile Ala Gly Val Ala Gly Leu Ile Thr Gly Gly
    450                 455                 460

Arg Arg Thr Arg Arg Glu Val Ile Val Asn Ala Gln Pro Lys Cys Asn
465                 470                 475                 480

Pro Asn Leu His Tyr Trp Thr Thr Gln Asp Glu Gly Ala Ala Ile Gly
                485                 490                 495

Leu Ala Trp Ile Pro Tyr Phe Gly Pro Ala Ala Glu Gly Ile Tyr Thr
            500                 505                 510

Glu Gly Leu Met His Asn Gln Asp Gly Leu Ile Cys Gly Leu Arg Gln
        515                 520                 525

Leu Ala Asn Glu Thr Thr Gln Ala Leu Gln Leu Phe Leu Arg Ala Thr
    530                 535                 540

Thr Glu Leu Arg Thr Phe Ser Ile Leu Asn Arg Lys Ala Ile Asp Phe
545                 550                 555                 560

Leu Leu Gln Arg Trp Gly Gly Thr Cys His Ile Leu Gly Pro Asp Cys
                565                 570                 575

Cys Ile Glu Pro His Asp Trp Thr Lys Asn Ile Thr Asp Lys Ile Asp
            580                 585                 590

Gln Ile Ile His Asp Phe Val Asp Lys Thr Leu Pro Asp Gln Gly Asp
        595                 600                 605

Asn Asp Asn Trp Trp Thr Gly
    610                 615
```

<210> SEQ ID NO 11
<211> LENGTH: 615
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 11

```
Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Val Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80
```

```
Ile Lys Lys Pro Asp Gly Ser Glu Cys Leu Pro Ala Ala Pro Asp Gly
                 85                  90                  95
Ile Arg Gly Phe Pro Arg Cys Arg Tyr Val His Lys Val Ser Gly Thr
            100                 105                 110
Gly Pro Cys Ala Gly Asp Phe Ala Phe His Lys Glu Gly Ala Phe Phe
        115                 120                 125
Leu Tyr Asp Arg Leu Ala Ser Thr Val Ile Tyr Arg Gly Thr Thr Phe
130                 135                 140
Ala Glu Gly Val Val Ala Phe Leu Ile Leu Pro Gln Ala Lys Lys Asp
145                 150                 155                 160
Phe Phe Ser Ser His Pro Leu Arg Glu Pro Val Asn Ala Thr Glu Asp
                165                 170                 175
Pro Ser Ser Gly Tyr Tyr Ser Thr Thr Ile Arg Tyr Gln Ala Thr Gly
            180                 185                 190
Phe Gly Thr Asn Glu Thr Glu Tyr Leu Phe Glu Val Asp Asn Leu Thr
        195                 200                 205
Tyr Val Gln Leu Glu Ser Arg Phe Thr Pro Gln Phe Leu Leu Gln Leu
210                 215                 220
Asn Glu Thr Ile Tyr Ala Ser Gly Lys Arg Ser Asn Thr Thr Gly Lys
225                 230                 235                 240
Leu Ile Trp Lys Val Asn Pro Glu Ile Asp Thr Thr Ile Gly Glu Trp
                245                 250                 255
Ala Phe Trp Glu Thr Lys Lys Asn Leu Thr Arg Lys Ile Arg Ser Glu
            260                 265                 270
Glu Leu Ser Phe Thr Ala Val Ser Asn Gly Pro Lys Asn Ile Ser Gly
        275                 280                 285
Gln Ser Pro Ala Arg Thr Ser Ser Asp Pro Glu Thr Asn Thr Thr Asn
290                 295                 300
Glu Asp His Lys Ile Met Ala Ser Glu Asn Ser Ser Ala Met Val Gln
305                 310                 315                 320
Val His Ser Gln Gly Arg Lys Ala Ala Val Ser His Leu Thr Thr Leu
                325                 330                 335
Ala Thr Ile Ser Thr Ser Pro Gln Pro Pro Thr Thr Lys Thr Gly Pro
            340                 345                 350
Asp Asn Ser Thr His Asn Thr Pro Val Tyr Lys Leu Asp Ile Ser Glu
        355                 360                 365
Ala Thr Gln Val Gly Gln His His Arg Arg Ala Asp Asn Asp Ser Thr
370                 375                 380
Ala Ser Asp Thr Pro Pro Ala Thr Thr Ala Ala Gly Pro Leu Lys Ala
385                 390                 395                 400
Glu Asn Thr Asn Thr Ser Lys Ser Ala Asp Ser Leu Asp Leu Ala Thr
                405                 410                 415
Thr Thr Ser Pro Gln Asn Tyr Ser Glu Thr Ala Gly Asn Asn Asn Thr
            420                 425                 430
His His Gln Asp Thr Gly Glu Glu Ser Ala Ser Ser Gly Lys Leu Gly
        435                 440                 445
Leu Ile Thr Asn Thr Ile Ala Gly Val Ala Gly Leu Ile Thr Gly Gly
450                 455                 460
Arg Arg Thr Arg Arg Glu Val Ile Val Asn Ala Gln Pro Lys Cys Asn
465                 470                 475                 480
Pro Asn Leu His Tyr Trp Thr Thr Gln Asp Glu Gly Ala Ala Ile Gly
                485                 490                 495
```

-continued

```
Leu Ala Trp Ile Pro Tyr Phe Gly Pro Ala Ala Glu Gly Ile Tyr Thr
            500                 505                 510

Glu Gly Leu Met His Asn Gln Asp Gly Leu Ile Cys Gly Leu Arg Gln
            515                 520                 525

Leu Ala Asn Glu Thr Thr Gln Ala Leu Gln Leu Phe Leu Arg Ala Thr
530                 535                 540

Pro Glu Leu Arg Thr Phe Ser Ile Leu Asn Arg Lys Ala Ile Asp Phe
545                 550                 555                 560

Leu Leu Gln Arg Trp Gly Gly Thr Cys His Ile Leu Gly Pro Asp Cys
                565                 570                 575

Cys Ile Glu Pro His Asp Trp Thr Lys Asn Ile Thr Asp Lys Ile Asp
            580                 585                 590

Gln Ile Ile His Asp Phe Val Asp Lys Thr Leu Pro Asp Gln Gly Asp
            595                 600                 605

Asn Asp Asn Trp Trp Thr Gly
            610                 615

<210> SEQ ID NO 12
<211> LENGTH: 615
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Val Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
    210                 215                 220
```

Asn Glu Thr Ile Tyr Ala Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
            245                 250                 255

Ala Phe Trp Glu Thr Lys Lys Asn Leu Thr Arg Lys Ile Arg Ser Glu
        260                 265                 270

Glu Leu Ser Phe Thr Ala Val Ser Asn Gly Pro Lys Asn Ile Ser Gly
    275                 280                 285

Gln Ser Pro Ala Arg Thr Ser Ser Asp Pro Glu Thr Asn Thr Thr Asn
290                 295                 300

Glu Asp His Lys Ile Met Ala Ser Glu Asn Ser Ser Ala Met Val Gln
305                 310                 315                 320

Val His Ser Gln Gly Arg Lys Ala Ala Val Ser His Leu Thr Thr Leu
            325                 330                 335

Ala Thr Ile Ser Thr Ser Pro Gln Pro Pro Thr Thr Lys Thr Gly Pro
        340                 345                 350

Asp Asn Ser Thr His Asn Thr Pro Val Tyr Lys Leu Asp Ile Ser Glu
    355                 360                 365

Ala Thr Gln Val Gly Gln His His Arg Arg Ala Asp Asn Asp Ser Thr
370                 375                 380

Ala Ser Asp Thr Pro Pro Ala Thr Thr Ala Ala Gly Pro Leu Lys Ala
385                 390                 395                 400

Glu Asn Thr Asn Thr Ser Lys Ser Ala Asp Ser Leu Asp Leu Ala Thr
            405                 410                 415

Thr Thr Ser Pro Gln Asn Tyr Ser Glu Thr Ala Gly Asn Asn Asn Thr
        420                 425                 430

His His Gln Asp Thr Gly Glu Glu Ser Ala Ser Ser Gly Lys Leu Gly
    435                 440                 445

Leu Ile Thr Asn Thr Ile Ala Gly Val Ala Gly Leu Ile Thr Gly Gly
450                 455                 460

Arg Arg Thr Arg Arg Glu Val Ile Val Asn Ala Gln Pro Lys Cys Asn
465                 470                 475                 480

Pro Asn Leu His Tyr Trp Thr Thr Gln Asp Glu Gly Ala Ala Ile Gly
            485                 490                 495

Leu Ala Trp Ile Pro Tyr Phe Gly Pro Ala Ala Glu Gly Ile Tyr Thr
        500                 505                 510

Glu Gly Leu Met His Asn Gln Asp Gly Leu Ile Cys Gly Leu Arg Gln
    515                 520                 525

Leu Ala Asn Glu Thr Thr Gln Ala Leu Gln Leu Phe Leu Arg Ala Thr
530                 535                 540

Thr Glu Leu Arg Thr Phe Ser Ile Leu Asn Arg Phe Ala Ile Asp Phe
545                 550                 555                 560

Leu Leu Gln Arg Trp Gly Gly Thr Cys His Ile Leu Gly Pro Asp Cys
            565                 570                 575

Cys Ile Glu Pro His Asp Trp Thr Lys Asn Ile Thr Asp Lys Ile Asp
        580                 585                 590

Gln Ile Ile His Asp Phe Val Asp Lys Thr Leu Pro Asp Gln Gly Asp
    595                 600                 605

Asn Asp Asn Trp Trp Thr Gly
610                 615

<210> SEQ ID NO 13
<211> LENGTH: 615
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 13

```
Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
                20                  25                  30

Ser Val Gly Leu Asn Leu Glu Gly Asn Gly Val Ala Thr Asp Val Pro
            35                  40                  45

Ser Val Thr Lys Arg Trp Gly Phe Arg Ser Gly Val Pro Pro Lys Val
        50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
210                 215                 220

Asn Glu Thr Ile Tyr Ala Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270

Glu Leu Ser Phe Thr Ala Val Ser Asn Gly Pro Lys Asn Ile Ser Gly
        275                 280                 285

Gln Ser Pro Ala Arg Thr Ser Asp Pro Glu Thr Asn Thr Thr Asn
290                 295                 300

Glu Asp His Lys Ile Met Ala Ser Glu Asn Ser Ser Ala Met Val Gln
305                 310                 315                 320

Val His Ser Gln Gly Arg Lys Ala Ala Val Ser His Leu Thr Thr Leu
                325                 330                 335

Ala Thr Ile Ser Thr Ser Pro Gln Pro Pro Thr Thr Lys Thr Gly Pro
            340                 345                 350

Asp Asn Ser Thr His Asn Thr Pro Val Tyr Lys Leu Asp Ile Ser Glu
        355                 360                 365

Ala Thr Gln Val Gly Gln His His Arg Arg Ala Asp Asn Asp Ser Thr
370                 375                 380
```

```
Ala Ser Asp Thr Pro Pro Ala Thr Thr Ala Ala Gly Pro Leu Lys Ala
385                 390                 395                 400

Glu Asn Thr Asn Thr Ser Lys Ser Ala Asp Ser Leu Asp Leu Ala Thr
                405                 410                 415

Thr Thr Ser Pro Gln Asn Tyr Ser Glu Thr Ala Gly Asn Asn Asn Thr
            420                 425                 430

His His Gln Asp Thr Gly Glu Glu Ser Ala Ser Ser Gly Lys Leu Gly
        435                 440                 445

Leu Ile Thr Asn Thr Ile Ala Gly Val Ala Gly Leu Ile Thr Gly Gly
    450                 455                 460

Arg Arg Thr Arg Arg Glu Val Ile Val Asn Ala Gln Pro Lys Cys Asn
465                 470                 475                 480

Pro Asn Leu His Tyr Trp Thr Thr Gln Asp Glu Gly Ala Ala Ile Gly
                485                 490                 495

Leu Ala Trp Ile Pro Tyr Phe Gly Pro Ala Ala Glu Gly Ile Tyr Thr
            500                 505                 510

Glu Gly Leu Met His Asn Gln Asp Gly Leu Ile Cys Gly Leu Arg Gln
        515                 520                 525

Leu Ala Asn Glu Thr Thr Gln Ala Leu Gln Leu Phe Leu Arg Ala Thr
    530                 535                 540

Pro Glu Leu Arg Thr Phe Ser Ile Leu Asn Arg Phe Ala Ile Asp Phe
545                 550                 555                 560

Leu Leu Gln Arg Trp Gly Gly Thr Cys His Ile Leu Gly Pro Asp Cys
                565                 570                 575

Cys Ile Glu Pro His Asp Trp Thr Lys Asn Ile Thr Asp Lys Ile Asp
            580                 585                 590

Gln Ile Ile His Asp Phe Val Asp Lys Thr Leu Pro Asp Gln Gly Asp
        595                 600                 605

Asn Asp Asn Trp Trp Thr Gly
    610                 615

<210> SEQ ID NO 14
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Val Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110
```

Gly Pro Cys Ala Gly Asp Phe Ala Phe His Lys Glu Gly Ala Phe Phe
            115                 120                 125

Leu Tyr Asp Arg Leu Ala Ser Thr Val Ile Tyr Arg Gly Thr Thr Phe
130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
            165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
            195                 200                 205

Tyr Val Gln Leu Glu Ser Arg Phe Thr Pro Gln Phe Leu Leu Gln Leu
210                 215                 220

Asn Glu Thr Ile Tyr Ala Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
            245                 250                 255

Ala Phe Trp Glu Thr Lys Lys Asn Leu Thr Arg Lys Ile Arg Ser Glu
            260                 265                 270

Glu Leu Ser Phe Thr Ala Val Ser Asn Ser Ala Ser Ser Gly Lys Leu
            275                 280                 285

Gly Leu Ile Thr Asn Thr Ile Ala Gly Val Ala Gly Leu Ile Thr Gly
290                 295                 300

Gly Arg Arg Thr Arg Arg Glu Val Ile Val Asn Ala Gln Pro Lys Cys
305                 310                 315                 320

Asn Pro Asn Leu His Tyr Trp Thr Thr Gln Asp Glu Gly Ala Ala Ile
            325                 330                 335

Gly Leu Ala Trp Ile Pro Tyr Phe Gly Pro Ala Ala Glu Gly Ile Tyr
            340                 345                 350

Thr Glu Gly Leu Met His Asn Gln Asp Gly Leu Ile Cys Gly Leu Arg
            355                 360                 365

Gln Leu Ala Asn Glu Thr Thr Gln Ala Leu Gln Leu Phe Leu Arg Ala
370                 375                 380

Thr Thr Glu Leu Arg Thr Phe Ser Ile Leu Asn Arg Lys Ala Ile Asp
385                 390                 395                 400

Phe Leu Leu Gln Arg Trp Gly Gly Thr Cys His Ile Leu Gly Pro Asp
            405                 410                 415

Cys Cys Ile Glu Pro His Asp Trp Thr Lys Asn Ile Thr Asp Lys Ile
            420                 425                 430

Asp Gln Ile Ile His Asp Phe Val Asp Lys Thr Leu Pro Asp Gln Gly
            435                 440                 445

Asp Asn Asp Asn Trp Trp Thr Gly
450                 455

<210> SEQ ID NO 15
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

```
Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Val Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
210                 215                 220

Asn Glu Thr Ile Tyr Ala Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270

Glu Leu Ser Phe Thr Ala Val Ser Asn Ser Ala Ser Ser Gly Lys Leu
        275                 280                 285

Gly Leu Ile Thr Asn Thr Ile Ala Gly Val Ala Gly Leu Ile Thr Gly
290                 295                 300

Gly Arg Arg Thr Arg Arg Glu Val Ile Val Asn Ala Gln Pro Lys Cys
305                 310                 315                 320

Asn Pro Asn Leu His Tyr Trp Thr Thr Gln Asp Glu Gly Ala Ala Ile
                325                 330                 335

Gly Leu Ala Trp Ile Pro Tyr Phe Gly Pro Ala Ala Glu Gly Ile Tyr
            340                 345                 350

Thr Glu Gly Leu Met His Asn Gln Asp Gly Leu Ile Cys Gly Leu Arg
        355                 360                 365

Gln Leu Ala Asn Glu Thr Thr Gln Ala Leu Gln Leu Phe Leu Arg Ala
370                 375                 380

Thr Pro Glu Leu Arg Thr Phe Ser Ile Leu Asn Arg Lys Ala Ile Asp
385                 390                 395                 400
```

-continued

```
Phe Leu Leu Gln Arg Trp Gly Gly Thr Cys His Ile Leu Gly Pro Asp
            405                 410                 415

Cys Cys Ile Glu Pro His Asp Trp Thr Lys Asn Ile Thr Asp Lys Ile
            420                 425                 430

Asp Gln Ile Ile His Asp Phe Val Asp Lys Thr Leu Pro Asp Gln Gly
            435                 440                 445

Asp Asn Asp Asn Trp Trp Thr Gly
450                 455
```

<210> SEQ ID NO 16
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

```
Ile Pro Leu Gly Val Ile His Asn Ser Ala Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
            35                  40                  45

Ser Val Thr Lys Arg Trp Gly Phe Arg Ser Gly Val Pro Pro Lys Val
            50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
            115                 120                 125

Leu Tyr Asp Arg Leu Ala Ser Thr Val Ile Tyr Arg Gly Thr Thr Phe
            130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
            195                 200                 205

Tyr Val Gln Leu Glu Ser Arg Phe Thr Pro Gln Phe Leu Leu Gln Leu
            210                 215                 220

Asn Glu Thr Ile Tyr Ala Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270

Glu Leu Ser Phe Thr Ala Val Ser Asn Ser Ala Ser Ser Gly Lys Leu
            275                 280                 285
```

```
Gly Leu Ile Thr Asn Thr Ile Ala Gly Val Ala Gly Leu Ile Thr Gly
        290                 295                 300

Gly Arg Arg Thr Arg Arg Glu Val Ile Val Asn Ala Gln Pro Lys Cys
305                 310                 315                 320

Asn Pro Asn Leu His Tyr Trp Thr Thr Gln Asp Glu Gly Ala Ala Ile
                325                 330                 335

Gly Leu Ala Trp Ile Pro Tyr Phe Gly Pro Ala Ala Glu Gly Ile Tyr
            340                 345                 350

Thr Glu Gly Leu Met His Asn Gln Asp Gly Leu Ile Cys Gly Leu Arg
        355                 360                 365

Gln Leu Ala Asn Glu Thr Thr Gln Ala Leu Gln Leu Phe Leu Arg Ala
    370                 375                 380

Thr Pro Glu Leu Arg Thr Phe Ser Ile Leu Asn Arg Lys Ala Ile Asp
385                 390                 395                 400

Phe Leu Leu Gln Arg Trp Gly Gly Thr Cys His Ile Leu Gly Pro Asp
                405                 410                 415

Cys Cys Ile Glu Pro His Asp Trp Thr Lys Asn Ile Thr Asp Lys Ile
            420                 425                 430

Asp Gln Ile Ile His Asp Phe Val Asp Lys Thr Leu Pro Asp Gln Gly
        435                 440                 445

Asp Asn Asp Asn Trp Trp Thr Gly
    450                 455

<210> SEQ ID NO 17
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Val Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175
```

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
    210                 215                 220

Asn Glu Thr Ile Tyr Ala Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270

Glu Leu Ser Phe Thr Ala Val Ser Asn Ser Ala Ser Ser Gly Lys Leu
        275                 280                 285

Gly Leu Ile Thr Asn Thr Ile Ala Gly Val Ala Gly Leu Ile Thr Gly
    290                 295                 300

Gly Arg Arg Thr Arg Arg Glu Val Ile Val Asn Ala Gln Pro Lys Cys
305                 310                 315                 320

Asn Pro Asn Leu His Tyr Trp Thr Thr Gln Asp Glu Gly Ala Ala Ile
                325                 330                 335

Gly Leu Ala Trp Ile Pro Tyr Phe Gly Pro Ala Ala Glu Gly Ile Tyr
            340                 345                 350

Thr Glu Gly Leu Met His Asn Gln Asp Gly Leu Ile Cys Gly Leu Arg
        355                 360                 365

Gln Leu Ala Asn Glu Thr Thr Gln Ala Leu Gln Leu Phe Leu Arg Ala
    370                 375                 380

Thr Thr Glu Leu Arg Thr Phe Ser Ile Leu Asn Arg Phe Ala Ile Asp
385                 390                 395                 400

Phe Leu Leu Gln Arg Trp Gly Gly Thr Cys His Ile Leu Gly Pro Asp
                405                 410                 415

Cys Cys Ile Glu Pro His Asp Trp Thr Lys Asn Ile Thr Asp Lys Ile
            420                 425                 430

Asp Gln Ile Ile His Asp Phe Val Asp Lys Thr Leu Pro Asp Gln Gly
        435                 440                 445

Asp Asn Asp Asn Trp Trp Thr Gly
    450                 455

<210> SEQ ID NO 18
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Val Thr Lys Arg Trp Gly Phe Arg Ser Gly Val Pro Pro Lys Val
    50                  55                  60

```
Val Asn Tyr Glu Ala Gly Glu Trp Ala Glu Asn Cys Tyr Asn Leu Glu
 65                  70                  75                  80

Ile Lys Lys Pro Asp Gly Ser Glu Cys Leu Pro Ala Pro Asp Gly
             85                  90                  95

Ile Arg Gly Phe Pro Arg Cys Arg Tyr Val His Lys Val Ser Gly Thr
                100                 105                 110

Gly Pro Cys Ala Gly Asp Phe Ala Phe His Lys Glu Gly Ala Phe Phe
            115                 120                 125

Leu Tyr Asp Arg Leu Ala Ser Thr Val Ile Tyr Arg Gly Thr Thr Phe
130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
            195                 200                 205

Tyr Val Gln Leu Glu Ser Arg Phe Thr Pro Gln Phe Leu Leu Gln Leu
210                 215                 220

Asn Glu Thr Ile Tyr Ala Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270

Glu Leu Ser Phe Thr Ala Val Ser Asn Ser Ala Ser Ser Gly Lys Leu
            275                 280                 285

Gly Leu Ile Thr Asn Thr Ile Ala Gly Val Ala Gly Leu Ile Thr Gly
            290                 295                 300

Gly Arg Arg Thr Arg Arg Glu Val Ile Val Asn Ala Gln Pro Lys Cys
305                 310                 315                 320

Asn Pro Asn Leu His Tyr Trp Thr Thr Gln Asp Glu Gly Ala Ala Ile
                325                 330                 335

Gly Leu Ala Trp Ile Pro Tyr Phe Gly Pro Ala Ala Glu Gly Ile Tyr
            340                 345                 350

Thr Glu Gly Leu Met His Asn Gln Asp Gly Leu Ile Cys Gly Leu Arg
            355                 360                 365

Gln Leu Ala Asn Glu Thr Thr Gln Ala Leu Gln Leu Phe Leu Arg Ala
370                 375                 380

Thr Pro Glu Leu Arg Thr Phe Ser Ile Leu Asn Arg Phe Ala Ile Asp
385                 390                 395                 400

Phe Leu Leu Gln Arg Trp Gly Gly Thr Cys His Ile Leu Gly Pro Asp
                405                 410                 415

Cys Cys Ile Glu Pro His Asp Trp Thr Lys Asn Ile Thr Asp Lys Ile
            420                 425                 430

Asp Gln Ile Ile His Asp Phe Val Asp Lys Thr Leu Pro Asp Gln Gly
            435                 440                 445

Asp Asn Asp Asn Trp Trp Thr Gly
450                 455

<210> SEQ ID NO 19
<211> LENGTH: 615
<212> TYPE: PRT
```

<213> ORGANISM: Zaire ebolavirus

<400> SEQUENCE: 19

| | | | | | | | | | | | | | | |
|---|---|---|---|---|---|---|---|---|---|---|---|---|---|---|
| Ile | Pro | Leu | Gly | Val | Ile | His | Asn | Ser | Thr | Leu | Gln | Val | Ser | Asp | Val |
| 1 | | | | 5 | | | | | 10 | | | | | 15 | |
| Asp | Lys | Leu | Val | Cys | Arg | Asp | Lys | Leu | Ser | Ser | Thr | Asn | Gln | Leu | Arg |
| | | | 20 | | | | | 25 | | | | | 30 | | |
| Ser | Val | Gly | Leu | Asn | Leu | Glu | Gly | Asn | Gly | Val | Ala | Thr | Asp | Val | Pro |
| | | 35 | | | | | 40 | | | | | 45 | | | |
| Ser | Ala | Thr | Lys | Arg | Trp | Gly | Phe | Arg | Ser | Gly | Val | Pro | Pro | Lys | Val |
| | 50 | | | | | 55 | | | | | 60 | | | | |
| Val | Asn | Tyr | Glu | Ala | Gly | Glu | Trp | Ala | Glu | Asn | Cys | Tyr | Asn | Leu | Glu |
| 65 | | | | | 70 | | | | | 75 | | | | | 80 |
| Ile | Lys | Lys | Pro | Asp | Gly | Ser | Glu | Cys | Leu | Pro | Ala | Ala | Pro | Asp | Gly |
| | | | | 85 | | | | | 90 | | | | | 95 | |
| Ile | Arg | Gly | Phe | Pro | Arg | Cys | Arg | Tyr | Val | His | Lys | Val | Ser | Gly | Thr |
| | | | 100 | | | | | 105 | | | | | 110 | | |
| Gly | Pro | Cys | Ala | Gly | Asp | Phe | Ala | Phe | His | Lys | Glu | Gly | Ala | Phe | Phe |
| | | 115 | | | | | 120 | | | | | 125 | | | |
| Leu | Tyr | Asp | Arg | Leu | Ala | Ser | Thr | Val | Ile | Tyr | Arg | Gly | Thr | Thr | Phe |
| | 130 | | | | | 135 | | | | | 140 | | | | |
| Ala | Glu | Gly | Val | Val | Ala | Phe | Leu | Ile | Leu | Pro | Gln | Ala | Lys | Lys | Asp |
| 145 | | | | | 150 | | | | | 155 | | | | | 160 |
| Phe | Phe | Ser | Ser | His | Pro | Leu | Arg | Glu | Pro | Val | Asn | Ala | Thr | Glu | Asp |
| | | | | 165 | | | | | 170 | | | | | 175 | |
| Pro | Ser | Ser | Gly | Tyr | Tyr | Ser | Thr | Thr | Ile | Arg | Tyr | Gln | Ala | Thr | Gly |
| | | | 180 | | | | | 185 | | | | | 190 | | |
| Phe | Gly | Thr | Asn | Glu | Thr | Glu | Tyr | Leu | Phe | Glu | Val | Asp | Asn | Leu | Thr |
| | | 195 | | | | | 200 | | | | | 205 | | | |
| Tyr | Val | Gln | Leu | Glu | Ser | Arg | Phe | Thr | Pro | Gln | Phe | Leu | Leu | Gln | Leu |
| | 210 | | | | | 215 | | | | | 220 | | | | |
| Asn | Glu | Thr | Ile | Tyr | Thr | Ser | Gly | Lys | Arg | Ser | Asn | Thr | Thr | Gly | Lys |
| 225 | | | | | 230 | | | | | 235 | | | | | 240 |
| Leu | Ile | Trp | Lys | Val | Asn | Pro | Glu | Ile | Asp | Thr | Thr | Ile | Gly | Glu | Trp |
| | | | | 245 | | | | | 250 | | | | | 255 | |
| Ala | Phe | Trp | Glu | Thr | Lys | Lys | Asn | Leu | Thr | Arg | Lys | Ile | Arg | Ser | Glu |
| | | | 260 | | | | | 265 | | | | | 270 | | |
| Glu | Leu | Ser | Phe | Thr | Ala | Val | Ser | Asn | Arg | Ala | Lys | Asn | Ile | Ser | Gly |
| | | 275 | | | | | 280 | | | | | 285 | | | |
| Gln | Ser | Pro | Ala | Arg | Thr | Ser | Ser | Asp | Pro | Gly | Thr | Asn | Thr | Thr | Thr |
| | 290 | | | | | 295 | | | | | 300 | | | | |
| Glu | Asp | His | Lys | Ile | Met | Ala | Ser | Glu | Asn | Ser | Ser | Ala | Met | Val | Gln |
| 305 | | | | | 310 | | | | | 315 | | | | | 320 |
| Val | His | Ser | Gln | Gly | Arg | Glu | Ala | Ala | Val | Ser | His | Leu | Thr | Thr | Leu |
| | | | | 325 | | | | | 330 | | | | | 335 | |
| Ala | Thr | Ile | Ser | Thr | Ser | Pro | Gln | Pro | Pro | Thr | Thr | Lys | Pro | Gly | Pro |
| | | | 340 | | | | | 345 | | | | | 350 | | |
| Asp | Asn | Ser | Thr | His | Asn | Thr | Pro | Val | Tyr | Lys | Leu | Asp | Ile | Ser | Glu |
| | | 355 | | | | | 360 | | | | | 365 | | | |
| Ala | Thr | Gln | Val | Glu | Gln | His | His | Arg | Arg | Thr | Asp | Asn | Asp | Ser | Thr |
| | 370 | | | | | 375 | | | | | 380 | | | | |
| Ala | Ser | Asp | Thr | Pro | Pro | Ala | Thr | Thr | Ala | Ala | Gly | Pro | Leu | Lys | Ala |
| 385 | | | | | 390 | | | | | 395 | | | | | 400 |

Glu Asn Thr Asn Thr Ser Lys Gly Thr Asp Leu Leu Asp Pro Ala Thr
            405                 410                 415

Thr Thr Ser Pro Gln Asn His Ser Glu Thr Ala Gly Asn Asn Asn Thr
        420                 425                 430

His His Gln Asp Thr Gly Glu Glu Ser Ala Ser Ser Gly Lys Leu Gly
        435                 440                 445

Leu Ile Thr Asn Thr Ile Ala Gly Val Ala Gly Leu Ile Thr Gly Gly
    450                 455                 460

Arg Arg Ala Arg Arg Glu Ala Ile Val Asn Ala Gln Pro Lys Cys Asn
465                 470                 475                 480

Pro Asn Leu His Tyr Trp Thr Thr Gln Asp Glu Gly Ala Ala Ile Gly
            485                 490                 495

Leu Ala Trp Ile Pro Tyr Phe Gly Pro Ala Ala Glu Gly Ile Tyr Ile
                500                 505                 510

Glu Gly Leu Met His Asn Gln Asp Gly Leu Ile Cys Gly Leu Arg Gln
            515                 520                 525

Leu Ala Asn Glu Thr Thr Gln Ala Leu Gln Leu Phe Leu Arg Ala Thr
        530                 535                 540

Thr Glu Leu Arg Thr Phe Ser Ile Leu Asn Arg Lys Ala Ile Asp Phe
545                 550                 555                 560

Leu Leu Gln Arg Trp Gly Gly Thr Cys His Ile Leu Gly Pro Asp Cys
                565                 570                 575

Cys Ile Glu Pro His Asp Trp Thr Lys Asn Ile Thr Asp Lys Ile Asp
            580                 585                 590

Gln Ile Ile His Asp Phe Val Asp Lys Thr Leu Pro Asp Gln Gly Asp
        595                 600                 605

Asn Asp Asn Trp Trp Thr Gly
    610                 615

<210> SEQ ID NO 20
<211> LENGTH: 615
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
            85                  90                  95

Ile Arg Gly Phe Pro Arg Cys Arg Tyr Val His Lys Val Ser Gly Thr
        100                 105                 110

Gly Pro Cys Ala Gly Asp Phe Ala Phe His Lys Glu Gly Ala Phe Phe
    115                 120                 125

```
Leu Tyr Asp Arg Leu Ala Ser Thr Val Ile Tyr Arg Gly Thr Thr Phe
        130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
                180                 185                 190

Phe Gly Thr Asn Glu Thr Glu Tyr Leu Phe Glu Val Asp Asn Leu Thr
                195                 200                 205

Tyr Val Gln Leu Glu Ser Arg Phe Thr Pro Gln Phe Leu Leu Gln Leu
210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
                260                 265                 270

Glu Leu Ser Phe Thr Ala Val Ser Asn Arg Ala Lys Asn Ile Ser Gly
            275                 280                 285

Gln Ser Pro Ala Arg Thr Ser Ser Asp Pro Gly Thr Asn Thr Thr Thr
290                 295                 300

Glu Asp His Lys Ile Met Ala Ser Glu Asn Ser Ser Ala Met Val Gln
305                 310                 315                 320

Val His Ser Gln Gly Arg Glu Ala Ala Val Ser His Leu Thr Thr Leu
                325                 330                 335

Ala Thr Ile Ser Thr Ser Pro Gln Pro Pro Thr Thr Lys Pro Gly Pro
            340                 345                 350

Asp Asn Ser Thr His Asn Thr Pro Val Tyr Lys Leu Asp Ile Ser Glu
            355                 360                 365

Ala Thr Gln Val Glu Gln His His Arg Arg Thr Asp Asn Asp Ser Thr
370                 375                 380

Ala Ser Asp Thr Pro Pro Ala Thr Thr Ala Ala Gly Pro Leu Lys Ala
385                 390                 395                 400

Glu Asn Thr Asn Thr Ser Lys Gly Thr Asp Leu Leu Asp Pro Ala Thr
                405                 410                 415

Thr Thr Ser Pro Gln Asn His Ser Glu Thr Ala Gly Asn Asn Asn Thr
            420                 425                 430

His His Gln Asp Thr Gly Glu Glu Ser Ala Ser Ser Gly Lys Leu Gly
        435                 440                 445

Leu Ile Thr Asn Thr Ile Ala Gly Val Ala Gly Leu Ile Thr Gly Gly
        450                 455                 460

Arg Arg Ala Arg Arg Glu Ala Ile Val Asn Ala Gln Pro Lys Cys Asn
465                 470                 475                 480

Pro Asn Leu His Tyr Trp Thr Thr Gln Asp Glu Gly Ala Ala Ile Gly
                485                 490                 495

Leu Ala Trp Ile Pro Tyr Phe Gly Pro Ala Ala Glu Gly Ile Tyr Ile
            500                 505                 510

Glu Gly Leu Met His Asn Gln Asp Gly Leu Ile Cys Gly Leu Arg Gln
            515                 520                 525

Leu Ala Asn Glu Thr Thr Gln Ala Leu Gln Leu Phe Leu Arg Ala Thr
530                 535                 540
```

```
Pro Glu Leu Arg Thr Phe Ser Ile Leu Asn Arg Lys Ala Ile Asp Phe
545                 550                 555                 560

Leu Leu Gln Arg Trp Gly Gly Thr Cys His Ile Leu Gly Pro Asp Cys
                565                 570                 575

Cys Ile Glu Pro His Asp Trp Thr Lys Asn Ile Thr Asp Lys Ile Asp
            580                 585                 590

Gln Ile Ile His Asp Phe Val Asp Lys Thr Leu Pro Asp Gln Gly Asp
        595                 600                 605

Asn Asp Asn Trp Trp Thr Gly
    610                 615

<210> SEQ ID NO 21
<211> LENGTH: 615
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
    210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270
```

Glu Leu Ser Phe Thr Ala Val Ser Asn Arg Ala Lys Asn Ile Ser Gly
            275                 280                 285

Gln Ser Pro Ala Arg Thr Ser Ser Asp Pro Gly Thr Asn Thr Thr Thr
290                 295                 300

Glu Asp His Lys Ile Met Ala Ser Glu Asn Ser Ser Ala Met Val Gln
305                 310                 315                 320

Val His Ser Gln Gly Arg Glu Ala Ala Val Ser His Leu Thr Thr Leu
                325                 330                 335

Ala Thr Ile Ser Thr Ser Pro Gln Pro Pro Thr Thr Lys Pro Gly Pro
            340                 345                 350

Asp Asn Ser Thr His Asn Thr Pro Val Tyr Lys Leu Asp Ile Ser Glu
            355                 360                 365

Ala Thr Gln Val Glu Gln His His Arg Arg Thr Asp Asn Asp Ser Thr
370                 375                 380

Ala Ser Asp Thr Pro Pro Ala Thr Thr Ala Ala Gly Pro Leu Lys Ala
385                 390                 395                 400

Glu Asn Thr Asn Thr Ser Lys Gly Thr Asp Leu Leu Asp Pro Ala Thr
                405                 410                 415

Thr Thr Ser Pro Gln Asn His Ser Glu Thr Ala Gly Asn Asn Asn Thr
            420                 425                 430

His His Gln Asp Thr Gly Glu Glu Ser Ala Ser Ser Gly Lys Leu Gly
            435                 440                 445

Leu Ile Thr Asn Thr Ile Ala Gly Val Ala Gly Leu Ile Thr Gly Gly
450                 455                 460

Arg Arg Ala Arg Arg Glu Ala Ile Val Asn Ala Gln Pro Lys Cys Asn
465                 470                 475                 480

Pro Asn Leu His Tyr Trp Thr Thr Gln Asp Glu Gly Ala Ala Ile Gly
                485                 490                 495

Leu Ala Trp Ile Pro Tyr Phe Gly Pro Ala Ala Glu Gly Ile Tyr Ile
            500                 505                 510

Glu Gly Leu Met His Asn Gln Asp Gly Leu Ile Cys Gly Leu Arg Gln
            515                 520                 525

Leu Ala Asn Glu Thr Thr Gln Ala Leu Gln Leu Phe Leu Arg Ala Thr
530                 535                 540

Thr Glu Leu Arg Thr Phe Ser Ile Leu Asn Arg Phe Ala Ile Asp Phe
545                 550                 555                 560

Leu Leu Gln Arg Trp Gly Gly Thr Cys His Ile Leu Gly Pro Asp Cys
                565                 570                 575

Cys Ile Glu Pro His Asp Trp Thr Lys Asn Ile Thr Asp Lys Ile Asp
            580                 585                 590

Gln Ile Ile His Asp Phe Val Asp Lys Thr Leu Pro Asp Gln Gly Asp
            595                 600                 605

Asn Asp Asn Trp Trp Thr Gly
    610                 615

<210> SEQ ID NO 22
<211> LENGTH: 615
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

```
Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270

Glu Leu Ser Phe Thr Ala Val Ser Asn Arg Ala Lys Asn Ile Ser Gly
        275                 280                 285

Gln Ser Pro Ala Arg Thr Ser Ser Asp Pro Gly Thr Asn Thr Thr Thr
    290                 295                 300

Glu Asp His Lys Ile Met Ala Ser Glu Asn Ser Ser Ala Met Val Gln
305                 310                 315                 320

Val His Ser Gln Gly Arg Glu Ala Ala Val Ser His Leu Thr Thr Leu
                325                 330                 335

Ala Thr Ile Ser Thr Ser Pro Gln Pro Pro Thr Thr Lys Pro Gly Pro
            340                 345                 350

Asp Asn Ser Thr His Asn Thr Pro Val Tyr Lys Leu Asp Ile Ser Glu
        355                 360                 365

Ala Thr Gln Val Glu Gln His His Arg Arg Thr Asp Asn Asp Ser Thr
    370                 375                 380

Ala Ser Asp Thr Pro Pro Ala Thr Ala Ala Gly Pro Leu Lys Ala
385                 390                 395                 400
```

```
Glu Asn Thr Asn Thr Ser Lys Gly Thr Asp Leu Leu Asp Pro Ala Thr
                405                 410                 415

Thr Thr Ser Pro Gln Asn His Ser Glu Thr Ala Gly Asn Asn Asn Thr
            420                 425                 430

His His Gln Asp Thr Gly Glu Glu Ser Ala Ser Ser Gly Lys Leu Gly
        435                 440                 445

Leu Ile Thr Asn Thr Ile Ala Gly Val Ala Gly Leu Ile Thr Gly Gly
    450                 455                 460

Arg Arg Ala Arg Arg Glu Ala Ile Val Asn Ala Gln Pro Lys Cys Asn
465                 470                 475                 480

Pro Asn Leu His Tyr Trp Thr Thr Gln Asp Glu Gly Ala Ala Ile Gly
                485                 490                 495

Leu Ala Trp Ile Pro Tyr Phe Gly Pro Ala Ala Glu Gly Ile Tyr Ile
                500                 505                 510

Glu Gly Leu Met His Asn Gln Asp Gly Leu Ile Cys Gly Leu Arg Gln
            515                 520                 525

Leu Ala Asn Glu Thr Thr Gln Ala Leu Gln Leu Phe Leu Arg Ala Thr
    530                 535                 540

Pro Glu Leu Arg Thr Phe Ser Ile Leu Asn Arg Phe Ala Ile Asp Phe
545                 550                 555                 560

Leu Leu Gln Arg Trp Gly Gly Thr Cys His Ile Leu Gly Pro Asp Cys
                565                 570                 575

Cys Ile Glu Pro His Asp Trp Thr Lys Asn Ile Thr Asp Lys Ile Asp
                580                 585                 590

Gln Ile Ile His Asp Phe Val Asp Lys Thr Leu Pro Asp Gln Gly Asp
            595                 600                 605

Asn Asp Asn Trp Trp Thr Gly
610                 615

<210> SEQ ID NO 23
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125
```

Leu Tyr Asp Arg Leu Ala Ser Thr Val Ile Tyr Arg Gly Thr Thr Phe
130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
            195                 200                 205

Tyr Val Gln Leu Glu Ser Arg Phe Thr Pro Gln Phe Leu Leu Gln Leu
210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270

Glu Leu Ser Phe Thr Ala Val Ser Asn Ser Ala Ser Ser Gly Lys Leu
            275                 280                 285

Gly Leu Ile Thr Asn Thr Ile Ala Gly Val Ala Gly Leu Ile Thr Gly
290                 295                 300

Gly Arg Arg Ala Arg Arg Glu Ala Ile Val Asn Ala Gln Pro Lys Cys
305                 310                 315                 320

Asn Pro Asn Leu His Tyr Trp Thr Thr Gln Asp Glu Gly Ala Ala Ile
                325                 330                 335

Gly Leu Ala Trp Ile Pro Tyr Phe Gly Pro Ala Ala Glu Gly Ile Tyr
            340                 345                 350

Ile Glu Gly Leu Met His Asn Gln Asp Gly Leu Ile Cys Gly Leu Arg
            355                 360                 365

Gln Leu Ala Asn Glu Thr Thr Gln Ala Leu Gln Leu Phe Leu Arg Ala
370                 375                 380

Thr Thr Glu Leu Arg Thr Phe Ser Ile Leu Asn Arg Lys Ala Ile Asp
385                 390                 395                 400

Phe Leu Leu Gln Arg Trp Gly Gly Thr Cys His Ile Leu Gly Pro Asp
                405                 410                 415

Cys Cys Ile Glu Pro His Asp Trp Thr Lys Asn Ile Thr Asp Lys Ile
            420                 425                 430

Asp Gln Ile Ile His Asp Phe Val Asp Lys Thr Leu Pro Asp Gln Gly
            435                 440                 445

Asp Asn Asp Asn Trp Trp Thr Gly
450                 455

<210> SEQ ID NO 24
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Ile Pro Leu Gly Val Ile His Asn Ser Thr Leu Gln Val Ser Asp Val
1               5                   10                  15

```
Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
 50                  55                  60

Val Asn Tyr Glu Ala Gly Glu Trp Ala Glu Asn Cys Tyr Asn Leu Glu
 65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
            165                 170                 175

Pro Ser Ser Gly Tyr Tyr Ser Thr Thr Ile Arg Tyr Gln Ala Thr Gly
        180                 185                 190

Phe Gly Thr Asn Glu Thr Glu Tyr Leu Phe Glu Val Asp Asn Leu Thr
    195                 200                 205

Tyr Val Gln Leu Glu Ser Arg Phe Thr Pro Gln Phe Leu Leu Gln Leu
210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
            245                 250                 255

Ala Phe Trp Glu Thr Lys Lys Asn Leu Thr Arg Lys Ile Arg Ser Glu
        260                 265                 270

Glu Leu Ser Phe Thr Ala Val Ser Asn Ser Ala Ser Ser Gly Lys Leu
    275                 280                 285

Gly Leu Ile Thr Asn Thr Ile Ala Gly Val Ala Gly Leu Ile Thr Gly
        290                 295                 300

Gly Arg Arg Ala Arg Arg Glu Ala Ile Val Asn Ala Gln Pro Lys Cys
305                 310                 315                 320

Asn Pro Asn Leu His Tyr Trp Thr Thr Gln Asp Glu Gly Ala Ala Ile
            325                 330                 335

Gly Leu Ala Trp Ile Pro Tyr Phe Gly Pro Ala Ala Glu Gly Ile Tyr
        340                 345                 350

Ile Glu Gly Leu Met His Asn Gln Asp Gly Leu Ile Cys Gly Leu Arg
    355                 360                 365

Gln Leu Ala Asn Glu Thr Thr Gln Ala Leu Gln Leu Phe Leu Arg Ala
        370                 375                 380

Thr Pro Glu Leu Arg Thr Phe Ser Ile Leu Asn Arg Lys Ala Ile Asp
385                 390                 395                 400

Phe Leu Leu Gln Arg Trp Gly Gly Thr Cys His Ile Leu Gly Pro Asp
            405                 410                 415

Cys Cys Ile Glu Pro His Asp Trp Thr Lys Asn Ile Thr Asp Lys Ile
        420                 425                 430
```

Asp Gln Ile Ile His Asp Phe Val Asp Lys Thr Leu Pro Asp Gln Gly
            435                 440                 445

Asp Asn Asp Asn Trp Trp Thr Gly
    450                 455

<210> SEQ ID NO 25
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
    210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270

Glu Leu Ser Phe Thr Ala Val Ser Asn Ser Ala Ser Ser Gly Lys Leu
        275                 280                 285

Gly Leu Ile Thr Asn Thr Ile Ala Gly Val Ala Gly Leu Ile Thr Gly
    290                 295                 300

Gly Arg Arg Ala Arg Arg Glu Ala Ile Val Asn Ala Gln Pro Lys Cys
305                 310                 315                 320

```
Asn Pro Asn Leu His Tyr Trp Thr Thr Gln Asp Glu Gly Ala Ala Ile
            325                 330                 335

Gly Leu Ala Trp Ile Pro Tyr Phe Gly Pro Ala Ala Glu Gly Ile Tyr
            340                 345                 350

Ile Glu Gly Leu Met His Asn Gln Asp Gly Leu Ile Cys Gly Leu Arg
            355                 360                 365

Gln Leu Ala Asn Glu Thr Thr Gln Ala Leu Gln Leu Phe Leu Arg Ala
            370                 375                 380

Thr Thr Glu Leu Arg Thr Phe Ser Ile Leu Asn Arg Phe Ala Ile Asp
385                 390                 395                 400

Phe Leu Leu Gln Arg Trp Gly Gly Thr Cys His Ile Leu Gly Pro Asp
            405                 410                 415

Cys Cys Ile Glu Pro His Asp Trp Thr Lys Asn Ile Thr Asp Lys Ile
            420                 425                 430

Asp Gln Ile Ile His Asp Phe Val Asp Lys Thr Leu Pro Asp Gln Gly
            435                 440                 445

Asp Asn Asp Asn Trp Trp Thr Gly
        450                 455

<210> SEQ ID NO 26
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205
```

Tyr Val Gln Leu Glu Ser Arg Phe Thr Pro Gln Phe Leu Gln Leu
210 215 220

Asn Glu Thr Ile Tyr Thr Ser Gly Lys Arg Ser Asn Thr Thr Gly Lys
225 230 235 240

Leu Ile Trp Lys Val Asn Pro Glu Ile Asp Thr Thr Ile Gly Glu Trp
245 250 255

Ala Phe Trp Glu Thr Lys Lys Asn Leu Thr Arg Lys Ile Arg Ser Glu
260 265 270

Glu Leu Ser Phe Thr Ala Val Ser Asn Ser Ala Ser Ser Gly Lys Leu
275 280 285

Gly Leu Ile Thr Asn Thr Ile Ala Gly Val Ala Gly Leu Ile Thr Gly
290 295 300

Gly Arg Arg Ala Arg Arg Glu Ala Ile Val Asn Ala Gln Pro Lys Cys
305 310 315 320

Asn Pro Asn Leu His Tyr Trp Thr Thr Gln Asp Glu Gly Ala Ala Ile
325 330 335

Gly Leu Ala Trp Ile Pro Tyr Phe Gly Pro Ala Ala Glu Gly Ile Tyr
340 345 350

Ile Glu Gly Leu Met His Asn Gln Asp Gly Leu Ile Cys Gly Leu Arg
355 360 365

Gln Leu Ala Asn Glu Thr Thr Gln Ala Leu Gln Leu Phe Leu Arg Ala
370 375 380

Thr Pro Glu Leu Arg Thr Phe Ser Ile Leu Asn Arg Phe Ala Ile Asp
385 390 395 400

Phe Leu Leu Gln Arg Trp Gly Gly Thr Cys His Ile Leu Gly Pro Asp
405 410 415

Cys Cys Ile Glu Pro His Asp Trp Thr Lys Asn Ile Thr Asp Lys Ile
420 425 430

Asp Gln Ile Ile His Asp Phe Val Asp Lys Thr Leu Pro Asp Gln Gly
435 440 445

Asp Asn Asp Asn Trp Trp Thr Gly
450 455

<210> SEQ ID NO 27
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 27

Leu Pro Val Leu Glu Ile Ala Ser Asn Ser Gln Pro Gln Asp Val Asp
1 5 10 15

Ser Val Cys Ser Gly Thr Leu Gln Lys Thr Glu Asp Val His Leu Met
20 25 30

Gly Phe Thr Leu Ser Gly Gln Lys Val Ala Asp Ser Pro Leu Glu Ala
35 40 45

Ser Lys Arg Trp Ala Phe Arg Thr Gly Val Pro Pro Lys Asn Val Glu
50 55 60

Tyr Thr Glu Gly Glu Glu Ala Lys Thr Cys Tyr Asn Ile Ser Val Thr
65 70 75 80

Asp Pro Ser Gly Lys Ser Leu Leu Leu Asp Pro Ser Asn Ile Arg
85 90 95

Asp Tyr Pro Lys Cys Lys Thr Val His His Ile Gln Gly Gln Asn Pro
            100                 105                 110

His Ala Gln Gly Ile Ala Leu His Leu Trp Gly Ala Phe Phe Leu Tyr
        115                 120                 125

Asp Arg Val Ala Ser Thr Thr Met Tyr Arg Gly Lys Val Phe Thr Glu
130                 135                 140

Gly Asn Ile Ala Ala Met Ile Val Asn Lys Thr Val His Arg Met Ile
145                 150                 155                 160

Phe Ser Arg Gln Gly Gln Gly Tyr Arg His Met Asn Leu Thr Ser Thr
                165                 170                 175

Asn Lys Tyr Trp Thr Ser Ser Asn Glu Thr Gln Arg Asn Asp Thr Gly
            180                 185                 190

Cys Phe Gly Ile Leu Gln Glu Tyr Asn Ser Thr Asn Gln Thr Cys
        195                 200                 205

Pro Pro Ser Leu Lys Pro Pro Ser Leu Pro Thr Val Thr Pro Ser Ile
        210                 215                 220

His Ser Thr Asn Thr Gln Ile Asn Thr Ala Lys Ser Gly Thr Arg Pro
225                 230                 235                 240

Pro Ile Tyr Phe Arg Lys Arg Ser Ile Leu Ala Lys Glu Gly Asp
                245                 250                 255

Ile Gly Pro Asn Leu Asp Gly Leu Ile Asn Thr Glu Ile Asp Phe Asp
            260                 265                 270

Pro Ile Pro Asn Thr Glu Thr Ile Phe Asp Glu Ser Pro Ser Phe Asn
        275                 280                 285

Thr Ser Thr Asn Glu Glu Gln His Thr Pro Pro Asn Ile Ser Leu Thr
290                 295                 300

Phe Ser Tyr Phe Pro Asp Lys Asn Gly Asp Thr Ala Tyr Ser Gly Glu
305                 310                 315                 320

Asn Glu Asn Asp Cys Asp Ala Glu Leu Arg Ile Trp Ser Val Gln Glu
                325                 330                 335

Asp Asp Leu Ala Ala Gly Leu Ser Trp Ile Pro Phe Phe Gly Pro Gly
            340                 345                 350

Ile Glu Gly Leu Tyr Thr Ala Gly Leu Ile Lys Asn Gln Asn Asn Leu
        355                 360                 365

Val Cys Arg Leu Arg Arg Leu Ala Asn Gln Thr Ala Lys Ser Leu Glu
370                 375                 380

Leu Leu Leu Arg Val Thr Thr Glu Glu Arg Thr Phe Ser Leu Ile Asn
385                 390                 395                 400

Arg His Ala Ile Asp Phe Leu Leu Thr Arg Trp Gly Gly Thr Cys Lys
                405                 410                 415

Val Leu Gly Pro Asp Cys Cys Ile Gly Ile Glu Asp Leu Ser Lys Asn
            420                 425                 430

Ile Ser Glu Gln Ile Asp Lys Ile Arg Lys Asp Glu Gln Lys Glu Glu
        435                 440                 445

Thr Gly
    450

<210> SEQ ID NO 28
<211> LENGTH: 615
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

```
Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270

Glu Leu Ser Phe Thr Val Val Ser Asn Gly Ala Lys Asn Ile Ser Gly
        275                 280                 285

Gln Ser Pro Ala Arg Thr Ser Ser Asp Pro Gly Thr Asn Thr Thr Thr
290                 295                 300

Glu Asp His Lys Ile Met Ala Ser Glu Asn Ser Ser Ala Met Val Gln
305                 310                 315                 320

Val His Ser Gln Gly Arg Glu Ala Ala Val Ser His Leu Thr Thr Leu
                325                 330                 335

Ala Thr Ile Ser Thr Ser Pro Gln Ser Leu Thr Thr Lys Pro Gly Pro
            340                 345                 350

Asp Asn Ser Thr His Asn Thr Pro Val Tyr Lys Leu Asp Ile Ser Glu
        355                 360                 365

Ala Thr Gln Val Glu Gln His His Arg Arg Thr Asp Asn Asp Ser Thr
370                 375                 380

Ala Ser Asp Thr Pro Ser Ala Thr Ala Ala Gly Pro Pro Lys Ala
385                 390                 395                 400
```

-continued

```
Glu Asn Thr Asn Thr Ser Lys Ser Thr Asp Phe Leu Asp Pro Ala Thr
                405                 410                 415

Thr Thr Ser Pro Gln Asn His Ser Glu Thr Ala Gly Asn Asn Asn Thr
            420                 425                 430

His His Gln Asp Thr Gly Glu Glu Ser Ala Ser Ser Gly Lys Leu Gly
        435                 440                 445

Leu Ile Thr Asn Thr Ile Ala Gly Val Ala Gly Leu Ile Thr Gly Gly
    450                 455                 460

Arg Arg Thr Arg Arg Glu Ala Ile Val Asn Ala Gln Pro Lys Cys Asn
465                 470                 475                 480

Pro Asn Leu His Tyr Trp Thr Thr Gln Asp Glu Gly Ala Ala Ile Gly
                485                 490                 495

Leu Ala Trp Ile Pro Tyr Phe Gly Pro Ala Ala Glu Gly Ile Tyr Ile
            500                 505                 510

Glu Gly Leu Met His Asn Gln Asp Gly Leu Ile Cys Gly Leu Arg Gln
        515                 520                 525

Leu Ala Asn Glu Thr Thr Gln Ala Leu Gln Leu Phe Leu Arg Ala Thr
    530                 535                 540

Thr Glu Leu Arg Thr Phe Ser Ile Leu Asn Arg Ala Ala Ile Asp Phe
545                 550                 555                 560

Leu Leu Gln Arg Trp Gly Gly Thr Cys His Ile Leu Gly Pro Asp Cys
                565                 570                 575

Cys Ile Glu Pro His Asp Trp Thr Lys Asn Ile Thr Asp Lys Ile Asp
            580                 585                 590

Gln Ile Ile His Asp Phe Val Asp Lys Thr Leu Pro Asp Gln Gly Asp
        595                 600                 605

Asn Asp Asn Trp Trp Thr Gly
    610                 615

<210> SEQ ID NO 29
<211> LENGTH: 615
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125
```

```
Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
                180                 185                 190

Phe Gly Thr Asn Glu Thr Glu Tyr Leu Phe Glu Val Asp Asn Leu Thr
                195                 200                 205

Tyr Val Gln Leu Glu Ser Arg Phe Thr Pro Gln Phe Leu Leu Gln Leu
210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
                260                 265                 270

Glu Leu Ser Phe Thr Val Val Ser Asn Gly Ala Lys Asn Ile Ser Gly
        275                 280                 285

Gln Ser Pro Ala Arg Thr Ser Ser Asp Pro Gly Thr Asn Thr Thr Thr
    290                 295                 300

Glu Asp His Lys Ile Met Ala Ser Glu Asn Ser Ser Ala Met Val Gln
305                 310                 315                 320

Val His Ser Gln Gly Arg Glu Ala Ala Val Ser His Leu Thr Thr Leu
                325                 330                 335

Ala Thr Ile Ser Thr Ser Pro Gln Ser Leu Thr Thr Lys Pro Gly Pro
                340                 345                 350

Asp Asn Ser Thr His Asn Thr Pro Val Tyr Lys Leu Asp Ile Ser Glu
                355                 360                 365

Ala Thr Gln Val Glu Gln His His Arg Arg Thr Asp Asn Asp Ser Thr
    370                 375                 380

Ala Ser Asp Thr Pro Ser Ala Thr Thr Ala Ala Gly Pro Pro Lys Ala
385                 390                 395                 400

Glu Asn Thr Asn Thr Ser Lys Ser Thr Asp Phe Leu Asp Pro Ala Thr
                405                 410                 415

Thr Thr Ser Pro Gln Asn His Ser Glu Thr Ala Gly Asn Asn Asn Thr
                420                 425                 430

His His Gln Asp Thr Gly Glu Glu Ser Ala Ser Ser Gly Lys Leu Gly
            435                 440                 445

Leu Ile Thr Asn Thr Ile Ala Gly Val Ala Gly Leu Ile Thr Gly Gly
    450                 455                 460

Arg Arg Thr Arg Arg Glu Ala Ile Val Asn Ala Gln Pro Lys Cys Asn
465                 470                 475                 480

Pro Asn Leu His Tyr Trp Thr Thr Gln Asp Glu Gly Ala Ala Ile Gly
                485                 490                 495

Leu Ala Trp Ile Pro Tyr Phe Gly Pro Ala Ala Glu Gly Ile Tyr Ile
                500                 505                 510

Glu Gly Leu Met His Asn Gln Asp Gly Leu Ile Cys Gly Leu Arg Gln
            515                 520                 525

Leu Ala Asn Glu Thr Thr Gln Ala Leu Gln Leu Phe Leu Arg Ala Thr
    530                 535                 540
```

```
Thr Glu Leu Arg Thr Phe Ser Ile Leu Asn Arg Val Ala Ile Asp Phe
545                 550                 555                 560

Leu Leu Gln Arg Trp Gly Gly Thr Cys His Ile Leu Gly Pro Asp Cys
                565                 570                 575

Cys Ile Glu Pro His Asp Trp Thr Lys Asn Ile Thr Asp Lys Ile Asp
            580                 585                 590

Gln Ile Ile His Asp Phe Val Asp Lys Thr Leu Pro Asp Gln Gly Asp
        595                 600                 605

Asn Asp Asn Trp Trp Thr Gly
    610                 615

<210> SEQ ID NO 30
<211> LENGTH: 615
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
                20                  25                  30

Ser Val Gly Leu Asn Leu Glu Gly Asn Gly Val Ala Thr Asp Val Pro
            35                  40                  45

Ser Ala Thr Lys Arg Trp Gly Phe Arg Ser Gly Val Pro Pro Lys Val
50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270
```

```
Glu Leu Ser Phe Thr Val Val Ser Asn Gly Ala Lys Asn Ile Ser Gly
        275                 280                 285

Gln Ser Pro Ala Arg Thr Ser Ser Asp Pro Gly Thr Asn Thr Thr Thr
    290                 295                 300

Glu Asp His Lys Ile Met Ala Ser Glu Asn Ser Ser Ala Met Val Gln
305                 310                 315                 320

Val His Ser Gln Gly Arg Glu Ala Ala Val Ser His Leu Thr Thr Leu
                325                 330                 335

Ala Thr Ile Ser Thr Ser Pro Gln Ser Leu Thr Thr Lys Pro Gly Pro
            340                 345                 350

Asp Asn Ser Thr His Asn Thr Pro Val Tyr Lys Leu Asp Ile Ser Glu
                355                 360                 365

Ala Thr Gln Val Glu Gln His Arg Arg Thr Asp Asn Asp Ser Thr
    370                 375                 380

Ala Ser Asp Thr Pro Ser Ala Thr Thr Ala Ala Gly Pro Pro Lys Ala
385                 390                 395                 400

Glu Asn Thr Asn Thr Ser Lys Ser Thr Asp Phe Leu Asp Pro Ala Thr
                405                 410                 415

Thr Thr Ser Pro Gln Asn His Ser Glu Thr Ala Gly Asn Asn Asn Thr
                420                 425                 430

His His Gln Asp Thr Gly Glu Glu Ser Ala Ser Ser Gly Lys Leu Gly
                435                 440                 445

Leu Ile Thr Asn Thr Ile Ala Gly Val Ala Gly Leu Ile Thr Gly Gly
        450                 455                 460

Arg Arg Thr Arg Arg Glu Ala Ile Val Asn Ala Gln Pro Lys Cys Asn
465                 470                 475                 480

Pro Asn Leu His Tyr Trp Thr Thr Gln Asp Glu Gly Ala Ala Ile Gly
                485                 490                 495

Leu Ala Trp Ile Pro Tyr Phe Gly Pro Ala Ala Glu Gly Ile Tyr Ile
                500                 505                 510

Glu Gly Leu Met His Asn Gln Asp Gly Leu Ile Cys Gly Leu Arg Gln
        515                 520                 525

Leu Ala Asn Glu Thr Thr Gln Ala Leu Gln Leu Phe Leu Arg Ala Thr
    530                 535                 540

Thr Glu Leu Arg Thr Phe Ser Ile Leu Asn Arg Ile Ala Ile Asp Phe
545                 550                 555                 560

Leu Leu Gln Arg Trp Gly Gly Thr Cys His Ile Leu Gly Pro Asp Cys
                565                 570                 575

Cys Ile Glu Pro His Asp Trp Thr Lys Asn Ile Thr Asp Lys Ile Asp
                580                 585                 590

Gln Ile Ile His Asp Phe Val Asp Lys Thr Leu Pro Asp Gln Gly Asp
        595                 600                 605

Asn Asp Asn Trp Trp Thr Gly
    610                 615

<210> SEQ ID NO 31
<211> LENGTH: 615
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 31

```
Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
    210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270

Glu Leu Ser Phe Thr Val Val Ser Asn Gly Ala Lys Asn Ile Ser Gly
        275                 280                 285

Gln Ser Pro Ala Arg Thr Ser Ser Asp Pro Gly Thr Asn Thr Thr Thr
    290                 295                 300

Glu Asp His Lys Ile Met Ala Ser Glu Asn Ser Ser Ala Met Val Gln
305                 310                 315                 320

Val His Ser Gln Gly Arg Glu Ala Ala Val Ser His Leu Thr Thr Leu
                325                 330                 335

Ala Thr Ile Ser Thr Ser Pro Gln Ser Leu Thr Thr Lys Pro Gly Pro
            340                 345                 350

Asp Asn Ser Thr His Asn Thr Pro Val Tyr Lys Leu Asp Ile Ser Glu
        355                 360                 365

Ala Thr Gln Val Glu Gln His His Arg Arg Thr Asp Asn Asp Ser Thr
    370                 375                 380

Ala Ser Asp Thr Pro Ser Ala Thr Ala Ala Gly Pro Pro Lys Ala
385                 390                 395                 400
```

```
Glu Asn Thr Asn Thr Ser Lys Ser Thr Asp Phe Leu Asp Pro Ala Thr
                405                 410                 415

Thr Thr Ser Pro Gln Asn His Ser Glu Thr Ala Gly Asn Asn Asn Thr
            420                 425                 430

His His Gln Asp Thr Gly Glu Glu Ser Ala Ser Ser Gly Lys Leu Gly
        435                 440                 445

Leu Ile Thr Asn Thr Ile Ala Gly Val Ala Gly Leu Ile Thr Gly Gly
    450                 455                 460

Arg Arg Thr Arg Arg Glu Ala Ile Val Asn Ala Gln Pro Lys Cys Asn
465                 470                 475                 480

Pro Asn Leu His Tyr Trp Thr Thr Gln Asp Glu Gly Ala Ala Ile Gly
                485                 490                 495

Leu Ala Trp Ile Pro Tyr Phe Gly Pro Ala Ala Glu Gly Ile Tyr Ile
            500                 505                 510

Glu Gly Leu Met His Asn Gln Asp Gly Leu Ile Cys Gly Leu Arg Gln
        515                 520                 525

Leu Ala Asn Glu Thr Thr Gln Ala Leu Gln Leu Phe Leu Arg Ala Thr
    530                 535                 540

Thr Glu Leu Arg Thr Phe Ser Ile Leu Asn Arg Leu Ala Ile Asp Phe
545                 550                 555                 560

Leu Leu Gln Arg Trp Gly Gly Thr Cys His Ile Leu Gly Pro Asp Cys
                565                 570                 575

Cys Ile Glu Pro His Asp Trp Thr Lys Asn Ile Thr Asp Lys Ile Asp
            580                 585                 590

Gln Ile Ile His Asp Phe Val Asp Lys Thr Leu Pro Asp Gln Gly Asp
        595                 600                 605

Asn Asp Asn Trp Trp Thr Gly
610                 615

<210> SEQ ID NO 32
<211> LENGTH: 615
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125
```

```
Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
                180                 185                 190

Phe Gly Thr Asn Glu Thr Glu Tyr Leu Phe Glu Val Asp Asn Leu Thr
            195                 200                 205

Tyr Val Gln Leu Glu Ser Arg Phe Thr Pro Gln Phe Leu Leu Gln Leu
    210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Ile Gly Glu Trp
                245                 250                 255

Ala Phe Trp Glu Thr Lys Lys Asn Leu Thr Arg Lys Ile Arg Ser Glu
            260                 265                 270

Glu Leu Ser Phe Thr Val Val Ser Asn Gly Ala Lys Asn Ile Ser Gly
    275                 280                 285

Gln Ser Pro Ala Arg Thr Ser Ser Asp Pro Gly Thr Asn Thr Thr Thr
290                 295                 300

Glu Asp His Lys Ile Met Ala Ser Glu Asn Ser Ser Ala Met Val Gln
305                 310                 315                 320

Val His Ser Gln Gly Arg Glu Ala Ala Val Ser His Leu Thr Thr Leu
                325                 330                 335

Ala Thr Ile Ser Thr Ser Pro Gln Ser Leu Thr Thr Lys Pro Gly Pro
            340                 345                 350

Asp Asn Ser Thr His Asn Thr Pro Val Tyr Lys Leu Asp Ile Ser Glu
            355                 360                 365

Ala Thr Gln Val Glu Gln His His Arg Arg Thr Asp Asn Asp Ser Thr
    370                 375                 380

Ala Ser Asp Thr Pro Ser Ala Thr Thr Ala Ala Gly Pro Pro Lys Ala
385                 390                 395                 400

Glu Asn Thr Asn Thr Ser Lys Ser Thr Asp Phe Leu Asp Pro Ala Thr
                405                 410                 415

Thr Thr Ser Pro Gln Asn His Ser Glu Thr Ala Gly Asn Asn Asn Thr
            420                 425                 430

His His Gln Asp Thr Gly Glu Glu Ser Ala Ser Ser Gly Lys Leu Gly
    435                 440                 445

Leu Ile Thr Asn Thr Ile Ala Gly Val Ala Gly Leu Ile Thr Gly Gly
    450                 455                 460

Arg Arg Thr Arg Arg Glu Ala Ile Val Asn Ala Gln Pro Lys Cys Asn
465                 470                 475                 480

Pro Asn Leu His Tyr Trp Thr Thr Gln Asp Glu Gly Ala Ala Ile Gly
                485                 490                 495

Leu Ala Trp Ile Pro Tyr Phe Gly Pro Ala Ala Glu Gly Ile Tyr Ile
                500                 505                 510

Glu Gly Leu Met His Asn Gln Asp Gly Leu Ile Cys Gly Leu Arg Gln
            515                 520                 525

Leu Ala Asn Glu Thr Thr Gln Ala Leu Gln Leu Phe Leu Arg Ala Thr
530                 535                 540
```

```
Thr Glu Leu Arg Thr Phe Ser Ile Leu Asn Arg Met Ala Ile Asp Phe
545                 550                 555                 560

Leu Leu Gln Arg Trp Gly Gly Thr Cys His Ile Leu Gly Pro Asp Cys
                565                 570                 575

Cys Ile Glu Pro His Asp Trp Thr Lys Asn Ile Thr Asp Lys Ile Asp
            580                 585                 590

Gln Ile Ile His Asp Phe Val Asp Lys Thr Leu Pro Asp Gln Gly Asp
        595                 600                 605

Asn Asp Asn Trp Trp Thr Gly
        610                 615

<210> SEQ ID NO 33
<211> LENGTH: 615
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
    210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270
```

Glu Leu Ser Phe Thr Val Val Ser Asn Gly Ala Lys Asn Ile Ser Gly
275                 280                 285

Gln Ser Pro Ala Arg Thr Ser Ser Asp Pro Gly Thr Asn Thr Thr Thr
290                 295                 300

Glu Asp His Lys Ile Met Ala Ser Glu Asn Ser Ser Ala Met Val Gln
305                 310                 315                 320

Val His Ser Gln Gly Arg Glu Ala Ala Val Ser His Leu Thr Thr Leu
                325                 330                 335

Ala Thr Ile Ser Thr Ser Pro Gln Ser Leu Thr Thr Lys Pro Gly Pro
                340                 345                 350

Asp Asn Ser Thr His Asn Thr Pro Val Tyr Lys Leu Asp Ile Ser Glu
                355                 360                 365

Ala Thr Gln Val Glu Gln His His Arg Arg Thr Asp Asn Asp Ser Thr
370                 375                 380

Ala Ser Asp Thr Pro Ser Ala Thr Thr Ala Ala Gly Pro Pro Lys Ala
385                 390                 395                 400

Glu Asn Thr Asn Thr Ser Lys Ser Thr Asp Phe Leu Asp Pro Ala Thr
                405                 410                 415

Thr Thr Ser Pro Gln Asn His Ser Glu Thr Ala Gly Asn Asn Asn Thr
                420                 425                 430

His His Gln Asp Thr Gly Glu Glu Ser Ala Ser Ser Gly Lys Leu Gly
                435                 440                 445

Leu Ile Thr Asn Thr Ile Ala Gly Val Ala Gly Leu Ile Thr Gly Gly
450                 455                 460

Arg Arg Thr Arg Arg Glu Ala Ile Val Asn Ala Gln Pro Lys Cys Asn
465                 470                 475                 480

Pro Asn Leu His Tyr Trp Thr Thr Gln Asp Glu Gly Ala Ala Ile Gly
                485                 490                 495

Leu Ala Trp Ile Pro Tyr Phe Gly Pro Ala Ala Glu Gly Ile Tyr Ile
                500                 505                 510

Glu Gly Leu Met His Asn Gln Asp Gly Leu Ile Cys Gly Leu Arg Gln
                515                 520                 525

Leu Ala Asn Glu Thr Thr Gln Ala Leu Gln Leu Phe Leu Arg Ala Thr
530                 535                 540

Thr Glu Leu Arg Thr Phe Ser Ile Leu Asn Arg Tyr Ala Ile Asp Phe
545                 550                 555                 560

Leu Leu Gln Arg Trp Gly Gly Thr Cys His Ile Leu Gly Pro Asp Cys
                565                 570                 575

Cys Ile Glu Pro His Asp Trp Thr Lys Asn Ile Thr Asp Lys Ile Asp
                580                 585                 590

Gln Ile Ile His Asp Phe Val Asp Lys Thr Leu Pro Asp Gln Gly Asp
                595                 600                 605

Asn Asp Asn Trp Trp Thr Gly
610                 615

<210> SEQ ID NO 34
<211> LENGTH: 458
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

```
Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270

Glu Leu Ser Phe Thr Val Val Ser Asn Gly Ala Lys Asn Ile Ser Gly
        275                 280                 285

Lys Leu Gly Leu Ile Thr Asn Thr Ile Ala Gly Val Ala Gly Leu Ile
290                 295                 300

Thr Gly Gly Arg Arg Thr Arg Arg Glu Ala Ile Val Asn Ala Gln Pro
305                 310                 315                 320

Lys Cys Asn Pro Asn Leu His Tyr Trp Thr Thr Gln Asp Glu Gly Ala
                325                 330                 335

Ala Ile Gly Leu Ala Trp Ile Pro Tyr Phe Gly Pro Ala Ala Glu Gly
            340                 345                 350

Ile Tyr Ile Glu Gly Leu Met His Asn Gln Asp Gly Leu Ile Cys Gly
        355                 360                 365

Leu Arg Gln Leu Ala Asn Glu Thr Thr Gln Ala Leu Gln Leu Phe Leu
370                 375                 380

Arg Ala Thr Thr Glu Leu Arg Thr Phe Ser Ile Leu Asn Arg Ala Ala
385                 390                 395                 400
```

```
Ile Asp Phe Leu Leu Gln Arg Trp Gly Gly Thr Cys His Ile Leu Gly
            405                 410                 415

Pro Asp Cys Cys Ile Glu Pro His Asp Trp Thr Lys Asn Ile Thr Asp
            420                 425                 430

Lys Ile Asp Gln Ile Ile His Asp Phe Val Lys Thr Leu Pro Asp
            435                 440                 445

Gln Gly Asp Asn Asp Asn Trp Trp Thr Gly
    450                 455

<210> SEQ ID NO 35
<211> LENGTH: 458
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
    210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270

Glu Leu Ser Phe Thr Val Val Ser Asn Gly Ala Lys Asn Ile Ser Gly
        275                 280                 285
```

```
Lys Leu Gly Leu Ile Thr Asn Thr Ile Ala Gly Val Ala Gly Leu Ile
    290                 295                 300

Thr Gly Gly Arg Arg Thr Arg Arg Glu Ala Ile Val Asn Ala Gln Pro
305                 310                 315                 320

Lys Cys Asn Pro Asn Leu His Tyr Trp Thr Thr Gln Asp Glu Gly Ala
                325                 330                 335

Ala Ile Gly Leu Ala Trp Ile Pro Tyr Phe Gly Pro Ala Ala Glu Gly
            340                 345                 350

Ile Tyr Ile Glu Gly Leu Met His Asn Gln Asp Gly Leu Ile Cys Gly
        355                 360                 365

Leu Arg Gln Leu Ala Asn Glu Thr Thr Gln Ala Leu Gln Leu Phe Leu
    370                 375                 380

Arg Ala Thr Thr Glu Leu Arg Thr Phe Ser Ile Leu Asn Arg Val Ala
385                 390                 395                 400

Ile Asp Phe Leu Leu Gln Arg Trp Gly Gly Thr Cys His Ile Leu Gly
                405                 410                 415

Pro Asp Cys Cys Ile Glu Pro His Asp Trp Thr Lys Asn Ile Thr Asp
            420                 425                 430

Lys Ile Asp Gln Ile Ile His Asp Phe Val Asp Lys Thr Leu Pro Asp
        435                 440                 445

Gln Gly Asp Asn Asp Asn Trp Trp Thr Gly
    450                 455

<210> SEQ ID NO 36
<211> LENGTH: 458
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175
```

```
Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
            195                 200                 205

Tyr Val Gln Leu Glu Ser Arg Phe Thr Pro Gln Phe Leu Leu Gln Leu
            210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
            245                 250                 255

Ala Phe Trp Glu Thr Lys Lys Asn Leu Thr Arg Lys Ile Arg Ser Glu
            260                 265                 270

Glu Leu Ser Phe Thr Val Val Ser Asn Gly Ala Lys Asn Ile Ser Gly
            275                 280                 285

Lys Leu Gly Leu Ile Thr Asn Thr Ile Ala Gly Val Ala Gly Leu Ile
            290                 295                 300

Thr Gly Gly Arg Arg Thr Arg Arg Glu Ala Ile Val Asn Ala Gln Pro
305                 310                 315                 320

Lys Cys Asn Pro Asn Leu His Tyr Trp Thr Thr Gln Asp Glu Gly Ala
            325                 330                 335

Ala Ile Gly Leu Ala Trp Ile Pro Tyr Phe Gly Pro Ala Ala Glu Gly
            340                 345                 350

Ile Tyr Ile Glu Gly Leu Met His Asn Gln Asp Gly Leu Ile Cys Gly
            355                 360                 365

Leu Arg Gln Leu Ala Asn Glu Thr Thr Gln Ala Leu Gln Leu Phe Leu
            370                 375                 380

Arg Ala Thr Thr Glu Leu Arg Thr Phe Ser Ile Leu Asn Arg Ile Ala
385                 390                 395                 400

Ile Asp Phe Leu Leu Gln Arg Trp Gly Gly Thr Cys His Ile Leu Gly
            405                 410                 415

Pro Asp Cys Cys Ile Glu Pro His Asp Trp Thr Lys Asn Ile Thr Asp
            420                 425                 430

Lys Ile Asp Gln Ile Ile His Asp Phe Val Asp Lys Thr Leu Pro Asp
            435                 440                 445

Gln Gly Asp Asn Asp Asn Trp Trp Thr Gly
            450                 455

<210> SEQ ID NO 37
<211> LENGTH: 458
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
            35                  40                  45

Ser Ala Thr Lys Arg Trp Gly Phe Arg Ser Gly Val Pro Pro Lys Val
            50                  55                  60
```

```
Val Asn Tyr Glu Ala Gly Glu Trp Ala Glu Asn Cys Tyr Asn Leu Glu
 65                  70                  75                  80

Ile Lys Lys Pro Asp Gly Ser Glu Cys Leu Pro Ala Pro Asp Gly
                 85                  90                  95

Ile Arg Gly Phe Pro Arg Cys Arg Tyr Val His Lys Val Ser Gly Thr
                100                 105                 110

Gly Pro Cys Ala Gly Asp Phe Ala Phe His Lys Glu Gly Ala Phe Phe
            115                 120                 125

Leu Tyr Asp Arg Leu Ala Ser Thr Val Ile Tyr Arg Gly Thr Thr Phe
130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270

Glu Leu Ser Phe Thr Val Val Ser Asn Gly Ala Lys Asn Ile Ser Gly
        275                 280                 285

Lys Leu Gly Leu Ile Thr Asn Thr Ile Ala Gly Val Ala Gly Leu Ile
290                 295                 300

Thr Gly Gly Arg Arg Thr Arg Arg Glu Ala Ile Val Asn Ala Gln Pro
305                 310                 315                 320

Lys Cys Asn Pro Asn Leu His Tyr Trp Thr Thr Gln Asp Glu Gly Ala
                325                 330                 335

Ala Ile Gly Leu Ala Trp Ile Pro Tyr Phe Gly Pro Ala Ala Glu Gly
            340                 345                 350

Ile Tyr Ile Glu Gly Leu Met His Asn Gln Asp Gly Leu Ile Cys Gly
        355                 360                 365

Leu Arg Gln Leu Ala Asn Glu Thr Thr Gln Ala Leu Gln Leu Phe Leu
370                 375                 380

Arg Ala Thr Thr Glu Leu Arg Thr Phe Ser Ile Leu Asn Arg Leu Ala
385                 390                 395                 400

Ile Asp Phe Leu Leu Gln Arg Trp Gly Gly Thr Cys His Ile Leu Gly
                405                 410                 415

Pro Asp Cys Cys Ile Glu Pro His Asp Trp Thr Lys Asn Ile Thr Asp
            420                 425                 430

Lys Ile Asp Gln Ile Ile His Asp Phe Val Asp Lys Thr Leu Pro Asp
        435                 440                 445

Gln Gly Asp Asn Asp Asn Trp Trp Thr Gly
    450                 455

<210> SEQ ID NO 38
<211> LENGTH: 459
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
    210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270

Glu Leu Ser Phe Thr Val Val Ser Asn Gly Ala Lys Asn Ile Ser Gly
        275                 280                 285

Lys Leu Gly Leu Ile Thr Asn Thr Ile Ala Gly Val Ala Gly Leu Ile
    290                 295                 300

Thr Gly Gly Arg Arg Thr Arg Arg Glu Ala Ile Val Asn Ala Gln Pro
305                 310                 315                 320

Lys Cys Asn Pro Asn Leu His Tyr Trp Thr Thr Gln Asp Glu Gly Ala
                325                 330                 335

Ala Ile Gly Leu Ala Trp Ile Pro Tyr Phe Gly Pro Ala Ala Glu Gly
            340                 345                 350

Ile Tyr Ile Glu Gly Leu Met His Asn Gln Asp Gly Leu Ile Cys Gly
        355                 360                 365

Leu Arg Gln Leu Ala Asn Glu Thr Thr Gln Ala Leu Gln Leu Phe Leu
    370                 375                 380

```
Arg Ala Thr Thr Glu Leu Arg Thr Phe Ser Ile Leu Asn Arg Met Ala
385                 390                 395                 400

Ile Asp Phe Leu Leu Gln Arg Trp Gly Gly Thr Cys His Ile Leu Gly
                405                 410                 415

Pro Asp Cys Cys Ile Glu Pro His Asp Trp Thr Lys Asn Ile Thr Asp
            420                 425                 430

Lys Ile Asp Gln Ile Ile His Asp Phe Val Asp Lys Thr Leu Pro Asp
        435                 440                 445

Gln Gly Asp Asn Asp Asn Trp Trp Thr Gly His
    450                 455
```

<210> SEQ ID NO 39
<211> LENGTH: 458
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 39

```
Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
                20                  25                  30

Ser Val Gly Leu Asn Leu Glu Gly Asn Gly Val Ala Thr Asp Val Pro
            35                  40                  45

Ser Ala Thr Lys Arg Trp Gly Phe Arg Ser Gly Val Pro Pro Lys Val
50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
    210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270
```

```
Glu Leu Ser Phe Thr Val Val Ser Asn Gly Ala Lys Asn Ile Ser Gly
            275                 280                 285

Lys Leu Gly Leu Ile Thr Asn Thr Ile Ala Gly Val Ala Gly Leu Ile
        290                 295                 300

Thr Gly Gly Arg Arg Thr Arg Arg Glu Ala Ile Val Asn Ala Gln Pro
305                 310                 315                 320

Lys Cys Asn Pro Asn Leu His Tyr Trp Thr Thr Gln Asp Glu Gly Ala
                325                 330                 335

Ala Ile Gly Leu Ala Trp Ile Pro Tyr Phe Gly Pro Ala Ala Glu Gly
            340                 345                 350

Ile Tyr Ile Glu Gly Leu Met His Asn Gln Asp Gly Leu Ile Cys Gly
355                 360                 365

Leu Arg Gln Leu Ala Asn Glu Thr Thr Gln Ala Leu Gln Leu Phe Leu
        370                 375                 380

Arg Ala Thr Thr Glu Leu Arg Thr Phe Ser Ile Leu Asn Arg Tyr Ala
385                 390                 395                 400

Ile Asp Phe Leu Leu Gln Arg Trp Gly Thr Cys His Ile Leu Gly
                405                 410                 415

Pro Asp Cys Cys Ile Glu Pro His Asp Trp Thr Lys Asn Ile Thr Asp
            420                 425                 430

Lys Ile Asp Gln Ile Ile His Asp Phe Val Asp Lys Thr Leu Pro Asp
        435                 440                 445

Gln Gly Asp Asn Asp Asn Trp Trp Thr Gly
    450                 455

<210> SEQ ID NO 40
<211> LENGTH: 458
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ala Lys Lys Asp
145                 150                 155                 160
```

```
Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
    210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
            260                 265                 270

Glu Leu Ser Phe Thr Val Val Ser Asn Gly Ala Lys Asn Ile Ser Gly
        275                 280                 285

Lys Leu Gly Leu Ile Thr Asn Thr Ile Ala Gly Val Ala Gly Leu Ile
    290                 295                 300

Thr Gly Gly Arg Arg Thr Arg Arg Glu Ala Ile Val Asn Ala Gln Pro
305                 310                 315                 320

Lys Cys Asn Pro Asn Leu His Tyr Trp Thr Thr Gln Asp Glu Gly Ala
                325                 330                 335

Ala Ile Gly Leu Ala Trp Ile Pro Tyr Phe Gly Pro Ala Ala Glu Gly
            340                 345                 350

Ile Tyr Ile Glu Gly Leu Met His Asn Gln Asp Gly Leu Ile Cys Gly
        355                 360                 365

Leu Arg Gln Leu Ala Asn Glu Thr Thr Gln Ala Leu Gln Leu Phe Leu
    370                 375                 380

Arg Ala Thr Thr Glu Leu Arg Thr Phe Ser Ile Leu Asn Arg Trp Ala
385                 390                 395                 400

Ile Asp Phe Leu Leu Gln Arg Trp Gly Gly Thr Cys His Ile Leu Gly
                405                 410                 415

Pro Asp Cys Cys Ile Glu Pro His Asp Trp Thr Lys Asn Ile Thr Asp
            420                 425                 430

Lys Ile Asp Gln Ile Ile His Asp Phe Val Asp Lys Thr Leu Pro Asp
        435                 440                 445

Gln Gly Asp Asn Asp Asn Trp Trp Thr Gly
450                 455

<210> SEQ ID NO 41
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Leu Pro Val Leu Glu Ile Ala Ser Asn Ser Gln Pro Gln Asp Val Asp
1               5                   10                  15

Ser Val Cys Ser Gly Thr Leu Gln Lys Thr Glu Asp Val His Leu Met
            20                  25                  30

Gly Phe Thr Leu Ser Gly Gln Lys Val Ala Asp Ser Pro Leu Glu Ala
        35                  40                  45
```

-continued

```
Ser Lys Arg Trp Ala Phe Arg Thr Gly Val Pro Lys Asn Val Glu
 50                  55                  60
Tyr Thr Glu Gly Glu Ala Lys Thr Cys Tyr Asn Ile Ser Val Thr
 65                  70                  75                  80
Asp Pro Ser Gly Lys Ser Leu Leu Asp Pro Pro Ser Asn Ile Arg
                 85                  90                  95
Asp Tyr Pro Lys Cys Lys Thr Val His His Ile Gln Gly Gln Asn Pro
                100                 105                 110
His Ala Gln Gly Ile Ala Leu His Leu Trp Gly Ala Phe Phe Leu Tyr
            115                 120                 125
Asp Arg Val Ala Ser Thr Thr Met Tyr Arg Gly Lys Val Phe Thr Glu
130                 135                 140
Gly Asn Ile Ala Ala Met Ile Val Asn Lys Thr Val His Arg Met Ile
145                 150                 155                 160
Phe Ser Arg Gln Gly Gln Gly Tyr Arg His Met Asn Leu Thr Ser Thr
                165                 170                 175
Asn Lys Tyr Trp Thr Ser Ser Asn Glu Thr Gln Arg Asn Asp Thr Gly
            180                 185                 190
Cys Phe Gly Ile Leu Gln Glu Tyr Asn Ser Thr Asn Asn Gln Thr Cys
        195                 200                 205
Pro Pro Ser Leu Lys Pro Pro Ser Leu Pro Thr Val Thr Pro Ser Ile
    210                 215                 220
His Ser Thr Asn Thr Gln Ile Asn Thr Ala Lys Ser Gly Thr Arg Pro
225                 230                 235                 240
Pro Ile Tyr Phe Arg Lys Arg Ser Ile Leu Ala Lys Glu Gly Asp
                245                 250                 255
Ile Gly Pro Asn Leu Asp Gly Leu Ile Asn Thr Glu Ile Asp Phe Asp
            260                 265                 270
Pro Ile Pro Asn Thr Glu Thr Ile Phe Asp Glu Ser Pro Ser Phe Asn
        275                 280                 285
Thr Ser Thr Asn Glu Glu Gln His Thr Pro Pro Asn Ile Ser Leu Thr
    290                 295                 300
Phe Ser Tyr Phe Pro Asp Lys Asn Gly Asp Thr Ala Tyr Ser Gly Glu
305                 310                 315                 320
Asn Glu Asn Asp Cys Asp Ala Glu Leu Arg Ile Trp Ser Val Gln Glu
                325                 330                 335
Asp Asp Leu Ala Ala Gly Leu Ser Trp Ile Pro Phe Phe Gly Pro Gly
            340                 345                 350
Ile Glu Gly Leu Tyr Thr Ala Gly Leu Ile Lys Asn Gln Asn Asn Leu
        355                 360                 365
Val Cys Arg Leu Arg Arg Leu Ala Asn Gln Thr Ala Lys Ser Leu Glu
    370                 375                 380
Leu Leu Leu Arg Val Thr Thr Glu Glu Arg Thr Phe Ser Leu Ile Asn
385                 390                 395                 400
Arg Phe Ala Ile Asp Phe Leu Leu Thr Arg Trp Gly Gly Thr Cys Lys
                405                 410                 415
Val Leu Gly Pro Asp Cys Cys Ile Gly Ile Glu Asp Leu Ser Lys Asn
            420                 425                 430
Ile Ser Glu Gln Ile Asp Lys Ile Arg Lys Asp Glu Gln Lys Glu Glu
        435                 440                 445
Thr Gly
450
```

-continued

```
<210> SEQ ID NO 42
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Leu Pro Val Leu Glu Ile Ala Ser Asn Ser Gln Pro Gln Asp Val Asp
1               5                   10                  15

Ser Val Cys Ser Gly Thr Leu Gln Lys Thr Glu Asp Val His Leu Met
            20                  25                  30

Gly Phe Thr Leu Ser Gly Gln Lys Val Ala Asp Ser Pro Leu Glu Ala
        35                  40                  45

Ser Lys Arg Trp Ala Phe Arg Thr Gly Val Pro Pro Lys Asn Val Glu
    50                  55                  60

Tyr Thr Glu Gly Glu Glu Ala Lys Thr Cys Tyr Asn Ile Ser Val Thr
65                  70                  75                  80

Asp Pro Ser Gly Lys Ser Leu Leu Asp Pro Pro Ser Asn Ile Arg
            85                  90                  95

Asp Tyr Pro Lys Cys Lys Thr Val His Ile Gln Gly Gln Asn Pro
            100                 105                 110

His Ala Gln Gly Ile Ala Leu His Leu Trp Gly Ala Phe Phe Leu Tyr
        115                 120                 125

Asp Arg Val Ala Ser Thr Thr Met Tyr Arg Gly Lys Val Phe Thr Glu
    130                 135                 140

Gly Asn Ile Ala Ala Met Ile Val Asn Lys Thr Val His Arg Met Ile
145                 150                 155                 160

Phe Ser Arg Gln Gly Gln Gly Tyr Arg His Met Asn Leu Thr Ser Thr
                165                 170                 175

Asn Lys Tyr Trp Thr Ser Ser Asn Glu Thr Gln Arg Asn Asp Thr Gly
            180                 185                 190

Cys Phe Gly Ile Leu Gln Glu Tyr Asn Ser Thr Asn Asn Gln Thr Cys
        195                 200                 205

Pro Pro Ser Leu Lys Pro Pro Ser Leu Pro Thr Val Thr Pro Ser Ile
    210                 215                 220

His Ser Thr Asn Thr Gln Ile Asn Thr Ala Lys Ser Gly Thr Arg Pro
225                 230                 235                 240

Pro Ile Tyr Phe Arg Lys Lys Arg Ser Ile Leu Ala Lys Glu Gly Asp
                245                 250                 255

Ile Gly Pro Asn Leu Asp Gly Leu Ile Asn Thr Glu Ile Asp Phe Asp
            260                 265                 270

Pro Ile Pro Asn Thr Glu Thr Ile Phe Asp Glu Ser Pro Ser Phe Asn
        275                 280                 285

Thr Ser Thr Asn Glu Glu Gln His Thr Pro Asn Ile Ser Leu Thr
    290                 295                 300

Phe Ser Tyr Phe Pro Asp Lys Asn Gly Asp Thr Ala Tyr Ser Gly Glu
305                 310                 315                 320

Asn Glu Asn Asp Cys Asp Ala Glu Leu Arg Ile Trp Ser Val Gln Glu
                325                 330                 335

Asp Asp Leu Ala Ala Gly Leu Ser Trp Ile Pro Phe Phe Gly Pro Gly
            340                 345                 350

Ile Glu Gly Leu Tyr Thr Ala Gly Leu Ile Lys Asn Gln Asn Asn Leu
        355                 360                 365
```

```
Val Cys Arg Leu Arg Arg Leu Ala Asn Gln Thr Ala Lys Ser Leu Glu
        370                 375                 380

Leu Leu Leu Arg Val Thr Thr Glu Glu Arg Thr Phe Ser Leu Ile Asn
385                 390                 395                 400

Arg Ile Ala Ile Asp Phe Leu Leu Thr Arg Trp Gly Gly Thr Cys Lys
            405                 410                 415

Val Leu Gly Pro Asp Cys Cys Ile Gly Ile Glu Asp Leu Ser Lys Asn
            420                 425                 430

Ile Ser Glu Gln Ile Asp Lys Ile Arg Lys Asp Glu Gln Lys Glu Glu
        435                 440                 445

Thr Gly
    450

<210> SEQ ID NO 43
<211> LENGTH: 637
<212> TYPE: PRT
<213> ORGANISM: Marburg marburgvirus

<400> SEQUENCE: 43

Met Lys Thr Ile Tyr Phe Leu Ile Ser Leu Ile Leu Ile Gln Ser Ile
1               5                   10                  15

Lys Thr Leu Pro Val Leu Glu Ile Ala Ser Asn Ser Gln Pro Gln Asp
            20                  25                  30

Val Asp Ser Val Cys Ser Gly Thr Leu Gln Lys Thr Glu Asp Val His
        35                  40                  45

Leu Met Gly Phe Thr Leu Ser Gly Gln Lys Val Ala Asp Ser Pro Leu
    50                  55                  60

Glu Ala Ser Lys Arg Trp Ala Phe Arg Thr Gly Val Pro Pro Lys Asn
65                  70                  75                  80

Val Glu Tyr Thr Glu Gly Glu Ala Lys Thr Cys Tyr Asn Ile Ser
                85                  90                  95

Val Thr Asp Pro Ser Gly Lys Ser Leu Leu Leu Asp Pro Pro Ser Asn
            100                 105                 110

Ile Arg Asp Tyr Pro Lys Cys Lys Thr Val His His Ile Gln Gly Gln
        115                 120                 125

Asn Pro His Ala Gln Gly Ile Ala Leu His Leu Trp Gly Ala Phe Phe
    130                 135                 140

Leu Tyr Asp Arg Val Ala Ser Thr Thr Met Tyr Arg Gly Lys Val Phe
145                 150                 155                 160

Thr Glu Gly Asn Ile Ala Ala Met Ile Val Asn Lys Thr Val His Arg
                165                 170                 175

Met Ile Phe Ser Arg Gln Gly Gln Gly Tyr Arg His Met Asn Leu Thr
            180                 185                 190

Ser Thr Asn Lys Tyr Trp Thr Ser Ser Asn Glu Thr Arg Arg Asn Asp
        195                 200                 205

Thr Gly Cys Phe Gly Ile Leu Gln Glu Tyr Asn Ser Thr Asn Asn Gln
    210                 215                 220

Thr Cys Ser Pro Ser Leu Lys Pro Pro Ser Leu Pro Thr Val Thr Pro
225                 230                 235                 240

Ser Ile His Ser Thr Asn Thr Gln Ile Asn Thr Ala Lys Ser Gly Thr
                245                 250                 255

Ile Asn Pro Ser Ser Asp Asp Glu Asp Leu Met Val Ser Gly Ser Gly
            260                 265                 270
```

Ser Gly Glu Gln Gly Pro His Thr Thr Leu Asn Val Thr Glu Gln
    275                 280                 285

Lys Gln Ser Ser Thr Ile Leu Ser Thr Pro Ser Leu His Pro Ser Thr
290                 295                 300

Pro Gln His Glu Gln Asn Ser Thr Asn Pro Ser Arg His Ala Val Thr
305                 310                 315                 320

Glu His Asn Gly Thr Asp Pro Thr Thr Gln Pro Ala Thr Leu Leu Asn
                325                 330                 335

Asn Thr Asn Thr Thr Pro Thr Tyr Asn Thr Leu Lys Tyr Asn Leu Ser
            340                 345                 350

Thr Pro Ser Pro Pro Thr Arg Asn Ile Thr Asn Asn Asp Thr Gln Arg
        355                 360                 365

Glu Leu Ala Glu Ser Glu Gln Thr Asn Ala Gln Leu Asn Thr Thr Pro
    370                 375                 380

Asp Pro Thr Glu Asn Pro Thr Thr Ala Gln Asp Thr Asn Ser Thr Thr
385                 390                 395                 400

Asn Ile Thr Met Thr Thr Ser Asp Ile Thr Ser Lys His Pro Thr Asn
                405                 410                 415

Ser Ser Pro Asp Ser Ser Pro Thr Thr Arg Pro Pro Ile Tyr Phe Arg
            420                 425                 430

Lys Lys Arg Ser Ile Phe Trp Lys Glu Gly Asp Ile Phe Pro Phe Leu
        435                 440                 445

Asp Gly Leu Ile Asn Thr Glu Ile Asp Phe Asp Pro Ile Pro Asn Thr
    450                 455                 460

Glu Thr Ile Phe Asp Glu Ser Pro Ser Phe Asn Thr Ser Thr Asn Glu
465                 470                 475                 480

Glu Gln His Thr Pro Pro Asn Ile Ser Leu Thr Phe Ser Tyr Phe Pro
                485                 490                 495

Asp Lys Asn Gly Asp Thr Ala Tyr Ser Gly Glu Asn Glu Asn Asp Cys
            500                 505                 510

Asp Ala Glu Leu Arg Ile Trp Ser Val Gln Glu Asp Asp Leu Ala Ala
        515                 520                 525

Gly Leu Ser Trp Ile Pro Phe Phe Gly Pro Gly Ile Glu Gly Leu Tyr
    530                 535                 540

Thr Ala Gly Leu Ile Lys Asn Gln Asn Asn Leu Val Cys Arg Leu Arg
545                 550                 555                 560

Arg Leu Ala Asn Gln Thr Ala Lys Ser Leu Glu Leu Leu Arg Val
                565                 570                 575

Thr Thr Glu Glu Arg Thr Phe Ser Leu Ile Asn Arg His Ala Ile Asp
            580                 585                 590

Phe Leu Leu Thr Arg Trp Gly Gly Thr Cys Lys Val Leu Gly Pro Asp
        595                 600                 605

Cys Cys Ile Gly Ile Glu Asp Leu Ser Lys Asn Ile Ser Glu Gln Ile
    610                 615                 620

Asp Lys Ile Arg Lys Asp Glu Gln Lys Glu Thr Gly
625                 630                 635

<210> SEQ ID NO 44
<211> LENGTH: 32
<212> TYPE: PRT
<213> ORGANISM: Zaire ebolavirus

```
<400> SEQUENCE: 44

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

<210> SEQ ID NO 45
<211> LENGTH: 18
<212> TYPE: PRT
<213> ORGANISM: Marburg marburgvirus

<400> SEQUENCE: 45

Met Lys Thr Ile Tyr Phe Leu Ile Ser Leu Ile Leu Ile Gln Ser Ile
1               5                   10                  15

Lys Thr

<210> SEQ ID NO 46
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 46

His His His His His His
1               5
```